(12) United States Patent
Nagasuna et al.

(10) Patent No.: US 8,426,670 B2
(45) Date of Patent: Apr. 23, 2013

(54) ABSORBENT STRUCTURE, ABSORBENT ARTICLE, WATER-ABSORBENT RESIN, AND ITS PRODUCTION PROCESS AND EVALUATION METHOD

(75) Inventors: Kinya Nagasuna, Nara (JP); Kenji Kadonaga, Takatsuki (JP); Akiko Mitsuhashi, Sanda (JP); Motohiro Imura, Takatsuki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 1288 days.

(21) Appl. No.: 10/416,457

(22) PCT Filed: Sep. 18, 2002

(86) PCT No.: PCT/JP02/09567
§ 371 (c)(1),
(2), (4) Date: May 12, 2003

(87) PCT Pub. No.: WO03/026707
PCT Pub. Date: Apr. 3, 2003

(65) Prior Publication Data
US 2004/0019342 A1    Jan. 29, 2004

(30) Foreign Application Priority Data

| Sep. 19, 2001 | (JP) | 2001-285752 |
| Dec. 10, 2001 | (JP) | 2001-375375 |
| Mar. 15, 2002 | (JP) | 2002-072476 |
| Apr. 9, 2002 | (JP) | 2002-106565 |

(51) Int. Cl.
*A61F 13/15* (2006.01)

(52) U.S. Cl.
USPC .......................................... 604/368; 526/88

(58) Field of Classification Search .................. 604/368; 526/88
See application file for complete search history.

(56) References Cited

U.S. PATENT DOCUMENTS

| 3,935,099 A | 1/1976 | Weaver et al. |
| 3,959,569 A | 5/1976 | Burkholder, Jr. |
| 4,076,663 A | 2/1978 | Masuda et al. |
| 4,093,776 A | 6/1978 | Aoki et al. |
| 4,124,748 A | 11/1978 | Fujimoto et al. |
| 4,367,323 A | 1/1983 | Kitamura et al. |
| 4,386,120 A | 5/1983 | Sato et al. |
| 4,389,513 A | 6/1983 | Miyazaki |
| 4,446,261 A | 5/1984 | Yamasaki et al. |
| 4,625,001 A | 11/1986 | Tsubakimoto et al. |
| 4,654,039 A | 3/1987 | Brandt et al. |
| 4,666,983 A | 5/1987 | Tsubakimoto et al. |
| 4,683,274 A | 7/1987 | Nakamura et al. |
| 4,690,996 A | 9/1987 | Shih et al. |
| 4,721,647 A | 1/1988 | Nakanishi et al. |
| 4,734,478 A * | 3/1988 | Tsubakimoto et al. ....... 527/300 |
| 4,738,867 A | 4/1988 | Itoh et al. |
| 4,748,076 A | 5/1988 | Saotome |
| 4,769,427 A | 9/1988 | Nowakowsky et al. |
| 4,781,710 A | 11/1988 | Megison et al. |
| 4,873,299 A | 10/1989 | Nowakowsky et al. |
| 5,134,007 A | 7/1992 | Reising et al. |
| 5,164,459 A * | 11/1992 | Kimura et al. ................. 525/384 |
| 5,189,070 A | 2/1993 | Brownscombe et al. |
| 5,250,576 A | 10/1993 | DesMarais et al. |
| 5,250,640 A | 10/1993 | Irie et al. |
| 5,252,619 A | 10/1993 | Brownscombe et al. |
| 5,275,773 A | 1/1994 | Irie et al. |
| 5,290,820 A | 3/1994 | Brownscombe et al. |
| 5,358,974 A | 10/1994 | Brownscombe et al. |
| 5,387,207 A | 2/1995 | Dyer et al. |
| 5,509,915 A | 4/1996 | Hanson et al. |
| 5,632,737 A | 5/1997 | Stone et al. |
| 5,670,101 A | 9/1997 | Nathoo et al. |
| 5,851,648 A | 12/1998 | Stone et al. |
| 6,107,538 A * | 8/2000 | Young et al. .................. 604/369 |
| 6,204,298 B1 | 3/2001 | DesMarais et al. |
| 6,207,772 B1 * | 3/2001 | Hatsuda et al. ................. 526/88 |

FOREIGN PATENT DOCUMENTS

| EP | 0251676 | 1/1988 |
| EP | 0456136 | 11/1991 |
| EP | 0689817 | 1/1996 |
| EP | 689817 A2 * | 1/1996 |
| EP | 0689817 A2 * | 1/1996 |
| EP | 0 885 917 | 12/1998 |

(Continued)

OTHER PUBLICATIONS

Merriam Webster Online Dictionary, http://www.m-w.com/dictionary/granulate.*

(Continued)

*Primary Examiner* — Melanie Hand
(74) *Attorney, Agent, or Firm* — Roylance, Abrams, Berdo & Goodman, L.L.P.

(57) ABSTRACT

The present invention provides: an absorbent structure and an absorbent article, which are excellent in both liquid diffusion ability and liquid storage ability, and which are excellent in the dry feeling and the amount of wet back of the aqueous liquid, and which can realize the thinning and lightening more; and a water-absorbent resin fitly usable for the above absorbent structure and absorbent article. The absorbent structure, according to the present invention, comprises a liquid-diffusing member and a water-absorbent resin, with the absorbent structure being characterized in that when the capillary absorption index of the liquid-diffusing member at a height of 40 cm is referred to as A (A≧0.10), the capillary absorption index B of the water-absorbent resin at a height of 40 cm satisfies the following equation: B/A≧0.7 (equation 1).

8 Claims, 4 Drawing Sheets

FOREIGN PATENT DOCUMENTS

| | | |
|---|---|---|
| EP | 0 940 148 | 9/1999 |
| GB | 2 341 866 | 3/2000 |
| JP | 63-264971 | 11/1988 |
| JP | 5-261126 | 10/1993 |
| JP | 6-263881 | 9/1994 |
| JP | 8-52349 | 2/1996 |
| JP | 8-511973 | 12/1996 |
| JP | 8-511974 | 12/1996 |
| JP | 9-117470 | 5/1997 |
| JP | 11-503177 | 3/1999 |
| JP | 2000-463 | 1/2000 |
| JP | 2000-510365 | 8/2000 |
| JP | 2000-342963 | 12/2000 |
| JP | 2001-98170 | 4/2001 |
| JP | 2001-192464 | 7/2001 |
| JP | 2001-276124 | 10/2001 |
| JP | 2001-286505 | 10/2001 |
| JP | 2002-20408 | 1/2002 |
| WO | WO 88/01282 | 2/1988 |
| WO | WO 95/01146 | 1/1995 |
| WO | WO 95/01147 | 1/1995 |
| WO | WO 96/21681 | 7/1996 |
| WO | WO 97/45087 | 12/1997 |
| WO | WO 98/43573 | 10/1998 |
| WO | WO 99/47184 | 9/1999 |
| WO | WO 01/30290 | 5/2001 |
| WO | WO 01/30290 A1 * | 5/2001 |
| WO | WO 02/02648 | 1/2002 |

OTHER PUBLICATIONS

"Capillary Sorption Equilibria in Fiber Masses", Textile Research Journal, vol. 37, pp. 356-366 (1967).

Absorbency, Chatterjee, Textile, Science and Technology, vol. 7, 1985, pp. 60-62.

* cited by examiner

ABSORBENT STRUCTURE, ABSORBENT ARTICLE, WATER-ABSORBENT RESIN, AND ITS PRODUCTION PROCESS AND EVALUATION METHOD

TECHNICAL FIELD

The present invention relates to: an absorbent structure, an absorbent article, and a water-absorbent resin, which are fitly used for such as sanitary materials (e.g. disposable diapers, sanitary napkins, and so-called incontinent pads), dew-absorbent sheets, water-retaining materials for agricultural and horticultural fields, water-holding materials for building fields, medical materials (e.g. medical sheets), freshness-retaining materials for foods, and drip-absorbing materials for foods; and its production process and evaluation method.

BACKGROUND ART

At present, hydrophilic fibers (e.g. pulp) and water-absorbent resins which are water-swellable crosslinked polymers as obtained from such as an acrylic acid (salt) as a major raw material, are widely utilized as constituent materials of sanitary materials, such as disposable diapers, sanitary napkins, and so-called incontinent pads, for the purpose of causing them to absorb body fluids. In recent years, these sanitary materials such as disposable diapers, and sanitary napkins improve in high function and thinning. The amount of the water-absorbent resin as used per one sanitary material sheet and the weight ratio of the water-absorbent resin relative to the entire absorbent structure including such as the water-absorbent resin and the hydrophilic fiber tend to increase. In short, the ratio of the water-absorbent resin in the absorbent structure is increased by making the amount of the hydrophilic fiber having a small bulk density decrease, and by using the water-absorbent resin having excellent water absorbency and a large bulk density in a large amount. Thereby, the thinning of the sanitary material is attempted without lowering the water absorption quantity.

However, the above matter is a favorable course, from the viewpoint such that: the ratio of the hydrophilic fiber is lowered in such a manner; and the sanitary material in which the amount of the water-absorbent resin is increased simply stores a liquid, but on the contrary, it causes problems when the distribution and diffusion of the liquid are thought in a circumstance of practically using diapers. The water-absorbent resin in a large amount becomes a soft gel due to absorbing water. Therefore, caused is so-called gel blocking, which is a phenomenon such that the diffusion of liquids is greatly hindered. In order to avoid such a problem and to maintain the absorption performance of the absorbent structure, the ratio between the hydrophilic fiber and the water-absorbent resin is naturally limited, and the limitation of thinning the sanitary material is also caused.

In order to enhance the diffusion of the liquid in the absorbent structure and to use an absorbent material more efficiently, methods for distributing and diffusing a liquid, or liquid-diffusing members have hitherto been variously considered, and absorbent articles including these members have been variously known. Examples of these include: an absorbent pad in which a specific region of a hydrophilic fiber in an absorbent structure is compressed in a high density (U.S. Pat. No. 4,781,710); a liquid-distributing material having specific suction properties, which is obtained by molding and combining at least two kinds of fibers having different strength and specific surface area in a wet condition (WO 97/45087); a form-type absorbent material having continuous foam, which is produced by using a high-internal-phase emulsion (U.S. Pat. No. 5,387,207, U.S. Pat. No. 5,134,007, and U.S. Pat. No. 6,107,538); and an absorbent core, which favorably has a narrow crotch width including a form-type absorbent material having continuous foam and in which the absorption ability of the crotch region is not more than 40% of that of the entire absorption ability of the absorbent core (WO 98/43573 and JP-A-510365/2000).

In addition, members for acquiring liquids have been proposed in order to enhance liquid absorption efficiency and liquid retention of an absorbent article such as a disposable diaper. Known examples of such a liquid-acquiring member include: crosslinked cellulose (JP-A-264971/1988); and an exhaust-treating layer having a specific liquid permeation ratio index (JP-A-261126/1993).

However, it was made clear that: when the water-absorbent resin is used as a storing material in order to store the liquid as distributed and diffused by the above liquid-diffusing member, depending upon the liquid-diffusing member as used, the liquid therein is hardly transferred and absorbed to the water-absorbent resin, and the water-absorbent resin does not work efficiently as the liquid-storing member. It was made clear that: when especially a material having very high suction ability in the vertical direction, such as a porous polymer which is produced by using the high-internal-phase emulsion as mentioned above and has fine continuous foam therein, is used as the liquid-diffusing member, surprisingly, depending upon its properties, there are cases where the water-absorbent resin can hardly absorb the liquid from the above porous polymer and where the original storing function of the water-absorbent resin can hardly be displayed. Accordingly, even if the liquid can be diffused in the absorbent structure sufficiently, the function of storing it does not work favorably. Therefore, found was the phenomenon such that the leakage of the liquid from the absorbent article is caused with a far less capacity than an expected absorption quantity.

As to the arts to solve this problem, WO 99/47184 and U.S. Pat. No. 6,107,538 disclose a liquid-storing member having high capillary absorption ability, which is obtained by combining an absorbent material due to osmotic pressure (e.g. the above water-absorbent resin) with a material having a large surface area (e.g. a particulate porous-foam-type absorbent material which is produced by using the above high-internal-phase emulsion and has continuous foam, and a glass micro fiber).

However, according to this method, at least two materials as mentioned above are combined and used as the liquid-storing member. Therefore, a new apparatus for combining these materials in order to produce the liquid-storing material is necessary, and the steps are complicated, and besides, there is a problem such that the absorption ability of the water-absorbent resin is yet still in a low level even if there is a material having a large surface area around the water-absorbent resin. When the absorption ability of the material having a large surface area as used further is lower than that of the water-absorbent resin, there is also a problem of lowering the liquid absorption and storage ability of the entire liquid-storing member.

In addition, as is aforementioned, the liquid is rapidly captured into the absorbent structure in an initial state by making the liquid-acquiring member to exist. However, as the absorption quantity is increased, there were found cases where: since a certain time, the absorbent structure including such as the water-absorbent resin and the hydrophilic fiber cannot absorb the liquid in the liquid-acquiring member, and the absorption rate becomes slow conversely, and the amount of wet back of the aqueous liquid is increased.

In addition, as to even an absorbent article called as thin-type one at the present circumstances, the weight thereof is yet still heavy, and the thickness thereof is thick. Therefore, it is yet still unsatisfactory for such as circulation of goods, displaying space, purchase, and outdoor use, and further thinning is requested. Accordingly, when the concentration of the water-absorbent resin in the absorbent structure was further increased, for example, when the amount of the bulky hydrophilic fiber as used was decreased and a water-absorbent resin layer including the water-absorbent resin in a major proportion was tried and used as the liquid-storing member, there were cases where: the problem of the gel blocking of the water-absorbent resin as aforementioned draws attention more, and the objective absorption capacity cannot be realized.

Known examples of arts of using the water-absorbent resin layer including the water-absorbent resin in a major proportion as the liquid-storing member include: an absorbent core as equipped with a first structure and a second structure, wherein the first structure includes a first fiber material and a first super-absorbent material, and wherein the second structure includes a second fiber material and a second super-absorbent material of which the absorption rate is faster than that of the first super-absorbent material (JP-A-511973/1996); an absorbent structure having an upper constituted structure and a lower constituted structure having a special structure, wherein the upper constituted structure includes a liquid-capturing layer and a super-absorbent material layer that is comprised of a super-absorbent material having a gel layer permeation value of not less than a specific amount, and wherein the lower constituted structure includes an upper layer having an opening space for storing a liquid, and a lower layer storing a super-absorbent material layer of which the absorption capacity is in a specific range under a load (JP-A-511974/1996); an absorbent article including a first absorbent layer and a second absorbent layer, wherein the first absorbent layer in which a water-absorbent polymer is retained between nonwoven-fabric-made fibers, and wherein the second absorbent layer is comprised of a hydrophilic fiber aggregate, and wherein the first absorbent layer is located at the side of a liquid-permeable surface sheet (JP-A-286505/2001); and an absorbent structure, which is an absorbent structure including a humidable fiber and a surface-crosslinked water-absorbent resin and having no gel blocking property, wherein the weight ratio of the water-absorbent resin is in the range of 75 to 95 weight % relative to the, fiber and the above surface-crosslinked water-absorbent resin, and wherein the ratio of volume as increased is not less than 15% after 600 seconds under a load (WO 01/30290).

In these above JP-A-511973/1996 and JP-A-511974/1996, disclosed are the art relating to the constitution of the absorbent structure, in which the liquid-storing position in the absorbent structure is transferred from downward to upward. In JP-A-286505/2000, disclosed is the art in which the roughness of a back sheet in a diaper is removed. In WO 01/30290, disclosed is the art in which the opening ratio of the absorbent structure in a swollen state is defined. However, the distribution relationship of the liquid between the liquid-acquiring member and the water-absorbent resin layer that catch the liquid is not mentioned.

In addition, also filed was the art relating to a absorbent article for body fluids, in which the water-absorbent resin ratio is in the range of 10 to 90 weight % relative to the total amount of a pulp and a water-absorbent resin, wherein a water-absorbent polymer having specific performance for aspirating and sucking body fluids is used in order to transfer a liquid as retained in a pulp fiber space into the polymer (JP-A-276124/2001).

However, the polymer as used in this case is a polymer having a comparatively small bulk density and a high unshaping degree, and the so-called absorption rate of rapidly absorbing the liquid as retained in the pulp space around the polymer is regarded as an important matter, and similarly the distribution relationship of the liquid between the liquid-acquiring member and the water-absorbent resin layer is not disclosed.

DISCLOSURE OF THE INVENTION

Object of the Invention

Accordingly, in order to solve the above-mentioned problems, an object of the present invention is to provide: an absorbent structure and an absorbent article, in which, in the absorbent structure and the absorbent article comprising a liquid-diffusing member and a water-absorbent resin, a liquid is sufficiently transferred and absorbed from the liquid-diffusing member to the water-absorbent resin even if an auxiliary material such as a material having a large surface area is not used, namely which are excellent in both liquid diffusion ability and liquid storage ability; and a water-absorbent resin fitly usable for the above absorbent structure and absorbent article, and the object is to provide: an absorbent structure and an absorbent article, in which, in the absorbent structure and the absorbent article comprising a liquid-acquiring member and a water-absorbent resin, a liquid is favorably transferred from the liquid-acquiring member to the water-absorbent resin even if the concentration of the water-absorbent resin is raised more, and the liquid-acquiring function is not lowered so much even if the liquid is repeatedly absorbed, and which are excellent in the dry feeling and the amount of wet back of the aqueous liquid, and which can realize the thinning and lightening more; and a water-absorbent resin fitly usable for the above absorbent structure and absorbent article.

SUMMARY OF THE INVENTION

The present inventors diligently studied to achieve the above-mentioned objects. As a result, when they took note of the performance referred to as capillary absorption ability of a water-absorbent resin itself, which has been unknown as the ability of the water-absorbent resin hitherto, and when specific relationships as mentioned below were realized between the capillary absorption ability of the liquid-diffusing member or liquid-acquiring member and the that of the water-absorbent resin, they found out that even if other auxiliary suction material (e.g. a material having a large surface area as disclosed in the above WO 99/47184) is not used, the water-absorbent resin can favorably absorb the liquid from the liquid-diffusing member and can favorably absorb the liquid from the liquid-acquiring member. The capillary absorption ability, as is explained in detail blow, is measured by an apparatus of which the rough drawing is shown in FIG. 1, and is obtained by a process including the steps of arranging a measuring sample (water-absorbent resin) in a position higher than the liquid surface of a physiological saline in a liquid-storing receptacle by several tens centimeters; and measuring capillary absorption ability of sucking up a liquid against a negative pressure as caused by water column at the height. There has hitherto been an example of measuring absorption ability in a state of no negative pressure, namely, in a state where the height of the liquid surface in a liquid-storing receptacle is the same as that of the sample position (WO 88/01282). However, there has never been an example of measuring capillary absorption ability under such a negative pressure, and the relationship between the capillary absorption ability of a water-absorbent resin as measured by the method of the present invention and the performance of an absorbent structure has also never been known. Specifically, they found out that: if the absorbent structure and the absorbent article are produced by using the water-absorbent resin having performance such that the above relationships are maintained depending upon the properties of the liquid-diffusing member or liquid-acquiring member, the system as called the diffusion to the storage of the liquid in the absorbent structure, the acquirement to the storage, or the acquirement to the storage and diffusion favorably works; and the absorbent structure and the absorbent article displaying very excellent liquid absorption ability can be provided by a very simple production process. Then, the present invention has been completed.

Furthermore, they found out that when using a water-absorbent resin as a raw material powder wherein the water-absorbent resin has a weight-average particle diameter (as is mentioned below, the method for measuring a weight-average particle diameter of a water-absorbent resin in the present invention is determined by sieving, and the average particle diameter is on weight average of mesh diameters) in a specific range and displays a space ratio and an average space radius as to spaces between particles in specific ranges when the particles are made to absorb a liquid and saturation-swollen without load, and when using a dispersion of water-dispersible fine particles as a binder, a water-absorbent resin fine powder can be extremely efficiently granulated, and water-absorbent resin particles having strong adhesion and re-dispersibility and being fitly usable for the present invention absorbent structure and absorbent article are easily obtained and have excellent absorption properties. Then, the present invention has been completed.

That is to say, an absorbent structure, according to the present invention, comprises a liquid-diffusing member and a water-absorbent resin, with the absorbent structure being characterized in that when the capillary absorption index of the liquid-diffusing member at a height of 40 cm is referred to as A (A≧0.10), the capillary absorption index B of the water-absorbent resin at a height of 40 cm satisfies the following equation:

$$B/A \geqq 0.7 \quad \text{(equation 1)}$$

Another absorbent structure, according to the present invention, comprises a liquid-diffusing member and a water-absorbent resin, with the absorbent structure being characterized in that when the capillary absorption capacity of the liquid-diffusing member at a height of 40 cm is referred to as C (C≧2.0 (g/g)), the capillary absorption capacity D of the water-absorbent resin at a height of 40 cm satisfies the following equation:

$$D/C \geqq 0.7 \quad \text{(equation 2)}$$

Yet another absorbent structure, according to the present invention, comprises a liquid-diffusing member and a liquid-storing member, with the absorbent structure being characterized in that: a member displaying a suction height of not lower than 30 cm is used as the liquid-diffusing member; and a water-absorbent resin displaying a capillary absorption capacity D of not less than 15 (g/g) at a height of 40 cm is used as the liquid-storing member.

Yet another absorbent structure, according to the present invention, comprises a liquid-diffusing member and a liquid-storing member, with the absorbent structure being characterized in that: a member displaying a suction height of not lower than 30 cm is used as the liquid-diffusing member; and a surface-crosslinking-treated water-absorbent resin having a weight-average particle diameter of not larger than 250 µm is used as the liquid-storing member.

Yet another absorbent structure, according to the present invention, comprises a liquid-diffusing member and a water-absorbent resin including a crosslinked poly(acrylic acid (salt)) polymer in a major proportion, with the absorbent structure being characterized in that: the liquid-diffusing member is a porous polymer obtained by a process including the step of polymerizing a high-internal-phase emulsion; and the weight ratio of the water-absorbent resin is in the range of 75 to 90 weight % relative to the total weight of the liquid-diffusing member and the water-absorbent resin.

Yet another absorbent structure, according to the present invention, comprises a liquid-acquiring member and a water-absorbent resin layer having a scattering amount of not smaller than 250 g/m² of the water-absorbent resin, with the absorbent structure being characterized in that when the capillary absorption index of the liquid-acquiring member at a height of 40 cm is referred to as E (E<0.1), the capillary absorption index B of the water-absorbent resin at a height of 40 cm satisfies the following equation:

$$B/E \geqq 10 \quad \text{(equation 3)}$$

Yet another absorbent structure, according to the present invention, comprises a liquid-acquiring member and a water-absorbent resin layer having a scattering amount of not smaller than 250 g/m² of the water-absorbent resin, with the absorbent structure being characterized in that when the capillary absorption index of the liquid-acquiring member at a height of 40 cm is referred to as E (E<0.1), the capillary absorption index F of the water-absorbent resin layer at a height of 40 cm satisfies the following equation:

$$F/E \geqq 10 \quad \text{(equation 4)}$$

Yet another absorbent structure, according to the present invention, comprises a liquid-acquiring member and a water-absorbent resin layer having a scattering amount of not smaller than 250 g/m² of the water-absorbent resin, with the absorbent structure being characterized in that: the liquid-acquiring member displays a capillary absorption capacity G of not more than 1.0 (g/g) at a height of 40 cm; and a water-absorbent resin displaying a capillary absorption capacity D of not less than 5 (g/g) at a height of 40 cm is used as the water-absorbent resin.

Yet another absorbent structure, according to the present invention, comprises a liquid-acquiring member and a water-absorbent resin layer having a scattering amount of not smaller than 250 g/m² of the water-absorbent resin, with the absorbent structure being characterized in that: the liquid-acquiring member displays a capillary absorption capacity G of not more than 1.0 (g/g) at a height of 40 cm; and the water-absorbent resin layer displays a capillary absorption capacity H of not less than 5 (g/g) at a height of 40 cm.

An absorbent article, according to the present invention, comprises the absorbent structure according to the present invention.

Water-absorbent resin particles, according to the present invention, are obtained by a process including the step of granulating a water-absorbent resin having a weight-average particle diameter of 50 to 300 µm and displaying a space ratio of 30 to 50% and an average space radius of 80 to 150 µm as to spaces between particles when saturation-swollen with a physiological saline (a 0.9 weight % aqueous NaCl solution)

without load; with the water-absorbent resin particles being characterized by having a weight-average particle diameter as increased by not less than 50% of that before the granulating step.

Another water-absorbent resin particles, according to the present invention, comprise a crosslinked poly(acrylic acid (salt)) polymer in a major proportion and display a capillary absorption capacity D of not less than 25 (g/g) at a height of 40 cm.

A production process for water-absorbent resin particles, according to the present invention, is characterized by comprising the step of adding a dispersion of water-dispersible fine particles to a water-absorbent resin, thereby increasing the weight-average particle diameter of the water-absorbent resin by not less than 50%, wherein the water-absorbent resin has a weight-average particle diameter of 50 to 300 μm and displays a space ratio of 30 to 50% and an average space radius of 80 to 150 μm as to spaces between particles when saturation-swollen with a physiological saline (a 0.9 weight % aqueous NaCl solution) without load.

An absorbent article, according to the present invention, comprises the water-absorbent resin particles according to the present invention.

A water-absorbent resin, according to the present invention, comprises a crosslinked poly(acrylic acid (salt)) polymer in a major proportion and displays a capillary absorption capacity D of not less than 25 (g/g) at a height of 40 cm.

An absorbent article, according to the present invention, comprises the water-absorbent resin according to the present invention.

An evaluation method for a water-absorbent resin, according to the present invention, comprises the step of measuring an absorption capacity for a liquid as absorbed by the water-absorbent resin within a predetermined time in a state where the liquid-absorbing position height H1 is in a position higher than the liquid surface height H2 in a liquid-storing receptacle.

These and other objects and the advantages of the present invention will be more fully apparent from the following detailed disclosure.

Figure 1:
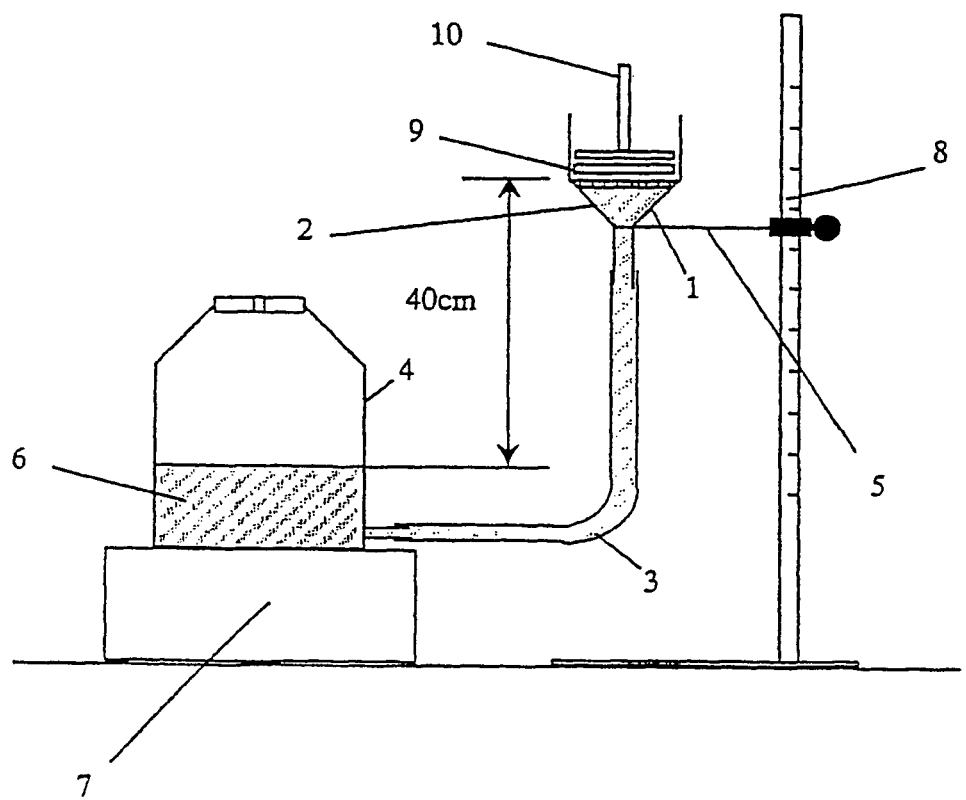
FIG. 1 is a schematic sectional view of a measurement apparatus as used for the measurement to determine the capillary absorption capacity and the capillary absorption index in the present invention. The capillary absorption capacity at a height of 40 cm is measured with this apparatus.

| (Explanation of the Symbols): | |
| --- | --- |
| 1: | Porous glass plate |
| 2: | Glass filter |
| 3: | Introducing tube |
| 4: | Liquid-storing receptacle |

| (Explanation of the Symbols): | |
| --- | --- |
| 5: | Supporting ring |
| 6: | Physiological saline |
| 7: | Balance |
| 8: | Stand |
| 9: | Measuring sample (water-absorbent resin or liquid-diffusing member) |
| 10: | Load (0.41 kPa (0.06 psi)) |
| 11: | Open-air-aspirating pipe |
| 12: | Introducing tube |
| 13: | Glass filter |
| 14: | Physiological saline |
| 15: | Liquid-storing receptacle |
| 16: | Balance |
| 17: | Filter paper |
| 18: | Wire net |
| 19: | Plastic cylinder |
| 10: | Load (0.41 kPa (0.06 psi)) |
| 20: | Load (2.07 kPa (0.3 psi)) |
| 21: | Load (4.83 kPa (0.7 psi)) |
| 31: | Liquid-permeable polyester nonwoven fabric |
| 32: | Water-absorbent resin |
| 33: | Liquid-diffusing member |
| 34: | Liquid-impermeable polyethylene film |
| 35: | Haetlon paper |
| 36: | Adhesive tape |

DETAILED DESCRIPTION OF THE INVENTION

[1] Capillary Absorption Ability:

The capillary absorption ability as used in the present invention is generally an evaluation item that has been used hitherto in order to evaluate the absorbency of a material (e.g. paper and pulp) sucking up and absorbing a liquid by capillary action. The liquid amount as absorbed per a unit weight of a sample is measured in a state where the liquid-absorbing position is changed to various heights by using an apparatus as mentioned below, and thereby evaluated are the capillary absorption capacity and liquid suction ability of the sample. A specific measurement method of the capillary absorption capacity meaning the capillary absorption ability in the present invention is disclosed in examples as mentioned below in detail. Measurement methods based on the same principle are also disclosed in such as: Textile Research Journal Vol. 37, 356 (1967), "Absorbency" (Chatterjee, Textile, Science and Technology, Vol. 7, 1985), JP-A-052349/1996, and WO 99/47184.

In an evaluation method for a water-absorbent resin in the present invention, comprising the step of measuring an absorption capacity for a liquid as absorbed by the water-absorbent resin within a predetermined time in a state where the liquid-absorbing position height H1 is in a position higher than the liquid surface height H2 in a liquid-storing receptacle, the above-mentioned method is applied first to the water-absorbent resin. From the resultant value, it is found that the liquid absorption ability of the water-absorbent resin from other base material such as a liquid-diffusing member or a liquid-acquiring member can be judged correctly. In order to raise the accuracy of measurement and the relationship with the performance of the absorbent structure, the measurement is carried out in a state where the height difference between the liquid-absorbing position height H1 and the liquid surface height H2 in the liquid-storing receptacle is favorably in the range of 20 to 60 cm, more favorably 30 to 50 cm As to the capillary absorption ability in the present invention, there are two kinds of a capillary absorption capacity and a capillary absorption index. As to the capillary absorption capacity in the present invention, measured is an amount (capacity) of a liquid as absorbed by a sample within 30 minutes in a state where there is a height difference between the liquid-absorbing position and the liquid surface in a liquid-storing receptacle. When the height difference between the liquid-absorbing position and the liquid surface in the liquid-storing receptacle is 40 cm, it is defined as "a capillary absorption capacity at a height of 40 cm", and when the height difference between the liquid-absorbing position and the liquid surface in the liquid-storing receptacle is 0 cm, it is defined as "a capillary absorption capacity at a height of 0 cm".

In addition, the capillary absorption index in the present invention can be calculated by dividing a value of the capillary absorption capacity (as absorbed by a sample within 30 minutes in a state where there is a height difference between the liquid-absorbing position and the liquid surface in the liquid-storing receptacle) by a value of the capillary absorption capacity at a height of 0 cm (as absorbed by the sample within 30 minutes when the height difference with the liquid surface in the liquid-storing receptacle is 0 cm). "The capillary absorption index at a height of 40 cm" is calculated by dividing a value of the "capillary absorption capacity at a height of 40 cm" (when the height difference between the liquid-absorbing position and the liquid surface in the liquid-storing receptacle is 40 cm) by the value of the "capillary absorption capacity at a height of 0 cm" (when the height difference with the liquid surface in the liquid-storing receptacle is 0 cm).

Water-absorbent resins, which are on a market at present and used for sanitary materials in a large amount, are crosslinked poly(acrylic acid (salt)) polymers of which the major raw material is an acrylic acid (salt). The mechanism of absorbing a liquid is not by capillary absorption such as pulp, but it is fundamentally derived from the osmotic pressure difference between an absorbed liquid and the polymer itself that is a polymer electrolyte. However, the ability of the water-absorbent resin to absorb a liquid from a liquid-diffusing member or liquid-acquiring member having excellent liquid suction ability in the vertical direction, wherein the liquid is kept in the above member, could not be expected at all from only the absorption properties generally known as the ability of the water-absorbent resin hitherto, such as absorption capacity, absorption rate, absorption capacity under a load, and liquid permeability of gel layer.

The present inventors took note of and considered the ability as called the capillary absorption ability even in the water-absorbent resin similar to the liquid-diffusing member or liquid-acquiring member. Then, they found out that: the capillary absorption ability is greatly different due to the kinds of water-absorbent resins; and further, by using a combination of a water-absorbent resin and a liquid-diffusing member or liquid-acquiring member wherein the water-absorbent resin has capillary absorption ability specifically in relation to the capillary absorption ability of the above liquid-diffusing member or liquid-acquiring member, the water-absorbent resin can favorably absorb and store a liquid from the liquid-diffusing member or liquid-acquiring member. Furthermore, they found out that: an absorbent structure as planed to maintain this relationship displays very excellent liquid absorption efficiency; and, in an absorbent article (e.g. disposable diaper) including such an absorbent structure, a water-absorbent resin is spread all over and used very effectively, and therefore the absorption ability of the entire diaper can be very greatly enhanced; and a thin-type easily-movable diaper including fewer members can be produced by adjusting this high absorption ability to absorption ability in a desirable practical level.

In order to cause the capillary absorption ability of the water-absorbent resin in the present invention, the balance between the capillary absorption ability and the absorption properties is thought to be very important, wherein the capillary absorption ability is derived from the physical shape of the water-absorbent resin and wherein the absorption properties are derived from the osmotic pressure of various polymers themselves as caused by carrying out surface-crosslinking treatment.

[2] Absorbent Structure Comprising Liquid-Diffusing Member and Water-Absorbent Resin:

(2-1) Relationship Between Capillary Absorption Ability of Liquid-Diffusing Member and that of Water-Absorbent Resin:

The relationship between the capillary absorption ability of the liquid-diffusing member and that of the water-absorbent resin in the present invention is explained.

The water-absorbent resin usable in the present invention is a water-absorbent resin wherein when the capillary absorption index of the liquid-diffusing member at a height of 40 cm is referred to as A ($A \geq 0.10$), the capillary absorption index B of the water-absorbent resin at a height of 40 cm satisfies the following equation:

$$B/A \geq 0.7 \qquad \text{(equation 1)}$$

The value of the capillary absorption index B of the water-absorbent resin necessary in the present invention at a height of 40 cm is different depending upon the property of the liquid-diffusing member as used, namely, the capillary absorption index A of the liquid-diffusing member as used at a height of 40 cm. If the relationship $B/A \geq 0.7$ above is satisfied, a liquid from the liquid-diffusing member to the water-absorbent resin is favorably distributed, and the water-absorbent resin can favorably absorb and store the liquid. In the case where the B/A is less than 0.7, there are cases where: the water-absorbent resin difficultly absorbs the liquid from the liquid-diffusing member; and the liquid distribution ratio from the liquid-diffusing member is lowered; and the absorption quantity of the water-absorbent resin is not improved even if diapers include these absorbent structures. Therefore, the water-absorbent resin does not favorably work as the liquid-storing member. The water-absorbent resin favorably satisfies $B/A \geq 1.3$, more favorably $B/A \geq 1.5$. In addition, in the case where the B/A is more than 2.0, there is a case where the liquid diffusion ratio of the liquid-diffusing member is lowered, and it is necessary to pay attention to this matter. Incidentally, hereinafter, the value of the B/A may be referred to as a liquid-diffusion-and-storage coefficient 1.

In addition, another water-absorbent resin usable in the present invention is water-absorbent wherein when the capillary absorption capacity of the liquid-diffusing member at a height of 40 cm is referred to as C ($C \geq 2.0$ (g/g)), the capillary absorption capacity D of the water-absorbent resin at a height of 40 cm satisfies the following equation:

$$D/C \geq 0.7 \qquad \text{(equation 2)}$$

The value of the capillary absorption capacity D of the water-absorbent resin necessary in the present invention at a height of 40 cm is different depending upon the property of the liquid-diffusing member as used, namely, the capillary absorption capacity C of the liquid-diffusing member as used at a height of 40 cm. Even if the relationship $D/C \geq 0.7$ above is satisfied, a liquid from the liquid-diffusing member to the water-absorbent resin is favorably distributed, and the water-absorbent resin can favorably absorb and store the liquid. In the case where the D/C is less than 0.7, the water-absorbent resin difficultly absorbs the liquid from the liquid-diffusing member, and then the water-absorbent resin does not favorably work as the liquid-storing member. The water-absorbent resin favorably satisfies D/C≧1.3, more favorably D/C≧1.5. In addition, in the case where the D/C is more than 10, there is a case where the liquid diffusion ratio of the liquid-diffusing member is lowered, and it is necessary to pay attention to this matter. Incidentally, hereinafter, the value of the D/C may be referred to as a liquid-diffusion-and-storage coefficient 2.

In the present invention, it is more favorable that both the liquid-diffusion-and-storage coefficient 1 and the liquid-diffusion-and-storage coefficient 2 as mentioned above satisfy the present invention range. When only the one coefficient satisfies the range, the liquid absorption ability of the water-absorbent resin from the liquid-diffusing member may not be displayed favorably due to a condition of use, and therefore it is necessary to pay attention to his matter.

In addition, the present invention relates to an absorbent structure comprising a liquid-diffusing member and a water-absorbent resin having a specific relationship, but the absorbent structure also works as a liquid-transfer-and-absorption system comprising a liquid-diffusing member and a water-absorbent resin having a specific relationship. That is to say, the present invention can also provide: a liquid-transfer-and-absorption system, which is an absorbent structure comprising a liquid-diffusing member and a water-absorbent resin, with the system being characterized in that when the capillary absorption index of the liquid-diffusing member at a height of 40 cm is referred to as A (A≧0.10), the capillary absorption index B of the water-absorbent resin at a height of 40 cm satisfies the following equation:

$$B/A \geqq 0.7 \quad \text{(Equation 1); and}$$

a liquid-transfer-and-absorption system, which is an absorbent structure comprising a liquid-diffusing member and a water-absorbent resin, with the system being characterized in that when the capillary absorption capacity of the liquid-diffusing member at a height of 40 cm is referred to as C (C≧2.0 (g/g)), the capillary absorption capacity D at a height of 40 cm satisfies the following equation:

$$D/C \geqq 0.7 \quad \text{(Equation 2)}$$

(2-2) Liquid-Diffusing Member:

The liquid-diffusing member usable in the present invention is defined as a material displaying a capillary absorption index A of not less than 0.10 at a height of 40 cm and a capillary absorption capacity C of not less than 2.0 (g/g) at a height of 40 cm, and substantially having no hydrogel-formability. The liquid-diffusing member is a material for diffusing a liquid as added to the absorbent structure or absorbent article having the absorbent structure, over a wider area in the absorbent structure. Particularly, even in a mode of practical use, in order to enable such a function to be displayed sufficiently, the liquid-diffusing member has a porous structure and excellent liquid suction ability in the vertical direction. In addition, the liquid-diffusing member itself more favorably has a predetermined level of ability of retaining, absorbing and storing a liquid.

The liquid-diffusing member usable in the present invention is a member having excellent liquid diffusion ability and liquid suction ability, and it is necessary that the capillary absorption index A is not less than 0.10 at a height of 40 cm. The capillary absorption index A of such as flap pulp as used for disposable diapers hitherto is not more than 0.05 at a height of 40 cm according to the measurement method in the present invention. In such a material displaying a capillary absorption index A is less than 0.10, the liquid suction ability in the vertical direction is small, and it is difficult to diffuse a liquid over the entire face of the liquid-diffusing member or the entire absorbent structure, and the material of the entire absorbent structure cannot be efficiently used. The capillary absorption index A is favorably not less than 0.20 at a height of 40 cm, more favorably not less than 0.30, most favorably not less than 0.40.

In addition, the liquid-diffusing member usable in the present invention favorably displays a capillary absorption capacity of not less than 10 (g/g) at a height of 0 cm. The higher the capillary absorption capacity is at a height of 0 cm, the larger the liquid-transferring capacity of the liquid-diffusing member is. Also from the viewpoint of absorbing, retaining and storing a liquid, it can function, and therefore an excellent absorbent structure can be obtained. The capillary absorption capacity is more favorably not less than 20 (g/g) at a height of 0 cm, still more favorably not less than 30 (g/g).

It is necessary that another liquid-diffusing member usable in the present invention displays a capillary absorption capacity C of not less than 2.0 (g/g) at a height of 40 cm. The capillary absorption capacity C of such as flap pulp as used for disposable diapers hitherto is not more than 1.0 (g/g) at a height of 40 cm. In such a material displaying a capillary absorption capacity C is less than 2.0 (g/g) at a height of 40 cm, the liquid suction ability in the vertical direction is small, and it is difficult to diffuse a liquid over the entire face of the liquid-diffusing member or the entire absorbent structure, and the material of the entire absorbent structure cannot be efficiently used. The capillary absorption capacity C is favorably not less than 5.0 (g/g) at a height of 40 cm, more favorably not less than 10.0 (gig).

In addition, similarly, another liquid-diffusing member usable in the present invention favorably displays a capillary absorption capacity of not less than 10 (g/g) at a height of 0 cm. The higher the capillary absorption capacity is at a height of 0 cm, the larger the liquid-transferring capacity of the liquid-diffusing member is. Also from the viewpoint of absorbing, retaining and storing a liquid, it can function, and therefore an excellent absorbent structure can be obtained. The capillary absorption capacity is more favorably not less than 20 (g/g) at a height of 0 cm, still more favorably not less than 30 (g/g).

The liquid-diffusing member usable in the present invention satisfies the above conditions, and is used together with a water-absorbent resin, and thereby they are used as an absorbent structure.

As to the relationship between both of them, as is aforementioned, it is necessary that: when the capillary absorption index of the liquid-diffusing member at a height of 40 cm is referred to as A, the capillary absorption index B of the above water-absorbent resin at a height of 40 cm satisfies B/A≧0.7, favorably B/A≧1.3; or when the capillary absorption capacity of the liquid-diffusing member at a height of 40 cm is referred to as C (C≧2.0 (g/g)), the capillary absorption capacity D of the above water-absorbent resin at a height of 40 cm satisfies D/C≧0.7, favorably D/C≧1.3. In addition, both of them more favorably satisfy the B/A≧0.7 and D/C≧0.7 at the same time, still more favorably the B/A≧1.3 and D/C≧1.3 at the same time.

In addition, the liquid-diffusing member usable in the present invention favorably displays a suction height of not lower than 30 cm, more favorably not lower than 40 cm, still more favorably not lower than 50 cm, wherein the suction height is ability of sucking up a liquid in the vertical direction as mentioned below. In the case where the suction height is not higher than 30 cm, the liquid diffusion ratio of the absorbent structure is low, and the entire absorbent structure cannot be utilized effectively.

The shape of the liquid-diffusing member can be a sheet, fibrous, particulate, or strip shape, but it is favorably a sheet shape in general. Then, the weight of the liquid-diffusing member per its unit area is in the range of about 50 to about 500 g/m$^2$, about 100 to about 200 g/m$^2$.

In addition, when the liquid-diffusing member has a difference of density, a slope of density, a difference of diffusion ability, and a slope of diffusion ability in the member, or when a second liquid-diffusing member not satisfying the present invention relationship is further used, it is favorable to make the capillary absorption ability of a portion of the liquid-diffusing member much closer to the water-absorbent resin satisfy the above relationship.

Examples of such a liquid-diffusing member include: porous polymers obtained by a process including the step of polymerizing a high-internal-phase emulsion (HIPE); fibrous materials having a predetermined density (e.g. cellulose pulps or nonwoven fabrics); and foam materials (e.g. urethane sponges and cellulose sponges). The liquid-diffusing member is favorably a member having excellent liquid suction ability, suction amount, and suction rate in the vertical direction. Among these, the porous polymers obtained by a process including the step of polymerizing a high-internal-phase emulsion (HIPE) as explained below are favorable.

a. Liquid-Diffusing Member Including Porous Polymers Obtained by a Process Including the Step of Polymerizing a High-Internal-Phase Emulsion (HIPE):

The porous polymer fitly usable as the liquid-diffusing member in the present invention can be obtained by a process including the step of polymerizing a high-internal-phase emulsion (HIPE), where the ratio of the water phase and the oil phase (W/O ratio) is not less than about 3/1 wherein the water phase is a dispersible (inner) phase and the oil phase is an outer phase. The method for producing the porous polymer from the HIPE is, for example, described in such as U.S. Pat. No. 5,189,070, U.S. Pat. No. 5,250,576, U.S. Pat. No. 5,252,619, U.S. Pat. No. 5,290,820, U.S. Pat. No. 5,358,974, U.S. Pat. No. 5,252,619, U.S. Pat. No. 5,670,101, and U.S. Pat. No. 6,204,298. The porous polymer as obtained in this way is in a state of low-density foam including continuous foam having a fine diameter. If conditions are selected, the polymer foam having desirable absorption properties (e.g. very excellent liquid diffusion and suction properties) can be produced.

The raw material of the HIPE as used includes: an oil phase containing a polymerizable monomer component and a surfactant; and a water phase containing water. Examples of the polymerizable monomer component include: a polymerizable monomer having one polymerizable unsaturated group in its molecule wherein the monomer can form a crosslinked structure by polymerization; and/or a crosslinkable monomer having at least two polymerizable unsaturated groups in its molecule. Furthermore, if necessary, polymerization initiators, salts, and other additives may also be included as arbitrary components that are comprised in the oil phase and/or water phase.

As to the polymerizable monomer, at least one portion thereof favorably includes a (meth)acrylate ester. Specific examples thereof include: arylene monomers, such as styrene; monoalkylene arylene monomers, such as styrene, ethylstyrene, α-methylstyrene, vinyltoluene, and vinylethylbenzene; (meth)acrylate esters, such as methyl (meth)acrylate, ethyl (meth)acrylate, butyl (meth)acrylate, isobutyl (meth) acrylate, isodecyl (meth)acrylate, 2-ethylhexyl (meth)acrylate, lauryl (meth)acrylate, stearyl (meth)acrylate, cyclohexyl (meth)acrylate, and benzyl (meth)acrylate; chlorine-containing monomers, such as vinyl chloride, vinylidene chloride, and chloromethylstyrene; acrylonitrile compounds, such as acrylonitrile, and methacrylonitrile; and other monomers, such as vinyl acetate, vinyl propionate, N-octadecyl acrylamide, ethylene, propylene, and butene. These may be used either alone respectively or in combinations with each other.

The above crosslinkable monomer may be a compound having at least two polymerizable unsaturated groups in its molecule, or a compound that can form a crosslinked structure by polymerization. There is no especial limitation on the crosslinkable monomer if it is polymerizable in a dispersible emulsion or water-drop-in-oil-type high-dispersible-phase emulsion in the same way as of the above polymerizable monomer. Specific examples of the crosslinkable monomer include: aromatic monomers, such as divinylbenzene, trivinylbenzene, divinyltoluene, divinylxylene, p-ethyl-vinylbenzene, divinylnaphthalene, divinylalkylbenzenes, divinylphenathrene, divinylbiphenyl, divinyldiphenylmethane, divinylbenzyl, divinyl phenyl ether, and divinyl phenyl sulfide; oxygen-containing monomers such as divinylfuran; sulfur-containing monomers, such as divinyl sulfide and divinyl sulfone; aliphatic monomers, such as butadiene, isoprene, and pentadiene; ethylene glycol di(meth)acrylate, diethylene glycol di(meth)acrylate, triethylene glycol di(meth)acrylate, polyethylene glycol di(meth)acrylate, 1,3-butanediol di(meth)acrylate, 1,4-butanediol di(meth)acrylate, 1,6-hexanediol di(meth)acrylate, octanediol di(meth)acrylate, decanediol di(meth)acrylate, trimethylolpropane di(meth) acrylate, trimethylolpropane tri(meth)acrylate, pentaeryhritol di(meth)acrylate, pentaeryhritol tri(meth)acrylate, pentaerythritol tetra(meth)acrylate, dipentaerythritol di(meth) acrylate, dipentaerythritol tri(meth)acrylate, dipentaerythritol tetra(meth)acrylate, N, N'-methylenebis (meth)acrylamide, triallyl isocyanurate, triallylamine, tetraallyloxyethane, and ester compounds between polyhydric alcohols (e.g. hydroquinone, catechol, resorcinol, and sorbitol) and acrylic or methacrylic acid. These may be used either alone respectively or in combinations with each other.

The amount of the above crosslinkable monomer as used is favorably in the range of 0.1 to 90 weight %, more favorably 1 to 70 weight %, particularly favorably 5 to 50 weight %, of the weight of the entire polymerizable monomer component including the above polymerizable monomer and the above crosslinkable monomer.

In addition, there is no especial limitation on the surfactant as used in the oil phase if it can emulsify the water phase. Such as nonionic surfactants, cationic surfactants, anionic surfactants, and amphoteric surfactants that are publicly known hitherto can be used. Of the above, there is a case where the stability of the HIPE is improved when the nonionic surfactants are used together with the cationic surfactants.

The amount of the above surfactant as used is favorably in the range of 1 to 30 parts by weight, more favorably 3 to 15 parts by weight, per 100 parts by weight of the entire polymerizable monomer component including the polymerizable monomer and the crosslinkable monomer.

As to the above water, tap water, pure water, deionized water, and besides wasted water as obtained by producing the porous polymer can be used exactly or after carrying out definite treatment. The amount of the above water as used can be fitly selected due to desirable liquid distribution performance. Specifically, the porous ratio of the porous polymer is determined by changing the ratio of water phase/oil phase (W/O) of the HIPE. Therefore, the amount of the water as used is naturally determined if the W/O ratio is selected so that the porous ratio will accord with the aim.

The polymerization initiators may be initiators usable in ordinary polymerization, and any of water-soluble polymerization initiators (e.g. azo compounds such as 2,2'-azobis(2- amidinopropane) dihydrochloride; persulfate salts, such as ammonium persulfate, potassium persulfate, and sodium persulfate; peroxides, such as potassium peracetate, sodium peracetate, potassium percarbonate, and sodium percarbonate) and oil-soluble polymerization initiators can be used. Furthermore, a redox polymerization initiator system as obtained by combining the above polymerization initiator and a reductant may be used. In this case, as to the polymerization initiator, any of the water-soluble initiator or the oil-soluble initiator can be used, and the water-soluble redox polymerization initiator system may be used together with the oil-soluble redox polymerization initiator system.

The salts may be used if it is necessary to improve the stability of the HIPE. Specific examples of the salts include water-soluble salts such as halides, sulfate salts, and nitrate salts of alkaline or alkaline earth metals (e.g. calcium chloride, sodium sulfate, sodium chloride, and magnesium sulfate). These salts may be used either alone respectively or in combinations with each other. These salts are favorably added to the water phase. Of the above, multivalent metal salts are favorable in view of the stability of the HLPE when the polymerization is carried out.

The amount of such salts as used is favorably in the range of 0.1 to 20 parts by weight, more favorably 0.5 to 10 parts by weight, per 100 parts by weight of the water.

Furthermore, if the performance and function of other various additives are added and thereby they lead to improve the performance of the porous polymer as the liquid-diffusing member, such other various additives may fitly be used. For example, bases and/or buffers may be added in order to adjust a pH. Examples of such additives include active carbon, inorganic powders, organic powders, metal powders, deodorants, antimicrobial agents, anti-molding agents, perfumes, various polymers, and surfactants.

There is no especial limitation on the emulsification method of the HIPE usable in the present invention. For example, a uniform oil phase is prepared by stirring an oil-phase constituent component at a definite temperature wherein the component includes such as the polymerizable monomer component and surfactant, and the polymerization initiator and other additives that can be further added thereto if necessary. On the other hand, a uniform water phase is prepared by: stirring water with an objective amount as used while a water-phase constituent component is further added to the water wherein the component includes such as the polymerization initiators, salts, and other additives that can be further added thereto if necessary; and heating them at a predetermined temperature of the HIPE. Subsequently, the HIPE can stably be prepared by: combining the oil phase and the water phase, wherein the oil phase is a mixture of such as a polymerizable monomer component and surfactant, and the water phase is a mixture of such as water and a water-soluble salt as prepared in the above way; efficiently mix-stirring them at an emulsifying temperature of the HIPE to apply the optimum shearing stress; and then emulsifying them.

The ratio of water phase/oil phase (W/O) (weight ratio) can fitly be selected and is not especially limited. The ratio may be not less than 3/1 as defined before, but it is favorably in the range of 10/1 to 250/1, particularly favorably 10/1 to 100/1. The porous ratio of the porous polymer is determined by changing the W/o ratio, and thereby the liquid distribution ability, liquid suction ability, and liquid-retaining ability of the liquid-diffusing member can be changed. Therefore, when the liquid-diffusing member as an object of the present invention is produced, the W/O ratio is in the range of about 10/1 to about 100/1, more favorably about 20/1 to about 80/1.

There is no especial limitation on production apparatuses of the above HIPE. Examples of the hitherto known production apparatuses include stirrers having such as a propeller-type, paddle-type, and turbine-type blade, homomixers, pin mixers, line mixers, and static mixers. These may be used either alone respectively or in combinations with each other.

The emulsifying temperature of the HIPE in the emulsifying step in which the HIPE is formed is usually in the range of 40 to 110° C.

The HIPE as obtained by mixing the polymerization initiator is formed in a desirable mode. The molding shape is favorably a sheet shape in order to use the porous polymer as the liquid-diffusing member wherein the porous polymer is obtained in the present invention, but the HIPE is added to a cylindrical container to polymerize it and thereafter the resultant polymer may be cut into a sheet shape, or porous polymers having various modes (e.g. particulate, fibrous, and film shape) may be processed to a mode having liquid distribution ability as an end product. When the mode is a sheet shape, the thickness thereof is not limited, but the thickness as the mode of the end product is favorably not more than about 10 mm, more favorably not more than about 5 mm, still more favorably not more than about 3 mm, particularly favorably not more than about 1 mm, most favorably not more than about 0.5 mm. In the case where the thickness is considerably thick, the attachment feeling may be lowered when it is used as a liquid-diffusing member for absorbent articles.

There is no especial limitation on the method for polymerizing the HIPE, and hitherto known methods for polymerizing the HIPE can fitly be used. The HIPE is usually polymerized by heating with a static polymerization method under a condition that the structure in the HIPE is not destroyed. In this case, the batchwise polymerization in which this HIPE is polymerized every batch, or the continuous polymerization in which this HIPE is continuously polymerized by casting, for example, while feeding it into a heating zone may be carried out. The above polymerization temperature is usually in the range of 40 to 110° C. However, when the productivity is considered, the above polymerization temperature is favorably higher (e.g. favorably in the range of about 60 to about 110° C., more favorably about 80 to about 105° C.). The polymerization time is favorably in the range of several tens seconds to 30 minutes in order to obtain a porous polymer having uniform properties in view of the productivity. These detailed production methods are disclosed in such as Japanese Patent Application No. 203744/2000.

The porous polymer as obtained after the polymerization is usually dehydrated by compression, aspiration under reduced pressure, or a combination of these, and the polymer can be pressed in a mode such that the polymer is compressed to one half or third of the original thickness depending upon the its kind. For the purpose of such as further improving surface conditions of the porous polymer, the porous polymer may be washed in an aqueous solution or a solvent including pure water and an arbitrary additive, or thereafter if necessary, the polymer may be heat-dried by such as hot air, infrared ray, microwave. In addition, the water content of the resultant polymer may be adjusted by adding humidity. Furthermore, the polymer is cut to obtain a desirable shape and size for using as an end product, and then it may be processed to obtain a product in accordance with various uses.

b. Other Liquid-Diffusing Member:

Examples of other liquid-diffusing member usable in the present invention include: foaming structures including synthetic polymers, such as polyurethanes polystyrene, polyethylene, polypropylene, polyesters, poly(vinyl alcohol), butadiene-styrene rubbers (SBR), and nitrile-butadiene rubbers;

fibrous aggregates as obtained by adhering to or combining with synthetic fibers, such as polyethylene, polypropylene, polyethylene terephthalate, and nylon; rayon fibers; and fibrous aggregates as obtained by adhering to under a pressure, adhering to, or combining with hydrophilic fibers, such as cellulose fibers (e.g. celluloses, cellulose acetate, and nitro cellulose), and polyamide fibers. The shape thereof can be a sheet, fibrous, or particulate shape, but it is favorably a sheet shape in general. Favorable are the fibrous aggregates as obtained by adhering to under a pressure, adhering to, or combining with hydrophilic fibers, such as cellulose fibers and rayon fibers. These liquid-diffusing members may be produced in a line when absorbent structures and absorbent articles are produced.

The necessary performance of the liquid-diffusing member in the present invention as shown in these a. and b. is mentioned above.

(2-3) Water-Absorbent Resin:

The present invention water-absorbent resin is a hydrophilic crosslinked polymer, namely a polymer (water-swellable water-insoluble hydrogel-formable polymer) having a property such that: when an aqueous liquid contact is in contact with such as a particulate polymer aforementioned, the above polymer particles are swollen by absorbing the above liquid in the particles, and a hydrogel including the aqueous liquid can be formed. In addition, the water-absorbent resin may include a mixture as obtained by adding an additive to the water-swellable water-insoluble hydrogel-formable polymer, wherein the amount of the additive is not more than 30 weight % relative to the total amount of the above water-swellable water-insoluble hydrogel-formable polymer and the above additive.

Water-absorbent resins have hitherto been used as materials absorbing liquids due to the osmotic pressure difference between the inside and the outside of the resins, namely as liquid-storing members such as disposable diapers. However, the present inventors took note of that: even if the properties of the water-absorbent resins as known hitherto (e.g. absorption capacity, absorption capacity under a load) are identical, the absorbing behaviors are greatly different due to the kinds of resins when liquids are absorbed from such as the liquid-diffusing member. Then, the present inventors diligently considered and found out that: the capillary absorption ability is greatly different even in a water-absorbent resin itself; and the water-absorbent resin can receive and store a liquid from the liquid-diffusing member more favorably when the relationship between the capillary absorption ability of the liquid-diffusing member and the capillary absorption ability of the water-absorbent resin satisfies a specific condition.

The water-absorbent resin usable in the present invention is a water-absorbent resin, in which, as is mentioned above, when the capillary absorption index of the liquid-diffusing member at a height of 40 cm is referred to as A ($A \geq 0.10$), the capillary absorption index B of the above water-absorbent resin at a height of 40 cm satisfies $B/A \geq 0.7$, favorably $B/A \geq 1.3$, more favorably $B/A \geq 1.40$.

The value of the capillary absorption index B of the water-absorbent resin necessary in the present invention at a height of 40 cm is different depending upon the property of the liquid-diffusing member as used, namely, the capillary absorption index A of the liquid-diffusing member as used at a height of 40 cm. If the above relationship $B/A \geq 0.7$ is satisfied, a liquid from the liquid-diffusing member to the water-absorbent resin is favorably distributed, and the water-absorbent resin can favorably absorb and store the liquid. The water-absorbent resin displays a capillary absorption index B of not less than 0.4 at a height of 40 cm, favorably not less than 0.5, more favorably not less than 0.6.

In addition, the water-absorbent resin as used in the present invention favorably displays a capillary absorption capacity of not less than 30 (g/g) at a height of 0 cm. If the capillary absorption capacity at a height of 0 cm is higher, the water-absorbent resin can retain a large amount of liquid as sucked up from the liquid-diffusing member. Therefore, an excellent absorbent structure is obtained from the viewpoint of the liquid absorption ability. The water-absorbent resin favorably displays a capillary absorption capacity of not less than 40 (g/g) at a height of 0 cm, more favorably not less than 50 (g/g).

In addition, another water-absorbent resin usable in the present invention is a water-absorbent resin, in which, when the capillary absorption capacity of the liquid-diffusing member at a height of 40 cm is referred to as C ($C \geq 2.0$ (g/g)), the capillary absorption capacity D of the above water-absorbent resin at a height of 40 cm satisfies $D/C \geq 0.7$, favorably $D/C \geq 1.3$, more favorably $D/C \geq 1.40$.

The value of the capillary absorption capacity D of another water-absorbent resin necessary in the present invention at a height of 40 cm is different depending upon the property of the liquid-diffusing member as used, namely, the capillary absorption capacity C of the liquid-diffusing member as used at a height of 40 cm. Even if the above relationship $D/C \geq 0.7$ is satisfied, a liquid from the liquid-diffusing member to the water-absorbent resin is favorably distributed, and the water-absorbent resin can favorably absorb and store the liquid. The water-absorbent resin favorably displays a capillary absorption capacity D of not less than 15 (g/g) at a height of 40 cm, more favorably not less than 20 (gig), still more favorably not less than 25 (g/g), most favorably not less than 30 (gig).

In addition, similarly, the water-absorbent resin as used in the present invention favorably displays a capillary absorption capacity of not less than 30 (g/g) at a height of 0 cm. If the capillary absorption capacity at a height of 0 cm is higher, the water-absorbent resin can retain a large amount of liquid as sucked up from the liquid-diffusing member. Therefore, an excellent absorbent structure is obtained from the viewpoint of the liquid absorption ability. The water-absorbent resin favorably displays a capillary absorption capacity of not less than 40 (g/g) at a height of 0 cm, more favorably not less than 50 (g/g).

In addition, when the water-absorbent resin as used in the present invention displays an absorption capacity of 20 to 50 g/g under a load of 2.07 kPa (0.3 psi), there are advantages in that the absorbency can favorably be maintained even if the absorbent structure is in a pressurized state. The water-absorbent resin more favorably displays an absorption capacity of 25 to 40 g/g.

The water-absorbent resin usable in the present invention satisfies the above conditions, and is used together with a liquid-diffusing member, and thereby they are used as an absorbent structure.

The shape of the water-absorbent resin can be a particulate, fibrous, sheet, or strip shape, but it is favorably a particulate shape in general. The water-absorbent resin is favorably a particulate resin, of which the raw material is an acrylic acid (salt) in a major proportion, and of which the weight-average particle diameter of the fundamental particles is not larger than 250 μm, and the water-absorbent resin favorably has narrow particle diameter distribution. In addition, as to the production method thereof, aqueous solution polymerization or reversed-phase suspension polymerization can be carried out, but the water-absorbent resin is favorably a resin obtained by the reversed-phase suspension polymerization. In addition, in view of handling, the water-absorbent resin comprised of the fundamental particles is granulated while the capillary absorption ability of the present invention is maintained, and the weight-average particle diameter may be outside of the above range.

In the present invention, a water-absorbent resin satisfying the above relationship and a water-absorbent resin not satisfying the above relationship may be used together as the water-absorbent resin, but only the water-absorbent resin satisfying the above relationship is favorably used in order to display the present invention effect to the maximum. In addition, the resin is favorably arranged so that the capillary absorption ability of a portion of the water-absorbent resin will satisfy the above relationship, wherein the portion is much closer to the liquid-diffusing member.

Examples of the water-absorbent resin usable in the present invention include water-swellable crosslinked polymers that can be obtained by polymerizing hydrophilic monomers. Of the above, crosslinked poly(acrylic acid (salt)) polymers of which the major component is derived from acrylic acid or its salt are favorable. Specific examples thereof include: partially-neutralized crosslinked poly(acrylic acid) polymers (e.g. U.S. Pat. No. 4,625,001, U.S. Pat. No. 4,654,039, U.S. Pat. No. 5,250,640, U.S. Pat. No. 5,275,773, and EP 456136); crosslinked partially-neutralized graft polymers of starch-acrylic acid (U.S. Pat. No. 4,076,663); copolymers of isobutylene-maleic acid (U.S. Pat. No. 4,389,513); saponified copolymers of vinyl acetate-acrylic acid (U.S. Pat. No. 4,124,748); hydrolyzed (co)polymers of acrylamide (U.S. Pat. No. 3,959,569); and hydrolyzed polymers of acrylonitrile (U.S. Pat. No. 3,935,099). As to the crosslinked poly(acrylic acid (salt)) polymers, the acid group in the polymers is favorably neutralized in a ratio of 50 to 90 mol %, and examples of the salt include alkaline metal salts, ammonium salts, and amine salts.

The water-absorbent resin usable in the present invention, particularly the crosslinked poly(acrylic acid (salt)) polymer as favorably used, may be obtained by copolymerizing monomers as used in a major proportion (e.g. acrylic acid or its salt), and besides, other monomers together if necessary. Examples of other monomers include: anionic unsaturated monomers, such as methacrylic acid, maleic acid, vinylsulfonic acid, styrenesulfonic acid, 2-(meth)acrylamido-2-methylpropanesulfonic acid, 2-(meth)acryloylethanesulfonic acid, and 2-(meth)acryloylpropanesulfonic acid, and salts thereof; nonionic hydrophilic-group-containing unsaturated monomers, such as acrylamide, methacrylamide, N-ethyl (meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth) acrylate, methoxypolyethylene glycol (meth)acrylate, polyethylene glycol mono(meth)acrylate, vinylpyridine, N-vinylpyrrolidone, N-acryloylpiperidine, and N-acryloylpyrrolidine; and cationic unsaturated monomers, such as N,N-dimethylaminoethyl (meth)acrylate, N,N-diethylaminoethyl (meth)acrylate, N,N-dimethylaminopropyl (meth)acrylate, and N,N-dimethylaminopropyl(meth)acrylamide, and quaternary salts thereof. The amount of the other monomers other than the acrylic acid as used is favorably in the range of 0 to 30 mol %, more favorably 0 to 10 mol %, relative to the entire monomer.

Examples of the method for introducing a crosslinked structure into the water-absorbent resin as used in the present invention include: a self-crosslinking-type method in which no crosslinking agent is used; and a method which involves copolymerizing or reacting with an internal-crosslinking agent having at least two polymerizable unsaturated groups or at least two reactive groups. Favorable is the method involving copolymerizing or reacting with the internal-crosslinking agent.

Specific examples of these internal-crosslinking agents include: N,N'-methylenebis(meth)acrylamide, (poly)ethylene glycol di(meth)acrylate, (poly)propylene glycol di(meth) acrylate, trimethylolpropane tri(meth)acrylate, trimethylolpropane di(meth)acrylate, glycerol tri(meth)acrylate, glycerol acrylate methacrylate, ethylene-oxide-modified trimethylolpropane tri(meth)acrylate, pentaerythritol tetra (meth)acrylate, dipentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, polyethylenimine, and glycidyl (meth)acrylate. In addition, these internal-crosslinking agents may be used in combinations with each other. Of the above, from the viewpoint of the absorption performance of the water-absorbent resin as obtained, it is favorable that the compound having at least two polymerizable unsaturated groups is essentially used. The amount as used is favorably in the range of 0.005 to 3 mol %, more favorably 0.01 to 1.5 mol %, of the aforementioned monomer component.

Incidentally, when the above polymerization is carried out, hydrophilic polymers (e.g. starch-cellulose, derivatives from starch-cellulose; polyvinyl alcohol, polyacrylic acid (salts), and crosslinked products of polyacrylic acid (salts)) and chain transfer agents (e.g. hypophosphorous acid (salts)) may be added.

When the above monomer including acrylic acid or its salt in a major proportion is polymerized in order to obtain the water-absorbent resin as used in the present invention, bulk polymerization or precipitation polymerization can be carried out. However, from the viewpoint of the performance or the easiness of controlling the polymerization, aqueous solution polymerization or reversed-phase suspension polymerization is favorably carried out by using the above monomer in the form of its aqueous solution. The above polymerization method is publicly known hitherto and disclosed in such as U.S. Pat. No. 4,625,001, U.S. Pat. No. 4,769,427, U.S. Pat. No. 4,873,299, U.S. Pat. No. 4,093,776, U.S. Pat. No. 4,367, 323, U.S. Pat. No. 4,446,261, U.S. Pat. No. 4,683,274, U.S. Pat. No. 4,690,996, U.S. Pat. No. 4,721,647, U.S. Pat. No. 4,738,867, and U.S. Pat. No. 4,748,076.

In addition, when the polymerization is carried out, radical polymerization initiators (e.g. potassium persulfate, ammonium persulfate, sodium persulfate, t-butyl hydroperoxide, hydrogen peroxide, and 2,2'-azobis(2-amidinopropane) dihydrochloride), and active energy rays (e.g. ultraviolet rays and electron beams) can be used. In addition, when acidic radical polymerization initiators are used, reductants (e.g. sodium sulfite, sodium hydrogensulfite, ferrous sulfate, and L-ascorbic acid) may be used together to carry out redox polymerization. The amount of these polymerization initiators as used is usually in the range of 0.001 to 2 mol %, favorably 0.01 to 0.5 mol %.

The particle shape of the water-absorbent resin as obtained by the above polymerization is generally such as irregular pulverized, spherical, fibrous, bar, almost spherical, or flat shape.

In order to obtain the water-absorbent resin as used in the present invention wherein the water-absorbent resin displays an excellent capillary absorption index and a capillary absorption capacity at a height of 40 cm, its particle surface is favorably crosslinked with a surface-crosslinking agent.

Examples of the surface-crosslinking agent usable for surface-crosslinking the water-absorbent resin include: polyhydric alcohol compounds, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol; epoxy compounds, such as ethylene glycol diglycidyl ether, polyethylene diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyamine compounds, such as ethylenediamine, diethylenetriamine, triethylenetetraamine, tetraethylenepentaamine, pentaethylenehexamine and polyethylenimine, and their inorganic or organic salts (e.g. azetidinium salts); polyisocyanate compounds, such as 2,4-tolylene diisocyanate and hexamethylene diisocyanate; polyoxazoline compounds, such as 1,2-ethylenebisoxazoline; alkylene carbonate compounds, such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, and 1,3-dioxopan-2-one; haloepoxy compounds, such as epichlorohydrin, epibromohydrin and α-methylepichlorolhydrin, and their polyamine adducts (for example, Kymene made by Hercules: registered trademark); silane coupling agents, such as γ-glycidoxypropyltrimethoxysilane, and γ-aminopropyltriethoxysilane; and polyvalent metallic compounds, such as hydroxides and chlorides of zinc, calcium, magnesium, aluminum, iron, and zirconium.

Of the above, the surface-crosslinking agent favorably includes a combination of surface-crosslinking agents of which the solubility parameters are different each other. The surface-crosslinking agent favorably includes a combination of: a first surface-crosslinking agent having a solubility parameter of not less than 25.6 $[(J/cm^3)^{1/2}]$ (12.5 $[(cal/cm^3)^{1/2}]$); and a second surface-crosslinking agent having a solubility parameter of less than 25.6 $[(J/cm^3)^{1/2}]$ (12.5 $[(cal/cm^3)^{1/2}]$). The solubility parameter of the surface-crosslinking agent is disclosed in such as U.S. Pat. No. 5,422,405.

The amount of the surface-crosslinking agent as used is favorably in the range of about 0.001 to about 5 parts by weight per 100 parts by weight of the water-absorbent resin. In the case where the amount is larger than 5 parts by weight or smaller than 0.001 part by weight, there is a case where it is difficult to obtain the surface-crosslinked layer in the range of the present invention.

Water may be used when the present invention surface-crosslinking agent is blended with the water-absorbent resin. The amount of water as used is also generally in the range of 0.5 to 10 parts by weight (excluding 0.5 part by weight), favorably 1 to 5 parts by weight, per 100 parts by weight of the water-absorbent resin in terms of solid content.

In addition, when the surface-crosslinking agent or its aqueous solution is blended, hydrophilic organic solvents or a third substance may be used. When the hydrophilic organic solvents are used, examples of the hydrophilic organic solvents include: lower alcohols, such as methyl alcohol, ethyl alcohol, n-propyl alcohol, isopropyl alcohol, n-butyl alcohol, isobutyl alcohol, and t-butyl alcohol; ketones such as acetone; ethers, such as dioxane, tetrahydrofuran, methoxy(poly)ethylene glycol; amides, such as ∈-caprolactam, and N,N-dimethylformamide; sulfoxides such as dimethyl sulfoxide; and polyhydric alcohols, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol. The amount of the hydrophilic organic solvent as used is different according to factors such as the kind, particle diameter, or water content of the water-absorbent resin, but it is favorably smaller than 50 parts by weight, more favorably 0.1 to 10 parts by weight, per 100 parts by weight of the water-absorbent resin in terms of solid content. In addition, such as inorganic acids, organic acids, and poly(amino acids) shown in EP 0668080 may be allowed to exist as the third substance.

There is no especial limitation on blending methods which involve blending the water-absorbent resin and the surface-crosslinking agent, but examples thereof include: a method which involves immersing a water-absorbent resin in a hydrophilic organic solvent, and if necessary blending a surface-crosslinking agent as dissolved in water and/or the hydrophilic organic solvent; and a blending method which involves spraywise or dropwise adding a surface-crosslinking agent directly to a water-absorbent resin wherein the surface-crosslinking agent is dissolved in water and/or a hydrophilic organic solvent. In addition, the blending temperature, namely, both the temperature of the water-absorbent resin powder before blending and the temperature of the treating agent including the surface-crosslinking agent are controlled in a specific range, and thereby there is a case where the thickness or the weight ratio of the crosslinked layer is easily controlled in the range of the present invention. In addition, when the blending is carried out by using water, such as water-insoluble fine particulate powders and surfactants may be allowed to exist together.

After the water-absorbent resin and the surface-crosslinking agent are blended, the heat treatment is usually carried out to achieve the crosslinking reaction. The above heat-treating temperature depends also upon the surface-crosslinking agent as used, but the temperature of the water-absorbent resin powder is favorably adjusted to the range of 40 to 250° C. In the case, where the treating temperature is lower than 40° C., there is a case where a water-absorbing agent having excellent absorption properties cannot be obtained. In the case where the treating temperature is higher than 250° C., there is a case where the deterioration of the water-absorbent resin is caused, and the performance is lowered. Therefore, it is necessary to pay attention to this matter. The heat-treating time is in the range of about a minute to about 2 hours, favorably about 5 minutes to about an hour.

Of the matters as mentioned above, preferred examples of methods to obtain the water-absorbent resin which is usable in the present invention and displays an excellent capillary absorption index B and capillary absorption capacity D at a height of 40 cm include:

(1) a method which involve heat-treating a carboxyl-group-containing water-absorbent resin precursor having a weight-average particle diameter of not larger than 250 μm (favorably in the range of 40 to 200 μm, more favorably 70 to 150 μm), in the presence of a first surface-crosslinking agent having a solubility parameter of not less than 25.6 $[(J/cm^3)^{1/2}]$ (12.5 $[(cal/cm^3)^{1/2}]$) and a second surface-crosslinking agent having a solubility parameter of less than 25.6 $[(J/cm^3)^{1/2}]$ (12.5 $[(cal/cm^3)^{1/2}]$) wherein the surface-crosslinking agents are reactable with the carboxyl group;

(2) a method which involve: heat-treating a carboxyl-group-containing water-absorbent resin precursor in the presence of a surface-crosslinking agent at a water content of not more than 10% wherein the water-absorbent resin precursor is obtained by reversed-phase suspension polymerization and has a weight-average particle diameter of not larger than 250 μm (favorably in the range of 40 to 200 μm, more favorably 70 to 150 μm), so that the absorption capacity will be not less than 20 (g/g) under a load of 2.07 kPa (0.3 psi), favorably not less than 25 (g/g), more not less than 30 (g/g); and thereafter treating the resultant water-absorbent resin with a solvent; and (3) a method which involve: surface-crosslinking-treating a carboxyl-group-containing water-absorbent resin precursor having a weight-average particle diameter of 100 to 1,000 μm in the presence of a polyhydric alcohol or an alkylene carbonate; and thereafter classifying the resultant water-absorbent resin with a sieve having specific particle diameter distribution in order to obtain particles having a weight-average particle diameter of not larger than 300 μm (favorably in the range of 10 to 250 μm, more favorably 70 to 150 μm).

According to these methods, obtained is a water-absorbent resin displaying a capillary absorption capacity D of such as not less than 15 (g/g) at a height of 40 cm, favorably not less than 20 (g/g), most favorably not less than 25 (g/g), and it can favorably be used for the present invention. In addition, according to the above methods, obtained is a water-absorbent resin displaying a capillary absorption index B of such as not less than 0.4 at a height of 40 cm, favorably not less than 0.5, more favorably not less than 0.6, and it can favorably be used for the present invention.

Of the above, favorable is the water-absorbent resin of which the major proportion is comprised of a crosslinked poly(acrylic acid (salt)) polymer which is surface-crosslinking-treated by the above method (2) and has a weight-average particle diameter of not larger than 250 μm and is obtained by reversed-phase suspension polymerization. A hitherto unknown excellent resin displaying a capillary absorption capacity D of such as not less than 25 (g/g) at a height of 40 cm can be obtained. Incidentally, whether the surface-crosslinking treatment is carried out or not can be distinguished by such as a method that is disclosed in Japanese Patent Application No. 309105/1999.

Incidentally, various functions also can be given or enhanced to the present invention water-absorbent resin by further adding additives (e.g. water-insoluble fine-particulate inorganic powders, such as silicon dioxide, titanium dioxide, aluminum oxide, magnesium oxide, zinc oxide, talc, calcium phosphate, barium phosphate, silicic acid or its salts, clay, diatom earth, zeolite, bentonite, kaolin, hydrotalcite, and active white salts; and deodorants, perfumes, antimicrobial agents, cationic polymer compounds such as polyamines, adhesives, pressure sensitive adhesives, foaming agents, pigments, dyes, manure, oxidants, reductants, and water) to the water-swellable water-insoluble hydrogel-formable polymer, and thereby by including the additives in the above water-swellable water-insoluble hydrogel-formable polymer or attaching them thereto. The amount of the above additive as used is favorably smaller than 30 weight %, more favorably smaller than 10 weight %, still more favorably smaller than 5 weight %, particularly favorably smaller than 1 weight %, relative to the total of the water-swellable water-insoluble hydrogel-formable polymer and the additive.

(2-4) Absorbent Structure:

The present invention absorbent structure is obtained by combining a liquid-diffusing member and a water-absorbent resin in order to satisfy liquid-diffusion-and-storage coefficient 1 and/or liquid-diffusion-and-storage coefficient 2 in the present invention.

In addition, the present invention absorbent structure is also obtained by using: a liquid-diffusing member displaying a suction height of not lower than 30 cm; and a water-absorbent resin, as a liquid-storing member, displaying a capillary absorption capacity D of not less than 15 (g/g) at a height of 40 cm.

Furthermore, the present invention absorbent structure is also obtained by using: a liquid-diffusing member displaying a suction height of not lower than 30 cm; and a water-absorbent resin as a liquid-storing member wherein the water-absorbent resin is surface-crosslinking-treated and has a weight-average particle diameter of not larger than 250 μm.

The present invention absorbent structure may comprise other materials in addition to the liquid-diffusing member and the water-absorbent resin, as long as the liquid-diffusion-and-storage system as aimed in the present invention is not hindered. Examples of other materials include hydrophilic fibers, nonwoven fabrics, papers, and tissue papers. Examples of the above hydrophilic fibers include: cellulose fibers as obtained from wood, such as mechanical pulps, chemical pulps, semi-chemical pulps, and dissolved pulps; and fibers, such as rayon and acetate. Among the above-exemplified fibers, the cellulose fibers are favorable. In addition, the hydrophilic fibers may include synthetic fibers, such as polyamide, polyesters, and polyolefin. Incidentally, the hydrophilic fibers are not limited to the above-exemplified fibers. Examples of the nonwoven fabrics include nonwoven fabrics of such as polyesters, polyethylene, polypropylene, nylon, and rayon, having a spun bond, chemical bond, or spunlace system.

The weight ratio of the water-absorbent resin and the liquid-diffusing member in the absorbent structure can be selected in an arbitrarily range, but the weight ratio of the water-absorbent resin is favorably in the range of 5 to 99 weight %, more favorably 20 to 90 weight %, still more favorably 30 to 80 weight %, relative to the total weight of the water-absorbent resin and the liquid-diffusing member.

Particularly, in the case where the weight ratio of the water-absorbent resin is in the range of 75 to 90 weight % relative to the total weight of the water-absorbent resin and the liquid-diffusing member, there are advantages in that: the amount of the liquid-diffusing member as used can be lowered relatively, and therefore a lighter and thinner absorbent structure can be produced in view of shape. In addition, in order to produce the absorbent structure in which the weight ratio of the water-absorbent resin is in the range of 75 to 90 weight % relative to the total weight of the water-absorbent resin and the liquid-diffusing member, a water-absorbent resin displaying a capillary absorption capacity D of not less than 15 (g/g) at a height of 40 cm is more favorably used as the water-absorbent resin. When using a water-absorbent resin displaying a capillary absorption capacity D of not less than 15 (g/g) at a height of 40 cm as the water-absorbent resin, the transfer and diffusion of the liquid from the liquid-diffusing member to the water-absorbent resin is favorably carried out. Therefore, the storage ability is not requested as the liquid-diffusing member, and the amount of the liquid-diffusing member as used is greatly decreased. Then, a porous polymer, which is obtained by a process including the step of polymerizing a high-internal-phase emulsion and of which the suction height is not lower than 30 cm, is favorably used as the liquid-diffusing member.

Examples of the arranging position of the water-absorbent resin include: a back face of the liquid-diffusing member, a front face of the liquid-diffusing member, a portion of a back face side of the liquid-diffusing member, a portion of a front face side of the liquid-diffusing member, a portion between the liquid-diffusing members, and an inner portion of the liquid-diffusing member, and these arranging methods may be combined. Of the above, the water-absorbent resin is favorably arranged at a back face side of the liquid-diffusing member, the water-absorbent resin more favorably exists in a layer form. In addition, the weight of the water-absorbent resin per its unit area is in the range of about 50 to about 500 g/m$^2$.

Examples of the arranging state of the water-absorbent resin include: a state in which the water-absorbent resin uniformly exists over the entire surface of the liquid-diffusing member; a state in which the water-absorbent resin exists in a specific pattern; a state in which the water-absorbent resin exists with a slope of density; a state in which the water-absorbent resin exists only in the center of the liquid-diffusing member; and a state in which the water-absorbent resin exists only front and back the liquid-diffusing member.

In addition, the water-absorbent resin itself is converted to a sheet by the hitherto publicly known method, or scattered on a base material for fixing, or packed in a bag, or given adhesion. Thereafter, it may be combined with the liquid-diffusing member. Furthermore, the water-absorbent resin may adhere to the liquid-diffusing member by using an adhesive binder.

Examples of the above adhesive binder include: hot-melt adhesive fibers, such as polyolefin fibers (e.g. polyethylene, polypropylene, ethylene-propylene copolymers, and 1-butene-ethylene copolymers), and adhesive emulsions, and hot-melt adhesives. These adhesive binders may be used either alone respectively or in combinations with each other.

Incidentally, also as to the present invention absorbent structure, materials (e.g. water-insoluble fine-particulate inorganic powders, such as silicon dioxide, titanium dioxide, aluminum oxide, magnesium oxide, zinc oxide, talc, calcium phosphate, barium phosphate, silicic acid or its salts, clay, diatom earth, zeolite, bentonite, kaolin, hydrotalcite, and active white salts; deodorants; perfumes; antimicrobial agents; cationic polymer compounds such as polyamines; foaming agents; pigments; dyes; hydrophilic short fibers; manure; oxidants; reductants; and water) are further added thereto, and further functions can also be given to the absorbent structure.

[3] Absorbent Structure Comprising Liquid-Acquiring Member and Water-Absorbent Resin Layer:
(3-1) Relationship Between Capillary Absorption Ability of Liquid-Acquiring Member and that of Water-Absorbent Resin (Layer):

The relationship between the capillary absorption ability of the liquid-acquiring member and that of the water-absorbent resin (layer) in the present invention is explained.

The water-absorbent resin layer as combined with the liquid-acquiring member favorably includes a water-absorbent resin in a scattering amount of not smaller than 250 g/m$^2$, and it is composed so that the water-absorbent resin will form a substantially continuous layer when being swollen. In the case where the scattering amount is smaller than 250 g/m$^2$, there is a tendency such that: the saturated absorption quantity of the absorbent structure is decreased; the liquid-acquiring layer cannot be dried sufficiently; the dry feeling is deteriorated; and the amount of wet back of the aqueous liquid is increased. The scattering amount in the water-absorbent resin layer is more favorably not smaller than 300 g/m$^2$, still more favorably not smaller than 350 g/m$^2$, particularly favorably not smaller than 400 g/m$^2$.

The water-absorbent resin layer comprises only the water-absorbent resin or a mixture of the water-absorbent resin and other water-absorbent or hydrophilic materials. Examples of other water-absorbent or hydrophilic materials include: fibers, such as natural fibers, regenerated fibers, and synthetic fibers (e.g. pulps, rayon, polyesters, and nylon); and these hydrophilizing-treated materials. The ratio of the water-absorbent resin in the water-absorbent resin layer is favorably not less than 70 weight % in view of thinning the absorbent structure and enabling the absorption amount to increase, more favorably not less than 80 weight %, still more favorably not less than 90 weight %. The water-absorbent resin layer particularly favorably comprises only the water-absorbent resin (namely, 100 weight %).

The water-absorbent resin usable in the present invention is a water-absorbent resin wherein when the capillary absorption index of the liquid-acquiring member at a height of 40 cm is referred to as E (E<0.1), the capillary absorption index B of the water-absorbent resin at a height of 40 cm satisfies the following equation:

$$B/E \geq 10 \quad \text{(equation 3)}$$

In addition, the water-absorbent resin layer usable in the present invention is a water-absorbent resin wherein when the capillary absorption index of the liquid-acquiring-member at a height of 40 cm is referred to as E (E<0.1), the capillary absorption index F of the water-absorbent resin layer at a height of 40 cm satisfies the following equation:

$$F/E \geq 10 \quad \text{(equation 4)}$$

The value of the capillary absorption index B or F of the water-absorbent resin or water-absorbent resin layer necessary in the present invention at a height of 40 cm is different depending upon the property of the liquid-acquiring member as used, namely, the capillary absorption index E of the liquid-acquiring member as used at a height of 40 cm. If the above relationship $B/E \geq 10$ or $F/E \geq 10$ is satisfied, a liquid from the liquid-acquiring member to the water-absorbent resin is favorably absorbed, and the water-absorbent resin can dry the liquid-acquiring member sufficiently. In the case where the B/E or F/E is less than 10, there are cases where: the water-absorbent resin cannot absorb the liquid from the liquid-acquiring member sufficiently; and the liquid-acquiring member is left in a wet feeling; and the next liquid cannot be received in a moment. The water-absorbent resin favorably satisfies $B/E \geq 20$ or $F/E \geq 20$, more favorably $B/E \geq 30$ or $F/E \geq 30$. Incidentally, hereinafter, the value of the B/E or F/E may be referred to as a liquid-acquirement-and-storage coefficient 1. In addition, the B means a capillary absorption index as determined by using a single water-absorbent resin, and the F means a capillary absorption index as determined by using a water-absorbent resin layer itself, when it is, for example, difficult to isolate the water-absorbent resin from the water-absorbent resin layer.

As to another absorbent structure usable in the present invention, the liquid-acquiring member displays a capillary absorption capacity G of not more than 1.0 (g/g) at a height of 40 cm, and the aforementioned water-absorbent resin displays a capillary absorption capacity D of not less than 5 (g/g) at a height of 40 cm.

In addition, as to another absorbent structure usable in the present invention, the liquid-acquiring member displays a capillary absorption capacity G of not more than 1.0 (g/g) at a height of 40 cm, and the aforementioned water-absorbent resin layer displays a capillary absorption capacity H of not less than 5 (g/g) at a height of 40 cm.

If the liquid-acquiring member and the water-absorbent resin or water-absorbent resin layer satisfy these relationships, a liquid from the liquid-acquiring member to the water-absorbent resin is favorably distributed, and the water-absorbent resin can dry the liquid-acquiring member sufficiently, and the liquid can be absorbed and stored therein.

In the case where the D or H is less than 5 (g/g), the water-absorbent resin difficultly absorbs the liquid from the liquid-acquiring member sufficiently, and the liquid-acquiring member is not dried, and the amount of wet back of the aqueous liquid is greatly increased. The value of the capillary absorption capacity D or H of the water-absorbent resin or water-absorbent resin layer necessary in the present invention at a height of 40 cm is favorably not less than 10 (g/g), more favorably not less than 15 (g/g), most favorably not less than 20 (g/g). In addition, hereinafter, when the value of the D/F or H/F may be referred to as a liquid-acquirement-and-storage coefficient 2, this value is favorably not less than 30, more favorably not less than 50.

In the present invention, it is more favorable that both the values of the liquid-acquirement-and-storage coefficient 1, D and H as mentioned above satisfy the present invention range. When only the one value satisfies the range, the liquid absorption ability of the water-absorbent resin from the liquid-acquiring member may not be displayed favorably, and therefore it is necessary to pay attention to this matter. As is similarly mentioned above, the D means a capillary absorption capacity as determined by using a single water-absorbent resin, and the H means a capillary absorption capacity as determined by using a water-absorbent resin layer itself, when it is, for example, difficult to isolate the water-absorbent resin from the water-absorbent resin layer.

(3-2) Liquid-Acquiring Member:

The liquid-acquiring member usable in the present invention is a member that acts the part of: capturing a liquid as added to an absorbent structure or an absorbent article including the absorbent structure in a moment; and not leaking the liquid out of the absorbent structure. The liquid-acquiring member is defined as a material displaying a capillary absorption index E of less than 0.10 at a height of 40 cm and a capillary absorption capacity G of not more than 1.0 (g/g) at a height of 40 cm. Generally, even after the liquid-acquiring member is loaded or absorbed, it has such a structure as can maintain a space for capturing the liquid.

The liquid-acquiring member usable in the present invention is a member having excellent liquid-acquiring and liquid-releasing ability, and it is necessary that the capillary absorption index E is less than 0.1 at a height of 40 cm. The capillary absorption index E of such as flap pulp as used for disposable diapers hitherto is 0.04 at a height of 40 cm according to the measurement method in the present invention. Such a material can also be used as the liquid-acquiring member of the present invention. If this value is smaller, it favorably has excellent liquid-acquiring and liquid-releasing ability. A material displaying a capillary absorption index E of not less than 0.10 retains a liquid in the material comparatively strongly. When the material repeatedly absorbs the liquid, the liquid-acquiring performance is rapidly deteriorated. Therefore, it is difficult to improve such as the leakage, the wet feeling, and the amount of wet back of the aqueous liquid. The liquid-acquiring member favorably has a capillary absorption index E of not more than 0.03 at a height of 40 cm.

In addition, the liquid-acquiring member usable in the present invention favorably displays a capillary absorption capacity of not less than 5 (g/g) at a height of 0 cm. The higher the capillary absorption capacity is at a height of 0 cm, the larger the liquid acquisition capacity of the liquid-acquiring member is. Then, obtained is an absorbent structure having excellent instantaneous absorption and temporary storage of the liquid. The capillary absorption capacity is more favorably not less than 10 (g/g) at a height of 0 cm, still more favorably not less than 15 (g/g).

It is necessary that another liquid-acquiring member usable in the present invention displays a capillary absorption capacity G of not more than 1.0 (g/g) at a height of 40 cm. The capillary absorption capacity G of such as flap pulp as used for disposable diapers hitherto is about 0.5 (g/g) at a height of 40 cm. Such a material can also be used as the liquid-acquiring member of the present invention. If this value is smaller, it favorably has excellent liquid-acquiring and liquid-releasing ability. A material displaying a capillary absorption capacity G of more than 1.0 (g/g) at a height of 40 cm retains a liquid in the material comparatively strongly. When the material repeatedly absorbs the liquid, the liquid-acquiring performance is rapidly deteriorated. Therefore, it is difficult to improve such as the leakage, the wet feeling, and the amount of wet back of the aqueous liquid. The liquid-acquiring member favorably has a capillary absorption capacity G of not more than 0.4 (g/g) at a height of 40 cm, more favorably not more than 0.2 (g/g).

In addition, similarly, another liquid-acquiring member usable in the resent invention favorably displays a capillary absorption capacity of not less than 5 g/g) at a height of 0 cm, but the above limitation is not applied if the retention of the liquid is not an important object. However, generally, the higher the capillary absorption capacity is at a height of 0 cm, the larger the liquid acquisition capacity of the liquid-acquiring member is. Then, obtained is an absorbent structure having excellent instantaneous absorption and temporary storage of the liquid. The capillary absorption capacity is more favorably not less than 10 (g/g) at a height of 0 cm, still more favorably not less than 15 (g/g).

The liquid-acquiring member usable in the present invention satisfies the above conditions, and is used together with a water-absorbent resin (layer), and thereby they are used as an absorbent structure.

As to the relationship between both of them, as is aforementioned, it is necessary that: when the capillary absorption index of the liquid-acquiring member at a height of 40 cm is referred to as E (E<0.1), the capillary absorption index B of the above water-absorbent resin at a height of 40 cm satisfies B/E≧10, or the capillary absorption index F of the above water-absorbent resin layer at a height of 40 cm satisfies F/E≧10.

In addition, as to the relationship between both of them, it is necessary that: when the capillary absorption capacity of the liquid-acquiring member at a height of 40 cm is referred to as G (G≦1.0 (g/g)), the capillary absorption capacity D of the above water-absorbent resin at a height of 40 cm satisfies not less than 5 (g/g), or the capillary absorption capacity H of the above water-absorbent resin layer at a height of 40 cm satisfies not less than 5 (g/g).

Furthermore, both of them more favorably satisfy the B/E≧10 and D≧5.0, or the F/E≧10 and H≧5.0 at the same time.

The shape of the liquid-acquiring member can be such as a sheet shape, a fibrous shape, a fibrous aggregate, a particulate shape, or a strip shape, but it is favorably a sheet shape in general. Then, the weight of the liquid-acquiring member per its unit area is favorably in the range of about 50 to about 500 g/m$^2$, more favorably about 100 to about 200 g/m$^2$.

In addition, when the liquid-acquiring member has a difference of density, a slope of density, a difference of acquisition ability, and a slope of acquisition ability in the member, or when a second liquid-acquiring member or liquid-diffusing member not satisfying the present invention relationship is further used, it is favorable to make the capillary absorption ability of a portion of the liquid-acquiring member much closer to the water-absorbent resin satisfy the above relationship.

Examples of the liquid-acquiring member usable in the present invention include: flap pulps, crosslinking-treated cellulose fibers, synthetic fibers (e.g. nonwoven fabrics having a bulky structure), porous polymers obtained by a process including the step of polymerizing a high-internal-phase emulsion (HIPE), and foaming structures including synthetic polymers (e.g. polyurethanes, polystyrene, polyethylene, polypropylene, polyesters, poly(vinyl alcohol), butadiene-styrene rubbers (SBR), and nitrile-butadiene rubbers); fibrous aggregates as obtained by adhering to or combining with synthetic fibers, such as polyethylene, polypropylene, polyethylene terephthalate, and nylon; rayon fibers; and fibrous aggregates as obtained by adhering to under a pressure, adhering to, or combining with hydrophilic fibers, such as cellulose fibers (e.g. celluloses, cellulose acetate, and nitrocellulose) and polyamide fibers. The crosslinking-treated cellulose fibers, the synthetic fibers such as the nonwoven fabrics having a bulky structure, and the porous polymers obtained by a process including the step of polymerizing a high-internal-phase emulsion (HIPE) are favorable.

(3-3) Water-Absorbent Resin:

Water-absorbent resins have hitherto been used as materials absorbing liquids due to the osmotic pressure difference between the inside and the outside of the resins, and as liquid-storing members such as disposable diapers. However, the present inventors took note of that: even if the properties of the water-absorbent resins as known hitherto (e.g. absorption capacity of water-absorbent resin, absorption capacity of water-absorbent resin under a load) are identical, the absorbing behaviors are greatly different due to the kinds of resins when liquids are absorbed from such as the liquid-acquiring member. Then, the present inventors diligently considered, and found out that: the capillary absorption ability is greatly different even in a water-absorbent resin itself, and the water-absorbent resin can receive and store a liquid from the liquid-acquiring member more favorably when the relationship between the capillary absorption ability of the liquid-acquiring member and the capillary absorption ability of the water-absorbent resin satisfies a specific condition.

The water-absorbent resin usable in the present invention is a water-absorbent resin, in which, as is mentioned above, when the capillary absorption index of the above liquid-acquiring member at a height of 40 cm is referred to as E (E<0.10), the capillary absorption index B of the water-absorbent resin at a height of 40 cm satisfies $B/E \geqq 10$, favorably $B/E \geqq 20$, more favorably $B/E \geqq 30$. The water-absorbent resin may be measured in a state of a water-absorbent resin layer as taken out from the absorbent structure, and then the capillary absorption index F of the above water-absorbent resin layer at a height of 40 cm satisfies $F/E \geqq 10$, favorably $F/E \geqq 20$, more favorably $F/E \geqq 30$.

The value of the capillary absorption index B of the water-absorbent resin necessary in the present invention or the capillary absorption index F of the water-absorbent resin layer at a height of 40 cm is different depending upon the property of the liquid-acquiring member as used, namely, the capillary absorption index E of the liquid-acquiring member as used at a height of 40 cm. If the above relationship $B/E \geqq 10$ or $F/E \geqq 10$ is satisfied, a liquid from the liquid-acquiring member to the water-absorbent resin or water-absorbent resin layer is favorably transferred. Then, the water-absorbent resin can favorably absorb and store the liquid, and the liquid-acquiring member can be dried. The capillary absorption index B of the water-absorbent resin or the capillary absorption index F of the water-absorbent resin layer is favorably not less than 0.2 at a height of 40 cm, more favorably not less than 0.4, still more favorably not less than 0.6.

In addition, the water-absorbent resin as used in the present invention favorably displays a capillary absorption capacity of not less than 20 (g/g) at a height of 0 cm. If the capillary absorption capacity at a height of 0 cm is higher, the water-absorbent resin can retain a large amount of liquid as sucked up from the liquid-acquiring member. Therefore, an excellent absorbent structure is obtained from the viewpoint of the liquid absorption ability. The water-absorbent resin favorably displays a capillary absorption capacity of not less than 30 (g/g) at a height of 0 cm, more favorably not less than 40 (g/g), still more favorably not less than 50 (g/g). However, when the capillary absorption capacity at a height of 0 cm is too high, there is a case where: even if the liquid-diffusing member is used, a liquid is difficultly entered into the absorbent structure. Therefore, it is necessary to pay attention to this matter.

In addition, another water-absorbent resin usable in the present invention is a water-absorbent resin that favorably satisfies a capillary absorption capacity D of not less than 5 (g/g) at a height of 40 cm, more favorably not less than 10 (g/g), still more favorably not less than 15 (g/g), most favorably not less than 20 (g/g). The water-absorbent resin may be measured in a state of a water-absorbent resin layer as taken out from the absorbent structure, and then the capillary absorption capacity H of the above water-absorbent resin layer favorably satisfies not less than 5 (g/g) at a height of 40 cm, more favorably not less than 10 (g/g), still more favorably not less than 15 (g/g), most favorably not less than 20 (g/g).

The water-absorbent resin usable in the present invention satisfies the above conditions. It is used together with a liquid-acquiring member that satisfies the requisite in the present invention, and thereby they are used as an absorbent structure.

The shape of the water-absorbent resin can be such as a particulate, fibrous, sheet, or strip shape, but it is favorably a particulate shape in general. In addition, as to the production method thereof, aqueous solution polymerization or reversed-phase suspension polymerization can be carried out.

In the present invention, a water-absorbent resin satisfying the above relationship and a water-absorbent resin not satisfying the above relationship may be used together as the water-absorbent resin, but only the water-absorbent resin satisfying the above relationship is favorably used in order to display the present invention effect to the maximum. In addition, the resin is favorably arranged so that the capillary absorption ability of a portion of the water-absorbent resin will satisfy the above relationship, wherein the portion is much closer to the liquid-acquiring member.

Examples of the water-absorbent resin usable in the present invention, examples of monomers used as raw materials of the above water-absorbent resin and their amounts as used, methods for introducing a crosslinked structure, explanations as to internal crosslinking, examples of additives and their amounts as used when the polymerization is carried out, polymerization methods, the shape of the water-absorbent resin as obtained, explanations as to surface crosslinking, and explanations as to additives to give further functions to the water-absorbent resin are the same as mentioned in the previous (2-3) item.

Examples of preferred methods to obtain the water-absorbent resin usable in the present invention, which displays an excellent capillary absorption index B and capillary absorption capacity D at a height of 40 cm include:

(1) a method which involve heat-treating a carboxyl-group-containing water-absorbent resin precursor having a weight-average particle diameter of 100 to 500 μm (favorably 200 to 400 μm), in the presence of a first surface-crosslinking agent having a solubility parameter of not less than 25.6 $[(J/cm^3)^{1/2}]$ (12.5 $[(cal/cm^3)^{1/2}]$) and a second surface-crosslinking agent having a solubility parameter of less than 25.6 $[(J/cm^3)^{1/2}]$ (12.5 $[(cal/cm^3)^{1/2}]$) wherein the surface-crosslinking agents are reactable with the carboxyl group;

(2) a method which involve: heat-treating a carboxyl-group-containing water-absorbent resin precursor in the presence of a surface-crosslinking agent at a water content of not more than 10% wherein the water-absorbent resin precursor is obtained by reversed-phase suspension polymerization and has a weight-average particle diameter of not larger than 250 μm (favorably in the range of 40 to 200 μm, more favorably 70 to 150 μm), so that the absorption capacity will be not less than 20 (g/g) under a load of 0.3 psi, favorably not less than 25 (g/g), more favorably not less than 30 (g/g); and thereafter treating the resultant water-absorbent resin with a solvent; and (3) a method which involve: treating a carboxyl-group-containing water-absorbent resin precursor having a weight-average particle diameter of 100 to 600 μm in the presence of a polyhydric alcohol or an alkylene carbonate in order to have a specific surface-crosslinked layer; and thereafter classifying the resultant water-absorbent resin with a sieve having specific particle diameter distribution in order to obtain particles having a weight-average particle diameter of not larger than 400 μm (favorably in the range of 100 to 400 μm).

According to these methods, obtained is a water-absorbent resin displaying a capillary absorption capacity D of such as not less than 10 (g/g) at a height of 40 cm, favorably not less than 15 (g/g), most favorably not less than 25 (g/g), and it can favorably be used for the present invention. In addition, according to the above methods, obtained is a water-absorbent resin displaying a capillary absorption index B of such as not less than 0.2 at a height of 40 cm, favorably not less than 0.4, more favorably not less than 0.6, and it can favorably be used for the present invention.

(3-4) Absorbent Structure:

The present invention absorbent structure is obtained by combining the liquid-acquiring member and the water-absorbent resin layer that satisfy the above properties. The water-absorbent resin layer has the above-mentioned water-absorbent resin amount and structure.

In the present invention absorbent structure, the water-absorbent resin layer favorably has a scattering amount of not smaller than 250 g/m², and the water-absorbent resin layer is composed so that the water-absorbent resin will be a substantially continuous layer when being swollen. In the case where the scattering amount is smaller than 250 g/m², there is a tendency such that: the saturated absorption quantity of the absorbent structure is decreased; the liquid-acquiring layer cannot be dried sufficiently; the dry feeling is deteriorated; and the amount of wet back of the aqueous liquid is increased. The scattering amount in the water-absorbent resin layer is favorably not smaller than 300 g/m², more favorably not smaller than 350 g/m², still more favorably not smaller than 400 g/m².

The water-absorbent resin usable in the present invention may comprise other base material (e.g. a small amount of hydrophilic or synthetic fibers) in addition to the above water-absorbent resin as long as the liquid-acquisition-and-storage system as aimed in the present invention is not hindered. However, in order to display the transfer of the liquid from the liquid-acquiring member to the maximum, it is favorable that: the water-absorbent resin itself is scattered, and the water-absorbent resin layer with the above-mentioned scattering amount is formed.

The present invention absorbent structure may comprise other materials in addition to the liquid-acquiring member and the water-absorbent resin as long as the objective liquid-acquisition-and-storage system in the present invention is not hindered. Examples of other materials include hydrophilic fibers, nonwoven fabrics, papers, and tissue papers. Examples of the above hydrophilic fibers include: cellulose fibers as obtained from wood, such as mechanical pulps, chemical pulps, semi-chemical pulps, and dissolved pulps; and fibers, such as rayon and acetate. Among the above-exemplified fibers, the cellulose fibers are favorable. In addition, the hydrophilic fibers may include synthetic fibers, such as polyamide, polyesters, and polyolefin. Incidentally, the hydrophilic fibers are not limited to the above-exemplified fibers. Examples of the nonwoven fabrics include nonwoven fabrics of such as polyesters, polyethylene, polypropylene, nylon, and rayon, having a spun bond, chemical bond, or spunlace system.

In the present invention absorbent structure, the liquid-acquiring member and the water-absorbent resin layer are favorably comprised of one layer each. In the case where the liquid-acquiring member is comprised of at least two layers, there is a case where: a liquid is not favorably absorbed from the entire liquid-acquiring member to the water-absorbent resin layer in the absorbent structure; and the dry feeling and the amount of wet back of the aqueous liquid are deteriorated.

The ratio of the water-absorbent resin layer and the liquid-acquiring member in the absorbent structure can be selected in an arbitrarily range, but the weight ratio of the water-absorbent resin layer is favorably not smaller than 70 weight %, more favorably in the range of 80 to 95 weight %, relative to the total weight of the liquid-acquiring member and the water-absorbent resin layer.

In addition, the weight ratio of the liquid absorption quantity of the water-absorbent resin layer is favorably not less than 80 weight %, more favorably in the range of 80 to 95 weight %, still more favorably in the range of 90 to 95 weight %, relative to the saturated liquid absorption quantity of the absorbent structure.

In the present invention, the amount of the liquid-acquiring member or the water-absorbent resin layer as used depends upon the size of an objective absorbent article. When the absorbent article is assumed to be a L-size diaper for children, the amount of the liquid-acquiring member is favorably 0.5 to 4 g, more favorably about 1 to about 2 g, and the amount of the water-absorbent resin layer is favorably 10 to 30 g, more favorably about 15 to about 20 g.

Examples of the arranging position of the water-absorbent resin layer include: a back face of the liquid-acquiring member (a liquid-impermeable back sheet side of an absorbent article), a front face of the liquid-acquiring member, a portion of a back face side of the liquid-acquiring member, a portion of a front face side of the liquid-acquiring member, a portion between the liquid-acquiring members, and an inner portion of the liquid-acquiring member, and these arranging methods may be combined. Of the above, the water-absorbent resin layer is favorably arranged at a back face side of the liquid-acquiring member. Examples of the arranging state of the water-absorbent resin layer include: a state in which the water-absorbent resin uniformly exists over the whole surface of liquid-acquiring member; a state in which the water-absorbent resin exists in a specific pattern; a state in which the water-absorbent resin exists with stripes; a state in which the water-absorbent resin exists with a slope of density; a state in which the water-absorbent resin exists only in the center of the liquid-acquiring member; and a state in which the water-absorbent resin exists only front and back the liquid-acquiring member. It is favorable that the area where the water-absorbent resin layer exists is larger than that where the liquid-acquiring member exists. The area ratio of the water-absorbent resin layer is favorably not less than 1.2, more favorably not less than 2, relative to the area 1 of the liquid-acquiring member.

In addition, the water-absorbent resin or water-absorbent resin layer itself is converted to a sheet by the hitherto publicly known method, or scattered on a base material for fixing, or packed in a bag, or given adhesion. Thereafter, it may be combined with the liquid-acquiring member. Furthermore, the water-absorbent resin layer may adhere to the liquid-acquiring member by using an adhesive binder.

Examples of the above adhesive binder include: hot-melt adhesive fibers, such as polyolefin fibers (e.g. polyethylene, polypropylene, ethylene-propylene copolymers, and 1-butene-ethylene copolymers), and adhesive emulsions, and hot-melt adhesives. These adhesive binders may be used either alone respectively or in combinations with each other. In this case, it is more favorably that the capillary absorption ability of not only the water-absorbent resin itself but also the water-absorbent resin layer in a fixed state satisfies the present invention range.

Incidentally, also as to the present invention absorbent structure, materials (e.g. water-insoluble fine-particulate inorganic powders, such as silicon dioxide, titanium dioxide, aluminum oxide, magnesium oxide, zinc oxide, talc, calcium phosphate, barium phosphate, silicic acid or its salts, clay, diatom earth, zeolite, bentonite, kaolin, hydrotalcite, and active white salts; deodorants; perfumes; antimicrobial agents; cationic polymer compounds such as polyamines; foaming agents; pigments; dyes; hydrophilic short fibers; manure; oxidants; reductants; and water) are further added thereto, and further functions can also be given, to the absorbent structure.

Incidentally, the aforementioned absorbent structure according to the present invention, namely, the absorbent structure comprising the liquid-acquiring member and the water-absorbent resin layer may further comprise the aforementioned liquid-diffusing member. In this case, an absorbent structure having both the above-mentioned characteristic (which the present invention absorbent structure comprising the liquid-diffusing member and the water-absorbent resin has) and the characteristic (which the present invention absorbent structure comprising the liquid-acquiring member and the water-absorbent resin layer has) together is favorable because the present invention effect can be displayed further more.

[4] Absorbent Article:

The present invention absorbent article generally comprises: the present invention absorbent structure having the above constitution, namely, the absorbent structure including the liquid-diffusing member and the water-absorbent resin, or the absorbent structure including the liquid-acquiring member and the water-absorbent resin layer; a liquid-permeable sheet; and a liquid-impermeable sheet, wherein the absorbent structure is sandwiched between the liquid-permeable sheet and the liquid-impermeable sheet. Then, the above absorbent article has excellent water absorption properties as mentioned above because it comprises the absorbent structure having the above constitution. Specific examples of the above absorbent article include: sanitary materials such as disposable diapers, sanitary napkins, and so-called incontinent pads; medical sheets; and dew-absorbent sheets, but there is no especial limitation thereto. The present invention absorbent article has excellent absorption properties. Therefore, when the above absorbent article is, for example, a disposable diaper, the liquid absorption efficiency is increased very much, and the leakage of urine can be inhibited, and besides, the so-called dry feeling can be given, and the thinning and lightening can be realized.

The material referred to as the above liquid-permeable sheet is a material having a property of permeating an aqueous liquid, and examples thereof include: nonwoven fabrics; woven fabrics; and porous synthetic resin films comprised of polyethylene, polypropylene, polyesters, or polyamides. The above liquid-impermeable sheet is a, material having a property of not permeating an aqueous liquid, and examples thereof include: synthetic resin films of polyethylene, polypropylene, ethylene vinyl acetate, and polyvinyl chloride; films of combined materials of these synthetic resins with nonwoven fabrics; and films of combined materials of the above synthetic resins with woven fabrics. Incidentally, the liquid-impermeable sheet may have a property of making vapor permeate.

As is mentioned above, in the present invention, the water-absorbent resin, which displays a capillary absorption ability having a specific relationship with that of the liquid-diffusing member or liquid-acquiring member, is combined and used with the above liquid-diffusing member or liquid-acquiring member. Therefore, the water-absorbent resin can favorably absorb or store a liquid from the liquid-diffusing member or liquid-acquiring member, and it displays very excellent liquid absorption efficiency. Specifically, the present invention makes the system as called the diffusion to the storage of the liquid favorably work, and can provide the absorbent structure and the absorbent article displaying very excellent liquid diffusion and storage ability by a very simple production process.

In the absorbent article as produced by using such an absorbent structure (e.g. disposable diapers, sanitary napkins, and so-called incontinent pads), the liquid absorption efficiency of the member is high. Therefore, the entire member is effectively used for the liquid absorption, and the high absorption ability is displayed. In addition, when the absorption ability of the absorbent structure or absorbent article having such high absorption efficiency is designed in the same absorption quantity level as of the hitherto diapers on the market, the amount of the liquid-diffusing member, the liquid-acquiring member, or the water-absorbent resin as used can be decreased still more less than that of the hitherto ones, and light and thin-type diapers can be produced economically.

[5] Water-Absorbent Resin Particles:

The water-absorbent resin usable for the present invention absorbent structure and absorbent article is mentioned above. The present invention also provides: water-absorbent resin particles as a particularly favorable water-absorbent resin; and a production process therefore, as explained below.

The production process for water-absorbent resin particles, according to the present invention, is characterized by comprising the step of adding a dispersion of water-dispersible fine particles to a water-absorbent resin, thereby increasing the weight-average particle diameter of the water-absorbent resin by not less than 50%, wherein the water-absorbent resin has a weight-average particle diameter of 50 to 300 µm and displays a space ratio of 30 to 50% and an average space radius of 80 to 150 µm as to spaces between particles when saturation-swollen with a physiological saline (a 0.9 weight % aqueous NaCl solution) without load.

The water-absorbent resin usable in the present invention production process for water-absorbent resin particles has a weight-average particle diameter of 50 to 300 µm, and displays a space ratio of 30 to 50% and average space radius of 80 to 150 µm as to spaces between particles when saturation-swollen with a physiological saline (a 0.9 weight % aqueous NaCl solution) without load.

These are obtained by optimizing such as a weight-average particle diameter, particle diameter distribution, surface-crosslinking agents, and thickness of a surface-crosslinked layer when producing the water-absorbent resin as used for the aforementioned absorbent structure and absorbent article according to the present invention. Examples of its method include:

(1) a method which involves heat-treating a carboxyl-group-containing water-absorbent resin in the presence of a surface-crosslinking agent that is reactable with the above carboxyl group (e.g. polyhydric alcohols, epoxy compounds, oxazoline compounds, alkylene carbonates, or oxazilidone compounds), and thereby carrying out surface-crosslinking treatment so that the above surface-crosslinked layer is in a predetermined range; and (2) a method which involves heat-treating a carboxyl-group-containing water-absorbent resin in the presence of a surface-crosslinking agent that is reactable with the above carboxyl group, and adding a cationic polymer having a molecular weight in a specific range.

Incidentally, the method of measuring the thickness of the surface-crosslinked layer is disclosed in such as Japanese Patent Application No. 329501/2000. The cationic polymer is exemplified in such as JP-A-031360/1993 and JP-A-000370/1994.

The water-absorbent resin as obtained in this method, which displays a space ratio of 30 to 50% and an average space radius of 80 to 150 µm as to spaces between particles when saturation-swollen without load, is used as a raw material powder.

In addition, the present invention water-absorbent resin particles have firm granulation ability when they are dry. However, when they contact a large quantity of liquid, the bond is broken and therefore they have re-dispersibility. When granule particles are, for example, saturation-swollen with a physiological saline (a 0.9 weight % aqueous NaCl solution), it results in a state where the particles are dispersed again, and freely absorb a liquid and are swollen, and then the particles display a space ratio of 30 to 50% and an average space radius of 80 to 150 µm as to spaces between particles when saturation-swollen without load.

The water-absorbent resin usable in the present invention production process for water-absorbent resin particles has a weight-average particle diameter of 50 to 300 µm, but it favorably has a weight-average particle diameter of 100 to 300 µm, more favorably 150 to 250 µm in order to more effectively obtain the water-absorbent resin particles according to the present invention.

The water-absorbent resin usable in the present invention production process for water-absorbent resin particles displays a space ratio of 30 to 50% as to spaces between particles when saturation-swollen with a physiological saline (a 0.9 weight % aqueous NaCl solution) without load, but it favorably displays a space ratio of 35 to 45% in order to more effectively obtain the water-absorbent resin particles according to the present invention.

The water-absorbent resin usable in the present invention production process for water-absorbent resin particles displays an average space radius of 80 to 150 µm as to spaces between particles when saturation-swollen without load.

The present invention production process for water-absorbent resin particles is characterized by comprising the step of adding a dispersion of water-dispersible fine particles to the water-absorbent resin having the above-mentioned characteristics, thereby increasing the weight-average particle diameter of the water-absorbent resin by not less than 50%.

As to the water-dispersible fine particles usable in the present invention, examples of powdery inorganic substances include: water-insoluble fine-particulate inorganic powders (e.g. silicon dioxide, aluminum oxide, zinc oxide, magnesium oxide, titanium dioxide, calcium phosphate, barium phosphate, calcium carbonate, talc, magnesium phosphate, calcium sulfate, silicic acid or its salts, clay, diatom earth, bentonite, zeolite, kaolin, hydrotalcite, and active white salts), and other metal oxides. Particularly, the silicon dioxide, aluminum oxide, and titanium dioxide are favorable.

These water-dispersible fine particles favorably have a weight-average primary particle diameter (a weight-average particle diameter of individual particles, a weight-average particle diameter of individual particles before aggregation or granulation when the at least two particles are aggregated or granulated) of not larger than 3.0 µm in general, more favorably in the range of 3.0 to 0.005 µm, and they are favorably extremely fine particles having particle diameters of not larger than 0.1 µm on average.

The amount of the above water-dispersible fine particles as contained and used is generally in the range of favorably 0.1 to 5 parts by weight, more favorably 0.3 to 2.0 parts by weight, per 100 parts by weight of the water-absorbent resin. In the case where the amount of the powdery inorganic substance as added is generally smaller than 0.1 part by weight, granules cannot be obtained, or the effect is poor even if granules can be obtained. On the other hand, in the case where the amount of the water-dispersible fine particles is larger than 5 parts by weight, lumps are obtained as the granules, or, even if granules are obtained, they are coarse particles and have a bad influence upon absorption performance. In addition, the further effect for the addition cannot be expected, and therefore it is not economical. Particles having arbitrary particle diameters in a narrow range of particle diameter distribution are obtained by changing the amount as added in these ranges.

The water-dispersible fine particles as used in the present invention have such a property of not inhibiting permeability of water and swellability of water-absorbent resins, and do not prevent the component as combined from permeating and absorbing of the liquid. In addition, they do not cause the blocking when being swollen, and display the absorption ability of the water-absorbent resin sufficiently. In addition, we found out that the granulated water-absorbent resin particles have firm granulation ability and no powdery dust when they are dry; when they absorb a liquid, the water-dispersible fine particles introduce and distribute water, and besides, the bond is broken; and the water-absorbent resin has a property of freely absorbing a liquid and swelling.

In the present invention, the aforementioned water-dispersible fine particles are used as a dispersion obtained by dispersing them in water or an aqueous medium.

The amount of the dispersion as used is favorably in the range of 3 to 100 parts by weight per 100 parts by weight of the water-absorbent resin. In the case where the amount of the dispersion is smaller than 3 parts by weight, granules cannot be obtained, or the effect is poor even if granules can be obtained. On the other hand, in the case where the amount of the dispersion is larger than 100 parts by weight, there are disadvantages in that lumps are obtained as the granules, or, even if granules are obtained, they are coarse particles.

It is favorable that when the water-dispersible fine particles are dispersed in an aqueous medium, they display a so-called structural viscosity and the viscosity of the dispersion having a concentration of 6.7 weight % is not less than 0.5 Pa·s (Brookfield rotary viscometer, 6 rpm, and 25® C.).

As to the amount of the water-dispersible fine particles and the amount of water in the dispersion, it is necessary that the amount as added is each determined and selected, in order to obtain the optimum granulation state, depending upon the particle surface area or surface state of the water-absorbent resin.

The present invention water-absorbent resin particles are obtained by a process including the steps of: blending a water-absorbent resin and a dispersion of water-dispersible fine particles; and then heat-drying the resultant mixture. As to the method for blending the water-absorbent resin and the dispersion of the water-dispersible fine particles, general is a method of spraywise or dropwise adding the above treating solution to the water-absorbent resin powder, and then blending them. The blender as used for blending is favorably a blender having large blendability to carry out blending uniformly, but conventional blenders or kneaders can be used. Examples thereof include cylinder type blenders, double-wall cone type blenders, V-character-shaped blenders, ribbon type blenders, screw type blenders, fluidizing type blenders, rotary disk type blenders, air blow type blenders, twin-arm type kneaders, internal mixers, roll mixers, and screw type extruders. Conventional dryers or heating furnaces can be used in order to heat a mixture as obtained by blending the water-absorbent resin powder with these treating solution. Examples thereof include channel type blending dryers, rotary dryers, disk dryers, kneading dryers, fluidized-bed dryers, air blow type dryers, infrared dryers, and dielectric-heating dryer. The heat-treating temperature is favorably in the range of 40 to 250° C., more favorably 80 to 200° C.

In the present invention production process for water-absorbent resin particles, the weight-average particle diameter of the water-absorbent resin particles as obtained increases by not less than 50% by adding the above dispersion of the water-dispersible fine particles.

The present invention water-absorbent resin particles as obtained by the above production process have an absorption property (e.g. high capillary aspiration ability) that water-absorbent resin particles as obtained by conventional methods could not obtain. Furthermore, the dispersion of the water-dispersible fine particles works as an excellent binder. Therefore, the mechanical strength of the particles as obtained is remarkably improved and the scatter of the water-absorbent resin particles can be remarkably suppressed when they are practically used.

That is to say, the present invention water-absorbent resin particles are water-absorbent resin particles as obtained by a process including the step of granulating a water-absorbent resin having a weight-average particle diameter of 50 to 300 μm and displaying a space ratio of 30 to 50% and an average space radius of 80 to 150 μm as to spaces between particles when saturation-swollen with a physiological saline (a 0.9 weight % aqueous NaCl solution) without load, wherein the water-absorbent resin particles have a weight-average particle diameter as increased by not less than 50% of that before the granulating step.

The weight-average particle diameter of the present invention water-absorbent resin particles is favorably 150 to 600 μm, more favorably 200 to 500 μm, still more favorably 200 to 400 μm.

The present invention water-absorbent resin particles favorably display a capillary absorption capacity of not less than 7 g/g at a height of 40 μm, more favorably not less than 15 g/g, still more favorably not less than 25 g/g.

The present invention water-absorbent resin particles are blended and used with such as a pulverized pulp because of their improved absorption properties. Thereby, they display particularly excellent effects. Its mixture including the pulverized pulp is molded in a mat shape, and thereby it can favorably be used as the water-absorbent resin layer of the absorbent structure of such as disposable diapers and sanitary napkins. The present inventors certified that making the absorption rate fast without limit conversely leads to lowering the absorption rate under the load. Therefore, the absorption rate is favorably controlled in a suitable range for this use particularly. Controlling a capillary absorption capacity of not less than 7 (g/g) at a height of 40 cm is a critical meaning in the present invention. Furthermore, in the present invention water-absorbent resin particles, the ratio of particles passing through a wire net of 150 μm is not more than 50% of that before the granulation. Therefore, the present invention also has a merit of little scattering a powdery dust, and provides novel water-absorbent resin particles as hitherto unknown.

DETAILED DESCRIPTION OF THE PREFERRED EMBODIMENTS

Hereinafter, the present invention is more specifically illustrated by the following examples in comparison with comparative examples. However, the invention is not limited to these examples. Incidentally, the various performances of the liquid-diffusing members, liquid-acquiring members, water-absorbent resins, absorbent structures, and absorbent articles were measured by the following methods.

Used were samples (e.g. water-absorbent resins) as preserved in dampproof receptacles such as sealed polypropylene receptacles, and the following various measurements were carried out under conditions of a temperature of 20±1° C. and a relative humidity of 60±5%.

1. Capillary Absorption Capacity and Capillary Absorption Index:

As to the capillary absorption capacity and capillary absorption index in the present invention, the absorption abilities of a liquid between a water-absorbent resin and a liquid-diffusing member or liquid-acquiring member are measured under a load of 0.419 kPa (0.06 psi) within a predetermined time at 0 cm (equivalent water level) and at a negative pressure slope of 40 cm. The apparatus and method for measuring these capillary absorption abilities are mentioned with referring to FIGS. 1 and 2.

1-A. Capillary Absorption Ability at a Height of 40 cm (FIG. 1):

1) A introducing tube 3 is connected to a lower portion of a glass filter 2 (glass filter particle number: #3, Buchner type filter produced by Sogo Rikagaku Glass Seisakusho Co., Ltd., TOP17G-3 (Code No. 1175-03)) having a diameter of 60 mm and a liquid-absorbing face comprised of a porous glass plate 1, and then this introducing tube 3 is connected to a mouth as equipped in a lower portion of a liquid-storing receptacle 4 having a diameter of 10 cm. Then, the porous glass plate in the glass filter has an average porosity diameter of 20 to 30 μm. By the capillary action, water can be retained in the porous glass plate against a negative pressure of water column even in a state where the height difference between the liquid surfaces is 60 cm, and preserved is a state where air is not introduced. A supporting ring 5 for adjusting the height of glass filter 2 is put in, and the system is filled with a physiological saline 6 (a 0.9 weight % aqueous NaCl solution), and the liquid-storing receptacle is put on a balance 7. After confirming that there is no air in the introducing tube and at the lower portion of the porous glass plate in the glass filter, the glass filter is adjusted and fixed on a stand 8, so that the height difference between the liquid surface level of an upper portion of the physiological saline 6 in the liquid-storing receptacle and the level of an upper portion of the porous glass plate 1 will be 40 cm.

2) A measuring sample 9 (water-absorbent resin, liquid-diffusing member, or liquid-acquiring member) is put on the porous glass plate 1 under a condition as mentioned below, and a load 10 having a diameter of 59 min (0.06 psi) is further put thereon, and the value ($W_{40}$) of the physiological saline as absorbed by the measuring sample 9 is measured after 30 minutes.

When the measuring sample 9 is a water-absorbent resin: 0.44 g of the sample is uniformly and rapidly spread on the glass filter in the funnel.

When the measuring sample 9 is a liquid-diffusing member or liquid-acquiring member: a sample having a diameter of 57 mm and being circularly stamped out is prepared and put on the porous glass plate 1 after its weight (Wi) is measured in a drying state, and then it is measured.

Figure 2:
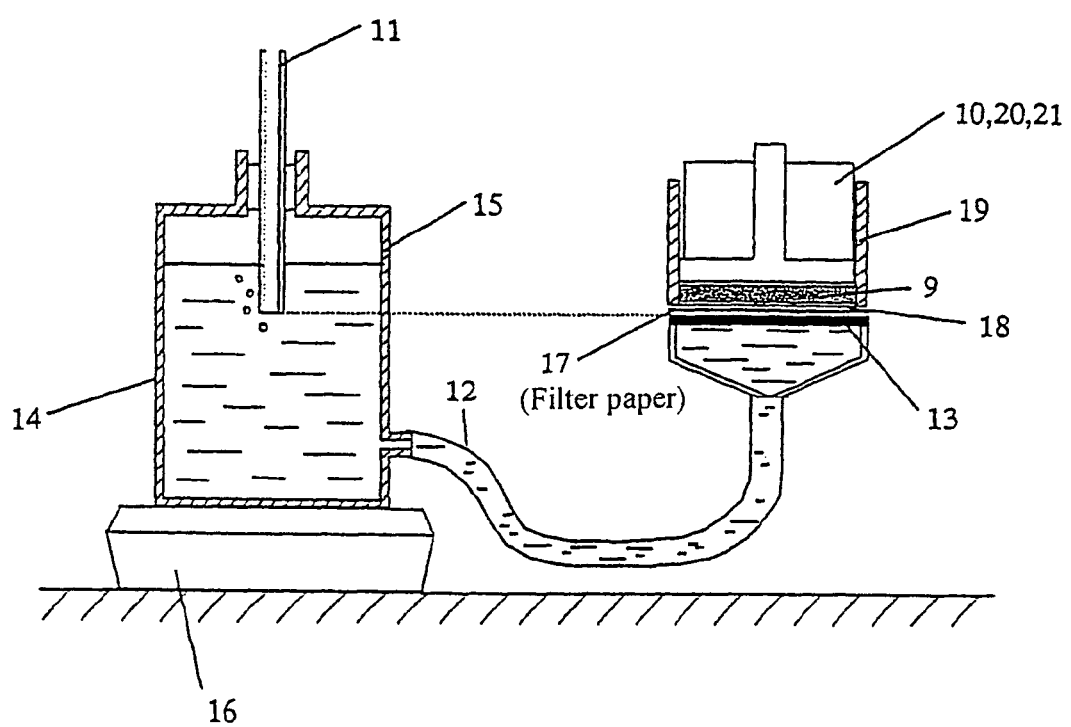
FIG. 2 is a schematic sectional view of a measurement apparatus as used for the measurement to determine the capillary absorption capacity and the capillary absorption index in the present invention. The capillary absorption capacity at a height of 0 cm and the absorption capacity of the water-absorbent resin under a load are measured with this apparatus.

1-B. Capillary Absorption Ability at a Height of 0 cm (FIG. 2):

A filter paper 17 was put on a glass filter 13 of a measurement apparatus equipped with an open-air-aspirating pipe 11, an introducing tube 12, a glass filter 13, a liquid-storing receptacle 15 for storing a physiological saline 14, and a balance 16 (where, the lower end of the open-air-aspirating pipe 11 sinks in the physiological saline, and the position of the glass filter 13 is fixed very slightly higher than the lower end of the open-air-aspirating pipe 11) as shown in FIG. 2. The entire surface of the filter paper 17 is in a wet condition with the physiological saline.

The measuring sample 9 is put on a wire net of a plastic cylinder 19 having a diameter of 60 mm wherein the bottom of the plastic cylinder 19 is attached by fusion to the wire net 18 of 400 mesh (mesh opening size: 38 μm) under the above condition, and further a liquid-absorbing instrument on which a load 10 (0.06 psi) having a diameter of 59 mm is mounted is prepared thereon. This liquid-absorbing instrument is put on the filter paper 17 on the glass filter 13, and the value ($W_0$) of the physiological saline as absorbed by the measuring sample 9 is measured after 30 minutes.

The capillary absorption capacities and capillary absorption indexes in the present invention are calculated in accordance with the following equations:

capillary absorption capacity $C$(g/g) of liquid-diffusing member at a height of 40 cm=absorption quantity ($W_{40}$)(g)/weight of measuring sample before absorbing a liquid(Wi)(g)   1)

capillary absorption capacity $G$(g/g) of liquid-acquiring member at a height of 40 cm=absorption quantity($W_{40}$)(g)/weight of measuring sample before absorbing a liquid(Wi)(g)   2)

capillary absorption capacity $D$(g/g) of water-absorbent resin at a height of 40 cm=absorption quantity($W_{40}$)(g)/0.44 (g)   3)

capillary absorption capacity(g/g) of liquid-diffusing member at a height of 0 cm=absorption quantity ($W_0$)(g)/weight of measuring sample before absorbing a liquid(Wi)(g)   4)

capillary absorption capacity(g/g) of liquid-acquiring member at a height of 0 cm=absorption quantity ($W_0$)(g)/weight of measuring sample before absorbing a liquid(Wi)(g)   5)

capillary absorption capacity(g/g) of water-absorbent resin at a height of 0 cm=absorption quantity ($W_0$)(g)/0.44 (g)   6)

capillary absorption index $A$ of liquid-diffusing member at a height of 40 cm=capillary absorption capacity $C$(g/g) of liquid-diffusing member at a height of 40 cm/capillary absorption capacity(g/g) of liquid-diffusing member at a height of 0 cm   7)

capillary absorption index $E$ of liquid-acquiring member at a height of 40 cm=capillary absorption capacity $G$(g/g) of liquid-acquiring member at a height of 40 cm/capillary absorption capacity(g/g) of liquid-acquiring member at a height of 0 cm   8)

capillary absorption index $B$ of water-absorbent resin at a height of 40 cm=capillary absorption capacity $D$(g/g) of water-absorbent resin at a height of 40 cm/capillary absorption capacity(g/g) of water-absorbent resin at a height of 0 cm   9)

2. Suction Height:

A liquid-diffusing member is prepared in a state where the liquid-diffusing member has a width of 2 cm and a length of 90 cm. The liquid-diffusing member is stood vertically at an angle of 90° in such a manner that the lower end of the liquid-diffusing member is immersed in a physiological saline by about 2 cm. The height of the liquid as absorbed is measured after 72 hours in such a manner that the liquid is not vaporized. The absorption capacity of the lower end (0 to 10 cm) of the liquid-diffusing member is referred to as 100, and the absorption capacity is each calculated by cutting the member 2 cm by 2 cm with a cutter knife in a direction of height, and the height displaying an absorption capacity that is 90% of the absorption capacity of the lower end is defined as a suction height of the liquid-diffusing member (cm).

3. Absorption Capacity:

About 0.20 g ($W_{p1}$) of water-absorbent resin was uniformly added to a nonwoven-fabric-made bag (60 mm×60 mm), and then the bag was immersed into a 0.9 weight % aqueous sodium chloride solution (physiological saline). The bag was putted up after 60 minutes, and the weight (Wa (g)) was measured after draining water off at 250 G for 3 minutes with a centrifugal separator. In addition, the same procedure was carried out without using any water-absorbing agent, and then the weight (Wb (g)) was measured. Then, the absorption capacity (g/g) of the water-absorbent resin was calculated from these Wa and Wb in accordance with the following equation:

absorption capacity(g/g)=[Wa(g)−Wb(g)]/weight $W_{p1}$ (g) of water-absorbent resin 4. Absorption Capacity Under Load:

The absorption capacity under a load was measured by using the same apparatus of FIG. 2 as of 1-B. The load 20 and the load 21 as adjusted were prepared so that the weight will be each increased instead of the load 10, and the pressure will be 2.07 kPa (0.3 psi) and 4.83 kPa (0.7 psi). About 0.44 g ($W_{p2}$) of water-absorbent resin was spread on a wire net 18 of 400 mesh (mesh opening size: 38 μm) as attached by fusion to the bottom of a plastic cylinder 19 of a diameter 60 mm, and further a liquid-absorbing instrument on which the load 20 (2.07 kPa (0.3 psi)) or the load 21 (4.83 kPa (0.7 psi)) was mounted was put on the filter paper 17 on the glass filter 13 in FIG. 2, and then the value ($W_c$) of the physiological saline as absorbed by the absorbent resin was measured after 30 minutes. Then, the absorption capacity (g/g) under a load of 2.07 kPa (0.3 psi) or 4.83 kPa (0.7 psi) each was calculated in accordance with the following equation:

$$\text{absorption capacity(g/g)under load} = W_c/W_{p2}$$

5. Particle Diameter Distribution and Weight-Average Particle Diameter:

Water-absorbent resins were classified with sieves having mesh opening sizes of such as 850 μm, 600 μm, 500 μm, 300 μm, 150 μm, 75 μm, and 45 μm (if necessary, JIS standard sieves are further added), and then the percentages of the residues R on these sieves were plotted on logarithmic probability paper. Therefrom, the particle diameter corresponding to R=50% was defined as a weight-average particle diameter.

6. Liquid Distribution Ratio from Liquid-Diffusing Member to Water-Absorbent Resin:

After a liquid-diffusing member is cut to have a circular shape with a diameter of 57 mm, the liquid-diffusing member was beforehand dried and weighed out (Wd) (g). Thereafter, this liquid-diffusing member was immersed into a sufficient amount of a physiological saline (0.9 weight % aqueous NaCl solution). The sample as swollen by absorbing a liquid was taken out from a receptacle, and a portion of the sample was supported, and the sample was pulled for 1 minute to drain the liquid off. Thereafter, the weight (We (g)) of the sample that absorbed the liquid was measured at once.

On the liquid-diffusing member after draining the liquid off above, 0.44 g of water-absorbent resin was uniformly scattered, thus producing an absorbent structure. The weight (Wf) (g) of the liquid-diffusing member was measured again after contacting the water-absorbent resin for 30 minutes under a load of 0.41 kPa (0.06 psi), and then the liquid distribution ratio from the liquid-diffusing member of the absorbent structure was calculated in accordance with the following equation:

$$\text{liquid distribution ratio}(\%) = (We - Wf)/(We - Wd) \times 100$$

7. Production Example of Absorbent Structure and Absorbent Article Comprising Liquid-Diffusing Member, and Evaluation of Performance of Absorbent Article (Model Diaper):

About 14 g of water-absorbent resin was uniformly scattered on Haetlon paper (produced by Teikoku Pulp Industry, GSP-22, and weight per unit area: 22.4 g/m²) in a range of 11×38 cm. Thereafter, the water-absorbent resin was sprayed with 5 to 10 weight % of deionized water to moisturize it, and then the water-absorbent resin was molded to form a sheet. After the above sheet was dried by allowing to stand overnight, various liquid-diffusing members having a size of 11×38 cm were laminated thereon, and the whole was wrapped with a surplus portion of the Haetlon paper, thus preparing the present invention absorbent structure comprising the liquid-diffusing members and the water-absorbent resin.

Figure 3:
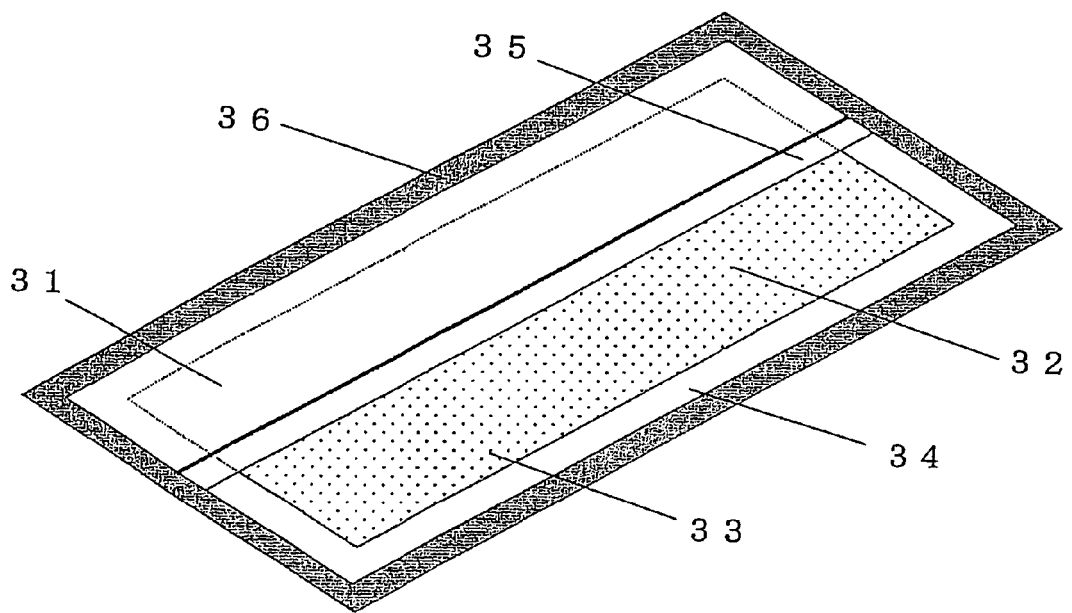
FIG. 3 is a schematic perspective view of an absorbent article according to the present invention.
Figure 4:
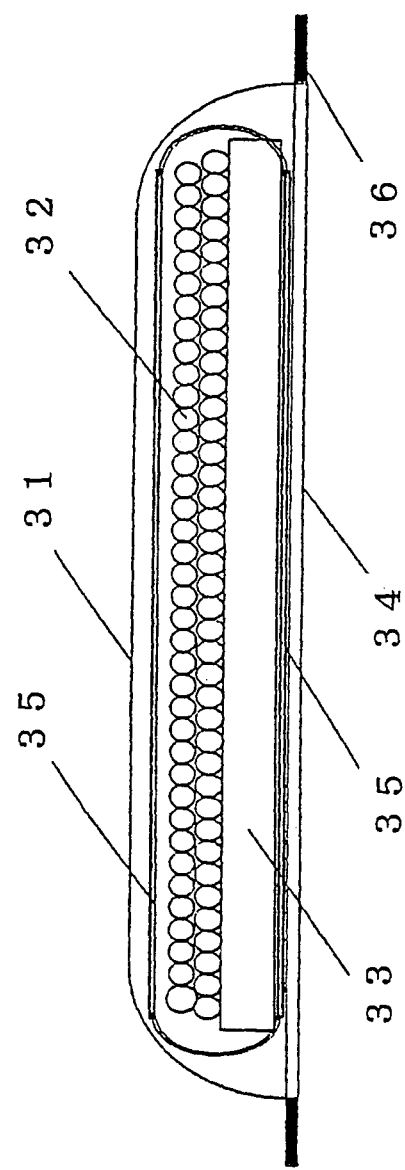
FIG. 4 is a schematic sectional view of an absorbent article according to the present invention.

On a liquid-impermeable rectangular polyethylene film (weight per unit area: 18 g/m²) having a size of 12×40 cm, the above absorbent structure was put in such a manner that the liquid-diffusing members were upper portions. Then, a liquid-permeable polyester nonwoven fabric having a size of 12×40 cm was laminated thereon, and its sides were stuck with a tape, thus producing an absorbent article (model diaper) (FIGS. 3 and 4).

A poly(vinyl chloride) tube having a diameter of 14.7 cm and a length of 46 cm was cut half in the vertical direction, and plates having a size of 20×30 cm were stuck to both ends of the resultant half cylinder in the horizontal direction to prepare a U-shaped instrument. This U-shaped instrument was arranged in a state where the instrument was angled at 90° (shape of ⊂), and then the above model diaper was fixed therein. This state is assumption of a state where a child sleeps on his face and wears the diaper. This diaper was kept at 37° C. together with the above instrument, and 50 cc of a physiological saline continued to be added at an interval of 20 minutes from the center of the diaper in this state assuming sleep-on-face until the leakage was caused.

When the leakage was caused, the diaper was taken out, and the followings were calculated: a liquid diffusion ratio of the liquid-diffusing member (%), a total absorption quantity of the diaper when the leakage is caused (final weight of diaper–weight of diaper before absorbing a liquid) (g), a liquid absorption quantity of the water-absorbent resin in the diaper (g), and a liquid absorption quantity of the water-absorbent resin in an upper half portion of the diaper (at a side assuming sleep-on-face) (g).

8. Production Example of Absorbent Structure and Absorbent Article Comprising Liquid-Acquiring Member, and Evaluation Method for Performance of Absorbent Article:

On a rectangular polyethylene film (weight per unit area: 18 g/m²) having a size of 14×40 cm as a liquid-impermeable back sheet, 16.4 g of water-absorbent resin was scattered over an area of 12×38 cm (scattering amount of water-absorbent resin: 360 g/m²). In consideration of a urination position, a liquid-acquiring member having a size of 8×24 cm (weight per unit area: 160 g/m²) was laminated at a position as slightly shifted from its center, thus composing an absorbent structure.

Then, a liquid-permeable polyester nonwoven fabric having a size of 12×40 cm was put thereon, thus producing a model absorbent article.

The above absorbent article was fixed flat on a desk, and an acrylic plate of 12×40 cm (equipped with a cylinder having a diameter of 70 mm in a central portion in order to inject a liquid) and a load of 1.3 kg were put thereon.

Into the cylinder, 75 ml of a physiological saline of which the temperature was adjusted to 37° C. was injected. Measured were how long time passed until the liquid completed being absorbed from the surface sheet into the absorbent article (liquid-absorbing time), and how long time passed until the liquid was absorbed from the liquid-permeable surface material to the liquid-acquiring member or the water-absorbent resin, and air entered a neighboring surface of the liquid-permeable surface material, and then the surface of the surface material was white (whitening time).

After 60 minutes passed, the liquid-acquiring member was taken out from the absorbent article, and its weight was measured. The residual liquid amount in the liquid-acquiring member was calculated by subtracting the value from the original weight of the liquid-acquiring member. After the measurement, the liquid-acquiring member was returned to the original absorbent article.

Furthermore, these procedures were repeated every 60 minutes four times in total. After 60 minutes subsequent to the fourth injection, the acrylic plate was removed, and the weight of the liquid-acquiring member was measured and returned to the absorbent article. Thereafter, the absorbent article was covered with a pile including 15 sheets of kitchen paper (Oji Seishi Co., Ltd., Nepia, 46×22 cm), and a load of 12 kg (including an acrylic plate of 14×40 cm) was applied thereto for a minute, and the amount of the liquid as returned to the kitchen paper (the amount of wet back of the aqueous liquid) was measured.

In addition, after 60 minutes subsequent to the fourth injection, the liquid diffusion area from the upper portion of the liquid-permeable surface material into the absorbent core was measured (S cm$^2$).

The diffusion area in the present absorbent article was calculated in accordance with the following equation:

$$\text{diffusion area(\%)} = \text{liquid diffusion area}(S\, \text{cm}^2)/\text{area of absorbent structure}(12\times 38\, \text{cm}).$$

9. Space Ratio and Average Space Radius of Water-Absorbent Resin as to Spaces Between Particles when Being Saturation-Swollen, and Space Ratio and Average Space Radius of Water-Absorbent Resin Particles when being Saturation-Swollen:

The space ratio and the average space radius of the water-absorbent resin and the water-absorbent resin particles when being saturation-swollen were measured by using the measurement apparatus as shown in FIG. 1

The height h where a liquid rises in a tube having a radius R by capillary action is represented as $h = 2\gamma \cos\theta/\rho g R$ when the capillary action of the liquid, contact angle, acceleration of gravity, and density of the liquid are referred to as $\gamma$, $\theta$, $g$, and $\rho$, respectively (this equation was induced from both the equation (2) $p = 2\gamma \cos\theta/Rc$ (Laplace equation) in page 36 and the equation (5) Leq=p/$\rho$g in page 37 of "ABSORBENCY" (ELSEVIER) edited by P. K. Chatterjee, and "Leq" and "Rc" were described as "h" and "R" respectively). The head difference between a tank and a measuring cell in the apparatus of FIG. 1 is lifted from 0 to h (cm). Thereby, among the liquid existing in a swollen gel or absorbent structure between its gel particles or spaces of the absorbent structure, space water preserved in R ($\mu$m) that is a larger radius than a capillary radius (space) is discharged and gets away. Accordingly, a saturation-swollen gel of which the spaces are completely filled with a liquid rises from a height of 0 cm, and the remaining amount of the liquid as to spaces is measured each at a predetermined height, thus obtaining the distribution of the space radius (capillary radius) in the swollen gel.

Hereinafter, in the present invention, the value of the capillary radius R of a sample as calculated at an individual height h by using the equation $h = 2\gamma \cos\theta/\rho g R$ is defined as a space radius of the sample. The head difference between the tank and the measuring cell is lifted from 0 to 60 (cm), stepwise to 1 cm, 2 cm, 5 cm, 10 cm, 20 cm, 30 cm, and 60 cm. Thereby, a liquid as preserved in a space having a R value that corresponds to each height is discharged. The distribution of the space radius (capillary radius) of the sample can be calculated by measuring this amount of the liquid as discharged, and the values are plotted on logarithmic probability paper, and then the value of d50 is defined as an average space radius.

In the equation $h = 2\gamma \cos\theta/\rho g R$ in the present examples, the following values are used: capillary action $\gamma$(0.0728 N/m) of a physiological saline (a 0.9 weight % aqueous NaCl solution); contact angle $\theta$(0°); density $\rho$(1,000 kg/m$^3$) of physiological saline; and acceleration of gravity g (9.8 n/s$^2$). In this way, it is calculated that the liquids as preserved at positions of 1 cm, 2 cm, 5 cm, 10 cm, 20 cm, 30 cm, and 60 cm are preserved at space radiuses (capillary radiuses) of 1,485, 743, 297, 149, 74.3, 49.5, and 24.8, respectively.

10. Space Ratio and Average Space Radius without Load:

1) A introducing tube 3 is connected to a lower portion of a glass filter 2 having a diameter of 60 mm, which is equipped with a liquid-absorbing face comprised of a porous glass plate 1 (having a glass filter particle number of #3 and an average porosity diameter of about 20 to about 30$\mu$, and not introducing air in a state where there is a height difference of 60 cm). This introducing tube 3 is connected to a mouth as equipped in a lower portion of a liquid-storing receptacle 4 having a diameter of 10 cm. A supporting ring 5 for adjusting the height of glass filter 2 is put in, and the system is filled with a physiological saline 6 and the liquid-storing receptacle is put on a balance 7. After confirming that there is no air in the introducing tube and at the lower portion of the porous glass plate in the glass filter, the glass filter is adjusted and fixed on a stand 8 so that the height difference between the liquid surface level of an upper portion of the physiological saline 6 in the liquid-storing receptacle and the level of an upper portion of the porous glass plate 1 will be 60 cm, and then the value of the balance is adjusted to 0.

2) A measuring sample 9 (water-absorbent resin, liquid-diffusing member, or liquid-acquiring member) is put on the porous glass plate 1 under a condition as mentioned below.

When the measuring sample 9 is a water-absorbent resin: about 0.9 g (W) of the sample is uniformly and rapidly scattered over the glass filter.

When the measuring sample 9 is an absorbent structure: a sample having a diameter of 57 mm and being circularly stamped out is prepared, and put on the porous glass plate 1 after its weight (W) is measured in a drying state, and then it is measured.

3) The height difference between the liquid surface of the upper portion of the physiological saline 6 in the liquid-storing receptacle 4 and the level of the upper portion in the porous glass plate 1 is adjusted to $-3$ cm (the porous glass plate 1 is arranged lower), and the sample is swollen for 20 minutes. Then, the sample is made to have a condition where the sample is perfectly immersed in the physiological saline and has no air bubble.

4) The height difference between the liquid surface of the upper portion of the physiological saline 6 in the liquid-storing receptacle 4 and the level of the upper portion in the porous glass plate 1 is adjusted to 0 cm, and the sample is allowed to stand for 40 minutes in order to carrying out saturation and swelling, and then the value of the balance is recorded (A0). Incidentally, the time may be prolonged if the sample is not saturation-swollen for 40 minutes.

5) The height difference between the liquid surface of the upper portion of the physiological saline 6 in the liquid-storing receptacle 4 and the level of the upper portion in the porous glass plate 1 is adjusted to 1 cm, and the value of the balance is recorded after 7 minutes (A1). Depending upon the space radius of the sample, there is a case where the equilibrium time until this space water is discharged is favorably prolonged.

6) Similarly, the height difference between the liquid surface of the upper portion of the physiological saline 6 in the liquid-storing receptacle 4 and the level of the upper portion in the porous glass plate 1 is raised to 2 cm, 5 cm, 10 cm, 20 cm, 30 cm and 60 cm, and then and the value of the balance is each recorded after 7 minutes (A2, A5, A10, A20, A30, and A60).

7) In order to perfectly remove space water as preserved at a height difference of 60 cm between the liquid surface of the upper portion of the physiological saline 6 in the liquid-storing receptacle 4 and the level of the upper portion in the porous glass plate 1, the sample was taken out, and the water is drained off (250 G, and 6 minutes) with a centrifugal separator, and then the weight B is measured.

8) The value (A0−B) is an amount of the total space water in the sample, the values as obtained by subtracting the respective B value from the values (A1, A2, A5, A10, A20, A30, and A60) are accumulated amounts of space water at heights of 1 cm, 2 cm, 5 cm, 10 cm, 20 cm, 30 cm and 60 cm. As is mentioned above, it is calculated that the liquids as preserved at positions of 1 cm, 2 cm, 5 cm, 10 cm, 20 cm, 30 cm, and 60 cm are preserved at space radiuses (capillary radiuses) of 1,485, 743, 297, 149, 74.3, 49.5, and 24.8 μm, respectively. Therefore, the percentage of the accumulated amount of space water relative to the amount of the total space water (A0−B) is calculated at each height, and then this value and the above capillary radius are plotted on logarithmic probability paper (for example, the value (A2−B) (A0−B)×100 is plotted on 743 μm in the graph). The value of the space radius corresponding to 50% of the accumulated space amount (d50) is determined and defined as an average space radius (μm) of the sample.

9) The space ratio of the sample is calculated in accordance with the following equation:

Space ratio=$(A0-B)/\{A0+W/(\text{absolute density of sample})\} \times 100$

10) In order to further confirm a measured value, the average space radius was determined by this method in a condition that spherical glass beads of 350 to 500 μm and those of 1,000 to 1,180 μm were used as standard samples. Then, the radiuses as determined were 86 μm and 217 μm respectively.

Referential Example 1

Production Process for Water-Absorbent Resin (1)

An aqueous monomer solution having a monomer concentration of 35 weight % and a neutralization ratio of 75% was obtained by using 21.6 parts of acrylic acid, 228.6 parts of 37 weight % aqueous sodium acrylate solution, 0.0185 part of N, N'-methylenebisacrylamide (0.01 mol % relative to monomer), 0.106 part of hydroxyethyl cellulose, and 53 parts of deionized water. Then, 0.09 part of potassium persulfate was dissolved in this aqueous monomer solution, and a nitrogen gas was blown thereto to remove dissolved oxygen.

In a four-necked separable flask as fitted with a stirrer, a reflux condenser, a thermometer, a tube for introducing a nitrogen gas, and a dropping funnel, 800 parts of cyclohexane was weighed out, and 4 parts of a sucrose fatty acid ester (HLB=6) was added thereto and dissolved, and then a nitrogen gas was blown thereto to remove dissolved oxygen. Subsequently, the aqueous monomer solution was added to the above separable flask while being stirred, and then it was dispersed. Thereafter, the bath temperature was raised to 65° C. in order to start a polymerization reaction. Thereafter, this temperature was maintained for 2 hours, and then the polymerization was completed. After the end of the polymerization, a large portion of water was removed by azeotropic dehydration. Thereafter, the resultant reaction solution was filtrated and dried under a reduced pressure at 100° C., thus obtaining a resin having a water content of 8%. In a stainless-steel-made beaker, 100 parts of the resin as obtained was blended with 0.1 part of ethylene glycol diglycidyl ether, 3 parts of water, and 1 part of isopropanol, and the resultant mixture was heat-treated at 120° C. for 30 minutes. Thereafter, the resultant particles were transferred to the same separable flask as of that mentioned above, and methanol having an amount (weight) that was 5 times larger than that of the particles was added thereto, and the resultant mixture was stirred at 60° C. for 10 minutes. Subsequently, the mixture was filtrated with a filter paper to separate the particles, and thereafter the particles were dried at 60° C. for 2 hours under a reduced pressure of 50 to 100 mmHg, thus obtaining a water-absorbent resin (1). The water-absorbent resin (1) had a weight-average particle diameter of 105 μm. In addition, the water-absorbent resin displayed a capillary absorption capacity of 45.5 (g/g) at a height of 0 cm, a capillary absorption capacity D of 27.4 (g/g) at a height of 40 cm, and a capillary absorption index B of 0.60 at a height of 40 cm.

Referential Example 2

Production Process for Water-Absorbent Resin (2)

A reaction liquid was obtained by dissolving 5 parts of polyethylene glycol diacrylate (n=8) into 5,500 parts of aqueous sodium acrylate solution having a monomer concentration of 33 weight % (neutralization ratio: 75 mol %/o). Next, this reaction liquid was deaerated under an atmosphere of nitrogen for 30 minutes. Subsequently, the above reaction liquid was supplied to a jacketed stainless-steel-made twin-arm kneader having: an lid that can be opened and shut; and two sigma type blades, and the system was replaced with a nitrogen gas while the reaction liquid was maintained at 30° C. Subsequently, 2.4 parts of ammonium persulfate and 0.12 part of L-ascorbic acid were added thereto while the reaction liquid was stirred, and then the polymerization was started after about one minute. Then, the polymerization was carried out at 30 to 90° C. After 60 minutes from the start of the polymerization, the resultant hydrogel polymer was taken out.

The crosslinked hydrogel polymer as obtained was in finely divided pieces having a diameter of about 5 mm. This finely divided crosslinked hydrogel polymer was spread on a wire net having 50 mesh, and hot-wind-dried at 150° C. for 90 minutes. Subsequently, the resultant dry material was pulverized with a vibration mill, and further classified with a wire net having 20 mesh, thus obtaining an unshaped pulverized resin having a weight-average particle diameter of 360 μm, in which the ratio of particles having particle diameters of smaller than 106 μm was 3 weight %.

Into 100 parts of the resin as obtained, a surface-crosslinking agent solution including 0.05 part of ethylene glycol diglycidyl ether, 0.75 part of glycerin, 3 parts of water, 0.3 part of lactic acid, and 1 part of isopropyl alcohol was blended. The above mixture was heat-treated at 195° C. for 40 minutes, thus obtaining a water-absorbent resin (2'). The water-absorbent resin (2') as obtained was passed through a wire net having a mesh opening size of 250 μm, thus obtaining a water-absorbent resin (2) under the sieve. The water-absorbent resin (2) had a weight-average particle diameter of 120 μm. In addition, the water-absorbent resin displayed a capillary absorption capacity of 33.8 (g/g) at a height of 0 cm, a capillary absorption capacity D of 19.4 (g/g) at a height of 40 cm, and a capillary absorption index B of 0.57 at a height of 40 cm. As to the particle diameter distribution of the water-absorbent resin (2), the ratio of particles having particle diameters of 150 to 850 μm, and that of particles having particle diameters of not larger than 150 μm were 31% and 69% respectively.

Referential Example 3

Production Process for Water-Absorbent Resin (3)

A reaction liquid was obtained by dissolving 8.1 parts of polyethylene glycol diacrylate (n=8) into 5,500 parts of aqueous sodium acrylate solution having a monomer concentration of 38 weight % (neutralization ratio: 71 mol %). Next, this reaction liquid was deaerated under an atmosphere of nitrogen for 30 minutes. Subsequently, the above reaction liquid was supplied to a jacketed stainless-steel-made twin-arm kneader having: an lid that can be opened and shut; and two sigma type blades, and the system was replaced with a nitrogen gas while the reaction liquid was maintained at 30° C. Subsequently, 2.4 parts of ammonium persulfate and 0.12 part of L-ascorbic acid were added thereto while the reaction liquid was stirred, and then the polymerization was started after about one minute. Then, the polymerization was carried out at 20 to 95° C. After 60 minutes from the start of the polymerization, the resultant hydrogel polymer was taken out.

The crosslinked hydrogel polymer as obtained was in finely divided pieces having a diameter of about 5 mm. This finely divided crosslinked hydrogel polymer was spread on a wire net having 50 mesh, and hot-wind-dried at 150° C. for 90 minutes. Subsequently, the resultant dry material was pulverized with a vibration mill, thus obtaining an unshaped pulverized resin having a weight-average particle diameter of 400 μm, which was further passed through a sieve having a mesh opening size of 850 μm and left on a sieve having a mesh opening size of 106 μm.

Into 100 parts of the resin as obtained, a surface-crosslinking agent solution including 0.3 part of 1,4-butanediol, 0.5 part of propylene glycol, and 3 parts of water was blended. The above mixture was heat-treated at 210° C. for 30 minutes, thus obtaining a water-absorbent resin (3). The water-absorbent resin (3) had a weight-average particle diameter of 420 μm. In addition, the water-absorbent resin displayed a capillary absorption capacity of 37.8 (g/g) at a height of 0 cm, a capillary absorption capacity D of 4.30 (g/g) at a height of 40 cm, and a capillary absorption index B of 0.11 at a height of 40 cm. As to the particle diameter distribution of the water-absorbent resin (3), the ratio of particles having particle diameters of 150 to 850 μm, and that of particles having particle diameters of not larger than 150 μm were 95% and 5% respectively.

Referential Example 4

Production Process for Liquid-Diffusing Member (1)

A liquid-diffusing member comprised of a porous crosslinked polymer was produced by using a high-internal-phase water-in-oil-type emulsion (HIPE). As to a water phase for forming the HIPE, 20.7 parts of anhydrous calcium chloride and 0.415 part of potassium persulfate were dissolved in 394 parts of pure water. Separately, 0.654 part of diglycerol monooleate was added to a mixture including 0.438 part of styrene, 5.449 parts of 2-ethylhexyl acrylate, and 3.459 parts of 55% divinylbenzene, thus obtaining an oil phase. The water phase and the oil phase were continuously supplied to a blending apparatus having two pin type stirring blades, at 80° C. at a feeding rate of 75.2 cm$^3$/s, and at 22° C. at a feeding rate of 1.88 g/s, respectively. They were blended with stirring at 1,600 rpm, thus obtaining a high-internal-phase water-in-oil-type emulsion having a temperature of 79° C.

The high-internal-phase water-in-oil-type emulsion as obtained was molded on a driving belt covered with a PET film to obtain a thickness of 5 mm, and the resultant upper face was further covered with a PET film. Through the resultant molded product, a curing furnace of which the internal temperature was adjusted to 95° C. was passed at a moving rate of 1.5 m/min to polymerize the molded product for 10 minutes, thus obtaining a porous crosslinked polymer in a wet condition. This wet porous crosslinked polymer was dehydrated and dried until its water content was adjusted to 20%, thus obtaining a liquid-diffusing member (1) comprised of the porous crosslinked polymer having a thickness of 1 mm. The liquid-diffusing member (1) displayed a capillary absorption capacity of 33.6 (g/g) at a height of 0 cm, a capillary absorption capacity C of 14.2 (g/g) at a height of 40 cm, and a capillary absorption index A of 0.42 at a height of 40 cm. In addition, the liquid-diffusing member (1) displayed a suction height of 45 cm.

Referential Example 5

Production Process for Liquid-Diffusing Member (2)

A liquid-diffusing member (2) having a water content of 22% and a thickness of 1 mm was obtained by the similar procedure except that the oil phase as used in the production process for the liquid-diffusing member (1) was changed to an oil phase obtained by adding 0.654 part of diglycerol monooleate to a mixture including 1.649 parts of styrene, 5.449 parts of 2-ethylhexyl acrylate, and 2.248 parts of 55% divinylbenzene. The liquid-diffusing member (2) displayed a capillary absorption capacity of 27.0 (g/g) at a height of 0 cm, a capillary absorption capacity C of 7.6 (g/g) at a height of 40 cm, and a capillary absorption index A of 0.28 at a height of 40 cm. In addition, the liquid-diffusing member (2) displayed a suction height of 35 cm.

Referential Example 6

Production Process for Liquid-Diffusing Member (3)

A cotton pulp used for disposable diapers for children was wet and compressed after aspiration, thus obtaining a laminated liquid-diffusing member (3) having a density of 0.03 g/cm$^3$ and a weight per its unit area of 260 g/m$^2$. The liquid-diffusing member (3) displayed a capillary absorption capacity of 6.6 (g/g) at a height of 0 cm, a capillary absorption capacity C of 2.1 (g/g) at a height of 40 cm, and a capillary absorption index A of 0.32 at a height of 40 cm. In addition, the liquid-diffusing member (3) displayed a suction height of 30 cm.

Referential Example 7

Production Process for Liquid-Diffusing Member (4)

A cotton pulp used for disposable diapers for children (density: 0.03 g/cm$^3$, and weight per unit area: 260 g/m$^2$) was used as a liquid-diffusing member (4). The liquid-diffusing member (4) displayed a capillary absorption capacity of 13.7 (g/g) at a height of 0 cm, a capillary absorption capacity C of 0.5 (g/g) at a height of 40 cm, and a capillary absorption index A of 0.04 at a height of 40 cm. In addition, the liquid-diffusing member (4) displayed a suction height of lower than 10 cm.

Example 1

An absorbent structure (1) was obtained by combining the water-absorbent resin (1) with the liquid-diffusing member (1) according to the method as mentioned in Production Examples of the absorbent structure and absorbent article comprising the liquid-diffusing member. The capillary absorption indexes and capillary absorption capacities of the water-absorbent resin (1) and the liquid-diffusing member (1) as comprised in the above absorbent structure were as shown in each Referential Example. The B/A (ratio of the capillary absorption index B of the water-absorbent resin (1) at a height of 40 cm to the capillary absorption index A of the liquid-diffusing member (1) at a height of 40 cm) was 1.4, and the D/C (ratio of the capillary absorption capacity D of the water-absorbent resin (1) at a height of 40 cm to the capillary absorption capacity C of the liquid-diffusing member (1) at a height of 40 cm) was 1.9.

The liquid distribution ratio from the liquid-diffusing member to the water-absorbent resin was determined by using the absorbent structure (1), and further an absorbent article (1) was produced as a model diaper by using the absorbent structure (1), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 1, and very excellent values were shown therein because the liquid distribution ratio from the liquid-diffusing member to the water-absorbent resin, and the liquid absorption ability of the water-absorbent resin from the liquid-diffusing member in a half upper portion of the diaper assumed sleep-on-face were 47% and 165 g respectively.

Example 2

An absorbent structure (2) was obtained by combining the water-absorbent resin (2) with the liquid-diffusing member (1). The B/A (ratio of the capillary absorption index B of the water-absorbent resin (2) at a height of 40 cm to the capillary absorption index A of the liquid-diffusing member (1) at a height of 40 cm) was 1.4, and the D/C (ratio of the capillary absorption capacity D of the water-absorbent resin (2) at a height of 40 cm to the capillary absorption capacity C of the liquid-diffusing member (1) at a height of 40 cm) was 1.4.

The liquid distribution ratio from the liquid-diffusing member to the water-absorbent resin was determined by using the absorbent structure (2), and further an absorbent article (2) was produced as a model diaper by using the absorbent structure (2), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 1, and very excellent values were shown therein because the liquid distribution ratio from the liquid-diffusing member to the water-absorbent resin, and the liquid absorption ability of the water-absorbent resin from the liquid-diffusing member in a half upper portion of the diaper assumed sleep-on-face were 23% and 102 g respectively.

Comparative Example 1

An absorbent structure (3) was obtained by combining the water-absorbent resin (3) with the liquid-diffusing member (1). The B/A (ratio of the capillary absorption index B of the water-absorbent resin (3) at a height of 40 cm to the capillary absorption index A of the liquid-diffusing member (1) at a height of 40 cm) was 0.3, and the D/C (ratio of the capillary absorption capacity D of the water-absorbent resin (3) at a height of 40 cm to the capillary absorption capacity C of the liquid-diffusing member (1) at a height of 40 cm) was 0.3.

The liquid distribution ratio from the liquid-diffusing member to the water-absorbent resin was determined by using the absorbent structure (3), and further an absorbent article (3) was produced as a model diaper by using the absorbent structure (3), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 1, but the liquid distribution ratio from the liquid-diffusing member to the water-absorbent resin, and the liquid absorption ability of the water-absorbent resin from the liquid-diffusing member in a half upper portion of the diaper assumed sleep-on-face were 13% and 33 g respectively.

From Examples 1 and 2 and Comparative Example 1, it would be understood that even if the same liquid-diffusing members are used, the liquid distribution ratio is different and the absorbency of the water-absorbent resin in the diaper are greatly different between absorbent structures in which the relationship with the capillary absorption ability of the water-absorbent resin satisfies the present invention relationship or not.

Example 3

A liquid-diffusing member (1') having a thickness of about 0.5 mm was obtained by slicing up the liquid-diffusing member (1) so that the thickness of the liquid-diffusing member (1') will be a half thickness of the liquid-diffusing member (1), and an absorbent structure (4) was obtained by combining the water-absorbent resin (1) therewith. The B/A (ratio of the capillary absorption index B of the water-absorbent resin (1) at a height of 40 cm to the capillary absorption index A of the liquid-diffusing member (1') at a height of 40 cm) was 1.9, and the D/C (ratio of the capillary absorption capacity D of the water-absorbent resin (1) at a height of 40 cm to the capillary absorption capacity C of the liquid-diffusing member (1') at a height of 40 cm) was 2.2. The weight ratio of the water-absorbent resin was 80 weight % relative to the total weight of the water-absorbent resin and the liquid-diffusing member.

The liquid distribution ratio from the liquid-diffusing member to the water-absorbent resin was determined by using the absorbent structure (4), and further an absorbent article (4) was produced as a model diaper by using the absorbent structure (4), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 1, and very excellent values were shown therein because the liquid distribution ratio from the liquid-diffusing member to the water-absorbent resin, and the liquid absorption ability of the water-absorbent resin from the liquid-diffusing member in a half upper portion of the diaper assumed sleep-on-face were 52% and 81 g respectively.

From Examples 1 and 3 and Comparative Example 4, although the amount of the member as used in the absorbent article (3) obtained by further decreasing the amount of the liquid-diffusing member from the absorbent article (1) is decreased by 30% of that in the diaper of Comparative Example 4 on the market at present, the total liquid absorption quantity is yet still in a high level. The design of further lighter and thinner diapers can be carried out by using the present invention absorbent structure in this way.

Example 4

An absorbent structure (5) was obtained by combining the water-absorbent resin (1) with the liquid-diffusing member (2). The B/A (ratio of the capillary absorption index B of the water-absorbent resin (1) at a height of 40 cm to the capillary absorption index A of the liquid-diffusing member (2) at a height of 40 cm) was 2.1, and the D/C (ratio of the capillary absorption capacity D of the water-absorbent resin (1) at a height of 40 cm to the capillary absorption capacity C of the liquid-diffusing member (2) at a height of 40 cm) was 3.6.

The liquid distribution ratio from the liquid-diffusing member to the water-absorbent resin was determined by using the absorbent structure (5), and further an absorbent article (5) was produced as a model diaper by using the absorbent structure (5), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 1, and very excellent values were shown therein because the liquid distribution ratio from the liquid-diffusing member to the water-absorbent resin, and the liquid absorption ability of the water-absorbent resin from the liquid-diffusing member in a half upper portion of the diaper assumed sleep-on-face were 51% and 77 g respectively. In this case, the amount of the member as used for diapers can be decreased, and thinner diapers having excellent performance can be produced.

Comparative Example 2

An absorbent structure (6) was obtained by combining the water-absorbent resin (3) with the liquid-diffusing member (2). The B/A (ratio of the capillary absorption index B of the water-absorbent resin (3) at a height of 40 cm to the capillary absorption index A of the liquid-diffusing member (2) at a height of 40 cm) was 0.4, and the D/C (ratio of the capillary absorption capacity D of the water-absorbent resin (3) at a height of 40 cm to the capillary absorption capacity C of the liquid-diffusing member (2) at a height of 40 cm) was 0.6.

The liquid distribution ratio from the liquid-diffusing member to the water-absorbent resin was determined by using the absorbent structure (6), and further an absorbent article (6) was produced as a model diaper by using the absorbent structure (6), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 1, but they were low because the liquid distribution ratio from the liquid-diffusing member to the water-absorbent resin, and the liquid absorption ability of the water-absorbent resin from the liquid-diffusing member in a half upper portion of the diaper assumed sleep-on-face were 13% and 17 g respectively.

Also from Example 4 and Comparative Example 2, it would be understood that the liquid distribution ratio from the liquid-diffusing member to the water-absorbent resin and the absorption amount of the water-absorbent resin in the diaper are greatly different between absorbent structures which comprise the same liquid-diffusing member but in which the relationship with the capillary absorption ability of the water-absorbent resin satisfies the present invention relationship or not.

Example 5

An absorbent structure (7) was obtained by combining the water-absorbent resin (1) with the liquid-diffusing member (3). The B/A (ratio of the capillary absorption index B of the water-absorbent resin (1) at a height of 40 cm to the capillary absorption index A of the liquid-diffusing member (3) at a height of 40 cm) was 1.9, and the D/C (ratio of the capillary absorption capacity D of the water-absorbent resin (1) at a height of 40 cm to the capillary absorption capacity C of the liquid-diffusing member (3) at a height of 40 cm) was 13.0.

The liquid distribution ratio from the liquid-diffusing member to the water-absorbent resin was determined by using the absorbent structure (7), and further an absorbent article (7) was produced as a model diaper by using the absorbent structure (7), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 2, and very excellent values were shown therein because the liquid distribution ratio from the liquid-diffusing member to the water-absorbent resin, and the liquid absorption ability of the water-absorbent resin from the liquid-diffusing member in a half upper portion of the diaper assumed sleep-on-face were 87% and 121 g respectively. However, the total absorption amount of the diaper was slightly low because the capillary absorption capacity of the liquid-diffusing member (3) was 6.6 (g/g) at a height of 0 cm.

Example 6

An absorbent structure (8) was obtained by combining the water-absorbent resin (2) with the liquid-diffusing member (3). The B/A (ratio of the capillary absorption index B of the water-absorbent resin (2) at a height of 40 cm to the capillary absorption index A of the liquid-diffusing member (3) at a height of 40 cm) was 1.8, and the D/C (ratio of the capillary absorption capacity D of the water-absorbent resin (2) at a height of 40 cm to the capillary absorption capacity C of the liquid-diffusing member (3) at a height of 40 cm) was 9.2.

The liquid distribution ratio from the liquid-diffusing member to the water-absorbent resin was determined by using the absorbent structure (8), and further an absorbent article (8) was produced as a model diaper by using the absorbent structure (8), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 2, and very excellent values were shown therein because the liquid distribution ratio from the liquid-diffusing member to the water-absorbent resin, and the liquid absorption ability of the water-absorbent resin from the liquid-diffusing member in a half upper portion of the diaper assumed sleep-on-face were 84% and 122 g respectively. However, the total absorption amount of the diaper was slightly low because the capillary absorption capacity of the liquid-diffusing member (3) was 6.6 (g/g) at a height of 0 cm.

Example 7

An absorbent structure (9) was obtained by combining the water-absorbent resin (3) with the liquid-diffusing member (3). The B/A (ratio of the capillary absorption index B of the water-absorbent resin (3) at a height of 40 cm to the capillary absorption index A of the liquid-diffusing member (3) at a height of 40 cm) was 0.4, and the D/C (ratio of the capillary absorption capacity D of the water-absorbent resin (3) at a height of 40 cm to the capillary absorption capacity C of the liquid-diffusing member (3) at a height of 40 cm) was 2.0.

The liquid distribution ratio from the liquid-diffusing member to the water-absorbent resin was determined by using the absorbent structure (9), and further an absorbent article (9) was produced as a model diaper by using the absorbent structure (9), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 2. It was excellent that the liquid distribution ratio from the liquid-diffusing member to the water-absorbent resin was 66%, but the liquid absorption ability of the water-absorbent resin from the liquid-diffusing member in a half upper portion of the diaper assumed sleep-on-face was 33 g. From this fact, the liquid absorption ability of the water-absorbent resin may be difficultly displayed in the combination of the water-absorbent resin (3) and the liquid-diffusing member (3) depending upon usage thereof, and therefore it is necessary to pay attention to this matter.

Examples 5 to 7 relate to examples in which a liquid-diffusing member having low capillary absorption capacities at heights of 0 and 40 cm was used. In Examples 5 and 6, the liquid distribution ratio from the liquid-diffusing member to the water-absorbent resin is high, and the absorption quantity of the water-absorbent resin in the diaper is large. Example 7 is an example in which only the liquid-diffusion-and-storage coefficient 2 is in the range of the present invention. In addition, the liquid-diffusing member has low capillary absorption capacities at heights of 0 and 40 cm in Examples 5 to 7, and therefore the total absorption amount of the diaper is low.

Comparative Example 3

An absorbent structure (10) was obtained by combining the water-absorbent resin (3) with the liquid-diffusing member (4). It was high that the B/A (ratio of the capillary absorption index B of the water-absorbent resin (3) at a height of 40 cm to the capillary absorption index A of the liquid-diffusing member (4) at a height of 40 cm) was 2.9, and that the D/C (ratio of the capillary absorption capacity D of the water-absorbent resin (3) at a height of 40 cm to the capillary absorption capacity C of the liquid-diffusing member (4) at a height of 40 cm) was 8.1. However, it was low that the capillary absorption capacity C of the liquid-diffusing member (4) was 0.5 (g/g) at a height of 40 cm, and that the capillary absorption index A of the liquid-diffusing member (4) was 0.04 (g/g) at a height of 40 cm, and therefore the liquid diffusion ability was low.

The liquid distribution ratio from the liquid-diffusing member to the water-absorbent resin was determined by using the absorbent structure (10), and further an absorbent article (10) was produced as a model diaper by using the absorbent structure (10), and determined were the liquid diffusion ratio in the liquid-diffusing member, the total absorption amount of the diaper when the leakage was caused, the liquid absorption quantity of the water-absorbent resin in the diaper, and the liquid absorption quantity of the water-absorbent resin in a half upper portion of the diaper. The results were listed in Table 2. It was excellent that the liquid distribution ratio from the liquid-diffusing member to the water-absorbent resin was 84%, but it was low that the liquid diffusion ratio in the diaper was 64%, and it was very low that the liquid absorption quantity of the water-absorbent resin in a half upper portion of the diaper assumed sleep-on-face was 16 g.

Comparative Example 4

Instead of the present invention absorbent structure, a diaper for children on the market ("Pampers Sarasara Care"; size: L; weight of diaper: 57 g; weight of absorbent structure: 24.0 g; weight of water-absorbent resin: 12.4 g; and weight of cotton pulp: 12.2 g) was used as an absorbent article (11). Determined were the liquid diffusion ratio in the liquid-diffusing member, and the total absorption amount of the diaper when the leakage was caused. The results were listed in Table 2, but it was low that the liquid diffusion ratio in the diaper was 62%.

TABLE 1

| | Example 1 | Example 2 | Example 3 | Comparative Example 1 | Example 4 | Example 5 |
|---|---|---|---|---|---|---|
| Liquid-diffusing member | (1) | (1) | (1) | (1) | (2) | (2) |
| Capillary absorption capacity at a height of 0 cm (g/g) | 33.6 | 33.6 | 33.6 | 39.3 | 27.0 | 27.0 |
| Capillary absorption capacity C at a height of 40 cm (g/g) | 14.2 | 14.2 | 14.2 | 12.6 | 7.6 | 7.6 |
| Capillary absorption Index A at a height of 40 cm | 0.42 | 0.42 | 0.42 | 0.32 | 0.28 | 0.28 |
| Suction height (cm) | 45 | 45 | 45 | 45 | 35 | 35 |
| Capillary absorption capacity at a height of 0 cm (g/g) | 45.5 | 33.8 | 37.8 | 45.5 | 45.5 | 37.8 |
| Capillary absorption capacity D at a height of 40 cm (g/g) | 27.4 | 19.4 | 4.30 | 27.4 | 27.4 | 4.30 |
| Capillary absorption Index B at a height of 40 cm | 0.60 | 0.57 | 0.11 | 0.60 | 0.60 | 0.11 |
| Absorption capacity (g/g) | 29 | 23 | 27 | 29 | 29 | 27 |
| Absorption capacity under a load of 2.07 kPa (0.3 psi) (g/g) | 36 | 27 | 33 | 36 | 36 | 33 |

TABLE 1-continued

|  | Example 1 | Example 2 | Example 3 | Comparative Example 1 | Example 4 | Example 5 |
|---|---|---|---|---|---|---|
| Absorption capacity under a load of 4.83 kPa (0.7 psi) (g/g) | 30 | 23 | 26 | 30 | 30 | 26 |
| Weight-average article diameter m | 105 | 120 | 420 | 105 | 105 | 420 |
| Particle diameter distribution (%) |  |  |  |  |  |  |
| 850 μm on | 0 | 0 | 0 | 0 | 0 | 0 |
| 500 to 800 μm | 0 | 0 | 37 | 0 | 0 | 37 |
| 300 to 500 μm | 0 | 0 | 34 | 0 | 0 | 34 |
| 150 to 300 μm | 10 | 31 | 25 | 10 | 10 | 25 |
| 75 to 150 μm | 74 | 55 | 4 | 74 | 74 | 4 |
| 45 to 75 μm | 13 | 12 | 1 | 13 | 13 | 1 |
| 45 μm through | 3 | 2 | 0 | 3 | 3 | 0 |
| Absorbent structure | (1) | (2) | (3) | (4) | (5) | (6) |
| Liquid-diffusion-and-storage coefficient 1 (B/A) | 1.4 | 1.4 | 0.3 | 1.9 | 2.1 | 0.4 |
| Liquid-diffusion-and-storage coefficient 2 (D/G) | 1.9 | 1.4 | 0.3 | 2.2 | 3.6 | 0.6 |
| Liquid distribution ratio (%) | 47 | 23 | 13 | 52 | 51 | 13 |
| Absorbent article | (1) | (2) | (3) | (4) | (5) | (6) |
| Amount of members as used for model diaper |  |  |  |  |  |  |
| Weight of liquid-diffusing member (g) | 6.7 | 6.7 | 6.7 | 3.4 | 6.7 | 6.7 |
| Weight of water-absorbent resin (g) | 13.6 | 13.6 | 13.6 | 13.6 | 13.6 | 13.6 |
| Weight of absorbent article (g) | 20.3 | 20.3 | 20.3 | 17 | 20.3 | 20.3 |
| Performance of model diaper |  |  |  |  |  |  |
| Liquid diffusion ratio in diaper (%) | 100 | 100 | 100 | 100 | 100 | 100 |
| Total absorption amount in diaper (g) | 639 | 500 | 505 | 485 | 532 | 447 |
| Liquid absorption quantity of water-absorbent resin in diaper (g) | 407 | 268 | 246 | 320 | 317 | 203 |
| Liquid absorption quantity of water-absorbent resin in upper half portion of diaper (g) | 165 | 102 | 33 | 81 | 77 | 17 |

TABLE 2

|  | Example 5 | Example 6 | Example 7 | Comparative Example 3 | Comparative Example 4 |
|---|---|---|---|---|---|
| Liquid-diffusing member | (3) | (3) | (3) | (4) | Diaper on market |
| Capillary absorption capacity at a height of 0 cm (g/g) | 66 | 66 | 66 | 13.7 |  |
| Capillary absorption capacity C at a height of 40 cm (g/g) | 2.1 | 2.1 | 2.1 | 0.5 |  |
| Capillary absorption index A at a height of 40 cm | 0.32 | 0.32 | 0.32 | 0.04 |  |
| Suction height (cm) | 30 | 30 | 30 | <10 |  |
| Water-absorbent resin | (1) | (2) | (3) | (3) |  |
| Capillary absorption capacity at a height of 0 cm (g/g) | 45.5 | 33.8 | 37.8 | 37.8 |  |
| Capillary absorption capacity D at a height of 40 cm (g/g) | 27.4 | 19.4 | 4.30 | 4.30 |  |
| Capillary absorption Index B at a height of 40 cm | 0.60 | 0.57 | 0.11 | 0.11 |  |
| Absorption capacity (g/g) | 29 | 23 | 27 | 27 |  |
| Absorption capacity under a load of 2.07 kPa (0.3 psi) (g/g) | 36 | 27 | 33 | 33 |  |
| Absorption capacity under a load of 4.83 kPa (0.7 psi) (g/g) | 30 | 23 | 26 | 26 |  |
| Weight-average particle diameter (μm) | 105 | 120 | 420 | 420 |  |
| Particle diameter distribution (%) |  |  |  |  |  |
| 850 μm on | 0 | 0 | 0 | 0 |  |
| 500 to 800 μm | 0 | 0 | 37 | 37 |  |
| 300 to 500 μm | 0 | 0 | 34 | 34 |  |
| 150 to 300 μm | 10 | 31 | 25 | 25 |  |
| 75 to 150 μm | 74 | 55 | 4 | 4 |  |
| 45 to 75 μm | 13 | 12 | 1 | 1 |  |
| 45 μm through | 3 | 2 | 0 | 0 |  |
| Absorbent structure | (7) | (8) | (9) | (10) |  |

TABLE 2-continued

|  | Example 5 | Example 6 | Example 7 | Comparative Example 3 | Comparative Example 4 |
|---|---|---|---|---|---|
| Liquid-diffusion-and-storage coefficient 1 (B/A) | 1.9 | 1.8 | 0.4 | 2.9 | |
| Liquid-diffusion-and-storage coefficient 2 (D/C) | 13.0 | 9.2 | 2.0 | 8.1 | |
| Liquid distribution ratio (%) | 87 | 84 | 66 | 84 | |
| Absorbent article | (7) | (8) | (9) | (10) | (11) |
| Amount of members as used for model diaper | | | | | |
| Weight of liquid-diffusing member (g) | 10.9 | 10.9 | 10.9 | 9.7 | 12.2 |
| Weight of water-absorbent resin (g) | 13.6 | 13.6 | 13.6 | 13.6 | 12.4 |
| Weight of absorbent article (g) | 24.8 | 24.5 | 24.8 | 23.3 | 24.0 |
| Performance of model diaper | | | | | |
| Liquid diffusion ratio in diaper (%) | 90 | 100 | 100 | 64 | 62 |
| Total absorption amount in diaper (g) | 439 | 381 | 371 | 377 | 354 |
| Liquid absorption quantity of water-absorbent resin in diaper (g) | 381 | 302 | 272 | 265 | |
| Liquid absorption quantity of water-absorbent resin in upper half portion of diaper (g) | 121 | 122 | 33 | 16 | |

Referential Example 8

Production Process for Water-Absorbent Resin (4)

A reaction liquid was obtained by dissolving 4.9 parts of polyethylene glycol diacrylate (n=8) into 5,500 parts of aqueous sodium acrylate solution having a monomer concentration of 33 weight % (neutralization ratio: 75 mol %). Next, this reaction liquid was deaerated under an atmosphere of nitrogen for 30 minutes. Subsequently, the above reaction liquid was supplied to a jacketed stainless-steel-made twin-arm kneader having: an lid that can be opened and shut; and two sigma type blades, and the system was replaced with a nitrogen gas while the reaction liquid was maintained at 30° C. Subsequently, 2.4 parts of ammonium persulfate and 0.12 part of L-ascorbic acid were added thereto while the reaction liquid was stirred, and then the polymerization was started after about one minute. Then, the polymerization was carried out at 30 to 90° C. After 60 minutes from the start of the polymerization, the resultant hydrogel polymer was taken out.

The crosslinked hydrogel polymer as obtained was in finely divided pieces having a diameter of about 5 mm. This finely divided crosslinked hydrogel polymer was spread on a wire net having 50 mesh, and hot-wind-dried at 150° C. for 90 minutes. Subsequently, the resultant dry material was pulverized with a vibration mill, and further classified with a wire net having 20 mesh, thus obtaining an unshaped pulverized resin having a weight-average particle diameter of 340 µm, in which the ratio of particles having particle diameters of smaller than 106 µm was 3 weight %.

Into 100 parts of the resin as obtained, a surface-crosslinking agent solution including 0.05 part of ethylene glycol diglycidyl ether, 0.9 part of propylene glycol, 3 parts of water, and 1 part of isopropyl alcohol was blended. The above mixture was heat-treated at 195° C. for 40 minutes, thus obtaining a water-absorbent resin (4). The water-absorbent resin (4) had a weight-average particle diameter of 347 µm. In addition, the water-absorbent resin (4) displayed a capillary absorption capacity of 39.9 (g/g) at a height of 0 cm, a capillary absorption capacity D of 11.4 (g/g) at a height of 40 cm, and a capillary absorption index B of 0.29 at a height of 40 cm.

Referential Example 9

Production Process for Water-Absorbent Resin (5)

A reaction liquid was obtained by dissolving 8.1 parts of polyethylene glycol diacrylate (n=8) into 5,500 parts of aqueous sodium acrylate solution having a monomer concentration of 38 weight % (neutralization ratio: 71 mol %). Next, this reaction liquid was deaerated under an atmosphere of nitrogen for 30 minutes. Subsequently, the above reaction liquid was supplied to a jacketed stainless-steel-made twin-arm kneader having: an lid that can be opened and shut; and two sigma tripe blades, and the system was replaced with a nitrogen gas while the reaction liquid was maintained at 30° C. Subsequently, 2.4 parts of ammonium persulfate and 0.12 part of L-ascorbic acid were added thereto while the reaction liquid was stirred, and then the polymerization was started after about one minute. Then, the polymerization was carried out at 20 to 95° C. After 60 minutes from the start of the polymerization, the resultant hydrogel polymer was taken out.

The crosslinked hydrogel polymer as obtained was in finely divided pieces having a diameter of about 5 mm. This finely divided crosslinked hydrogel polymer was spread on a wire net having 50 mesh, and hot-wind-dried at 150° C. for 90 minutes. Subsequently, the resultant dry material was pulverized with a vibration mill, and further classified with a wire net having 20 mesh, thus obtaining an unshaped pulverized resin having a weight-average particle diameter of 400 µm, which was further passed through a sieve having a mesh opening size of 850 µm and left on a sieve having a mesh opening size of 106 µm.

Into 100 parts of the resin as obtained, a surface-crosslinking agent solution including 0.3 part of 1,4-butanediol, 0.5 part of propylene glycol, and 3 parts of water was blended. The above mixture was heat-treated at 210° C. for 30 minutes. Thereafter, 0.5 part of hydrophilic silicon dioxide fine powder (Aerosil 200, produced by Nippon Aerosil Co., Ltd.) was added thereto in order to coat the surface portion therewith, thus obtaining a water-absorbent resin (5). The water-absorbent resin (5) had a weight-average particle diameter of 500 µm. In addition, the water-absorbent resin (5) displayed a capillary absorption capacity of 37.4 (g/g) at a height of 0 cm, a capillary absorption capacity D of 2.8 (g/g) at a height of 40 cm, and a capillary absorption index B of 0.08 at a height of 40 cm.

Referential Example 10

Production Process for Liquid-Acquiring Member (1)

Crosslinked cellulose as used for a diaper for children on the market ("Pampers Sarasara Care"; size: L; and weight of diaper: 57 g) was taken out in order to use a liquid-acquiring member (1) having a size of 8 cm×30 cm, wherein the crosslinked cellulose was in a state where its upper and lower portions were covered with nonwoven fabrics. In addition, the liquid-acquiring member (1) displayed a capillary absorption capacity of 14.4 (g/g) at a height of 0 cm, a capillary absorption capacity C of 0.18 (g/g) at a height of 40 cm, and a capillary absorption index A of 0.014 at a height of 40 cm.

Referential Example 11

Production Process for Liquid-Acquiring Member (2)

In order to produce a sheet, 3 g of cotton pulp as used for a diaper for children was spread over a size of 8 cm×30 cm, and the resultant sheet was used as a liquid-acquiring member (2) (density: 0.03 g/cm$^3$; and weight per unit area: 260 g/m$^2$). The liquid-acquiring member (2) displayed a capillary absorption capacity of 13.8 (g/g) at a height of 0 cm, a capillary absorption capacity C of 0.53 (g/g) at a height of 40 cm, and a capillary absorption index A of 0.038 at a height of 40 cm.

Example 8

A water-absorbent resin layer having a scattering amount of 360 g/m$^2$ was formed by scattering 16.4 g of the water-absorbent resin (4) over an area of 12 cm×38 cm, and then the liquid-acquiring member (1) (12 cm×24 cm, and weight: 3.8 g) was mounted thereon according to the aforementioned preparation method, thus obtaining an absorbent structure (12). The B/A (ratio of the capillary absorption index B of the water-absorbent resin (4) at a height of 40 cm to the capillary absorption index A of the liquid-acquiring member (1) at a height of 40 cm) was 20.7, and the capillary absorption capacity C of the liquid-acquiring member (1) was 0.18 (g/g) at a height of 40 cm, and the capillary absorption capacity D of the water-absorbent resin (4) was 11.4 (g/g) at a height of 40 cm.

An absorbent article (12) was produced as a model diaper by using the absorbent structure (12) according to the aforementioned preparation method, and determined were the liquid-absorbing time, the whitening time, the residual liquid amount in the liquid-acquiring member, and the amount of wet back of the aqueous liquid. The results were listed in Table 3, and it would be understood that the water-absorbent resin layer absorbs favorably a liquid from the liquid-acquiring member, and the diaper having excellent dry feeling is obtained, because the whitening time was also fast, and the residual liquid amount in the liquid-acquiring member was small, and the amount of wet back of the aqueous liquid was also small.

Example 9

An absorbent structure (13) was obtained by combining the water-absorbent resin (2) with the liquid-acquiring member (1) in the same way as of Example 8. The B/A (ratio of the capillary absorption index B of the water-absorbent resin (2) at a height of 40 cm to the capillary absorption index A of the liquid-acquiring member (1) at a height of 40 cm) was 41.0, and the capillary absorption capacity of the liquid-acquiring member (1) was 0.18 (g/g) at a height of 40 cm, and the capillary absorption capacity D of the water-absorbent resin (2) was 19.4 (g/g) at a height of 40 cm.

An absorbent article (13) was produced as a model diaper by using the absorbent structure (13) according to the aforementioned preparation method, and determined were the liquid-absorbing time, the whitening time, the residual liquid amount in the liquid-acquiring member, and the amount of wet back of the aqueous liquid. The results were listed in Table 3, and it would be understood that the water-absorbent resin layer absorbs favorably a liquid from the liquid-acquiring member, and the diaper having excellent dry feeling is obtained, because the whitening time was also fast, and the residual liquid amount in the liquid-acquiring member was small, and the amount of wet back of the aqueous liquid was also small.

Example 10

An absorbent structure (14) was obtained by combining the water-absorbent resin (1) with the liquid-acquiring member (1) in the same way as of Example 8. The B/A (ratio of the capillary absorption index B of the water-absorbent resin (1) at a height of 40 cm to the capillary absorption index A of the liquid-acquiring member (1) at a height of 40 cm) was 43.0, and the capillary absorption capacitor of the liquid-acquiring member (1) was 0.18 (g/g) at a height of 40 cm, and the capillary absorption capacity D of the water-absorbent resin (1) was 27.4 (g/g) at a height of 40 cm.

An absorbent article (14) was produced as a model diaper by using the absorbent structure (14) according to the aforementioned preparation method, and determined were the liquid-absorbing time, the whitening time, the residual liquid amount in the liquid-acquiring member, and the amount of wet back of the aqueous liquid. The results were listed in Table 3, and it would be understood that the water-absorbent resin layer absorbs favorably a liquid from the liquid-acquiring member, and the diaper having excellent dry feeling is obtained, because the whitening time was also fast, and the residual liquid amount in the liquid-acquiring member was small, and the amount of wet back of the aqueous liquid was also small.

Example 11

An absorbent structure (15) was obtained by combining the water-absorbent resin (4) with the liquid-acquiring member (2) in the same way as of Example 8. The B/A (ratio of the capillary absorption index B of the water-absorbent resin (4) at a height of 40 cm to the capillary absorption index A of the liquid-acquiring member (2) at a height of 40 cm) was 7.6, and the capillary absorption capacity of the liquid-acquiring member (2) was 0.53 (g/g) at a height of 40 cm, and the capillary absorption capacity D of the water-absorbent resin (4) was 11.4 (g/g) at a height of 40 cm.

An absorbent article (15) was produced as a model diaper by using the absorbent structure (15) according to the aforementioned preparation method, and determined were the liquid-absorbing time, the whitening time, the residual liquid amount in the liquid-acquiring member, and the amount of wet back of the aqueous liquid. The results were listed in Table 3, and it would be understood that the water-absorbent resin layer absorbs favorably a liquid from the liquid-acquiring member, and the diaper having excellent dry feeling is obtained, because the whitening time was also fast, and the residual liquid amount in the liquid-acquiring member was small, and the amount of wet back of the aqueous liquid was also small.

Comparative Example 5

An absorbent structure (16) was obtained by combining the water-absorbent resin (5) with the liquid-acquiring member (1) in the same way as of Example 8. The B/A (ratio of the capillary absorption index B of the water-absorbent resin (5) at a height of 40 cm to the capillary absorption index A of the liquid-acquiring member (1) at a height of 40 cm) was 5.4, and the capillary absorption capacity of the liquid-acquiring member (1) was 0.18 (g/g) at a height of 40 cm, and the capillary absorption capacity D of the water-absorbent resin (5) was 2.8 (g/g) at a height of 40 cm.

An absorbent article (16) was produced as a model diaper by using the absorbent structure (16) according to the aforementioned preparation method, and determined were the liquid-absorbing time, the whitening time, the residual liquid amount in the liquid-acquiring member, and the amount of wet back of the aqueous liquid. The results were listed in Table 4, and it would be understood that the liquid absorption cannot smoothly be carried out from the liquid-acquiring member to the water-absorbent resin layer, because the whitening time was late, and the residual liquid amount in the liquid-acquiring member and the amount of wet back of the aqueous liquid were also large.

Comparative Example 6

An absorbent structure (17) was obtained by combining the water-absorbent resin (3) with the liquid-acquiring member (1) in the same way as of Example 8. The B/A (ratio of the capillary absorption index B of the water-absorbent resin (3) at a height of 40 cm to the capillary absorption index A of the liquid-acquiring member (1) at a height of 40 cm) was 8.1, and the capillary absorption capacity of the liquid-acquiring member (1) was 0.18 (g/g) at a height of 40 cm, and the capillary absorption capacity D of the water-absorbent resin (3) was 4.3 (g/g) at a height of 40 cm.

An absorbent article (17) was produced as a model diaper by using the absorbent structure (17) according to the aforementioned preparation method, and determined where the liquid-absorbing time, the whitening time, the residual liquid amount in the liquid-acquiring member, and the amount of wet back of the aqueous liquid. The results were listed in Table 4, and it would be understood that the liquid absorption cannot smoothly be carried out from the liquid-acquiring member to the water-absorbent resin layer, because the whitening time was late, and the amount of wet back of the aqueous liquid was also large.

Comparative Example 7

A blended core having a size of 12 cm×38 cm was prepared by blending 8.2 g of the water-absorbent resin (4) with 8.2 g of cotton pulp used for disposable diapers for children. The capillary absorption abilities of these materials were listed in Table 4. The liquid-acquiring member (1) and the above blended core were combined in using amounts as mentioned in Table 4, thus obtaining an absorbent structure (18). The B/A (ratio of the capillary absorption index B of the above blended core at a height of 40 cm to the capillary absorption index A of the liquid-acquiring member (1) at a height of 40 cm) was 5.6, and the capillary absorption capacity of the liquid-acquiring member (1) was 0.18 (g/g) at a height of 40 cm, and the capillary absorption capacity D of the above blended core was 2.3 (g/g) at a height of 40 cm.

An absorbent article (18) was produced as a model diaper by using the absorbent structure (18) according to the aforementioned preparation method, and determined were the liquid absorption rate, the rate of drying the liquid-diffusing member, the residual liquid amount in the liquid-acquiring member after 1 hour, and the amount of wet back of the aqueous liquid. The results were listed in Table 4, and it would be understood that the liquid absorption cannot smoothly be carried out from the liquid-acquiring member to the water-absorbent resin layer, because the whitening time was late, and the residual liquid amount in the liquid-acquiring member and the amount of wet back of the aqueous liquid were also large.

Comparative Example 8

An absorbent structure (19) was prepared in the same way as of Example 8 except for not using the liquid-diffusing member, and determined were the liquid absorption rate, the rate of drying the liquid-diffusing member, the residual liquid amount in the liquid-acquiring member after 1 hour, and the amount of wet back of the aqueous liquid. The results were listed in Table 4, and it would be understood that the liquid-absorbing time is very late, and the liquid is not smoothly absorbed.

TABLE 3

|  | Example 8 | Example 9 | Example 10 | Example 11 |
|---|---|---|---|---|
| Liquid-acquiring member | (I) | (II) | (1) | (2) |
| Capillary absorption capacity at a height of 0 cm (g/g) | 14.4 | 14.4 | 14.4 | 13.8 |
| Capillary absorption capacity C at a height of 40 cm (g/g) | 0.18 | 0.18 | 0.18 | 0.53 |
| Capillary absorption Index A at a height of 40 cm | 0.014 | 0.014 | 0.014 | 0.038 |
| Water-absorbent resin | (4) | (2) | (1) | (4) |
| Capillary absorption capacity at a height of 0 cm (g/g) | 39.9 | 33.8 | 45.5 | 39.9 |
| Capillary absorption capacity D at a height of 40 cm (g/g) | 11.4 | 19.4 | 27.4 | 11.4 |
| Capillary absorption Index B at a height of 40 cm | 0.29 | 0.57 | 0.60 | 0.29 |
| Absorption capacity (g/g) | 32 | 23 | 29 | 32 |
| Absorption capacity under a load of 2.07 kPa (0.3 psi) (g/g) | 33 | 27 | 36 | 33 |
| Absorption capacity under a load of 4.83 kPa (0.7 psi) (g/g) | 25 | 23 | 30 | 25 |
| Weight-average particle diameter (μm) | 347 | 120 | 105 | 347 |
| Particle diameter distribution (%) |  |  |  |  |
| 850 μm on | 0 | 0 | 0 | 0 |
| 500 to 800 μm | 13 | 0 | 0 | 13 |
| 300 to 500 μm | 51 | 0 | 0 | 51 |
| 150 to 300 μm | 29 | 31 | 10 | 29 |
| 75 to 150 μm | 6 | 55 | 74 | 6 |
| 45 to 75 gm | 1 | 12 | 13 | 1 |
| 45 μm through | 0 | 2 | 3 | 0 |

TABLE 3-continued

|  | Example 8 | Example 9 | Example 10 | Example 11 |
|---|---|---|---|---|
| Absorbent structure | (12) | (13) | (14) | (15) |
| Liquid-acquirement-and-storage coeffcient 1 (B/A) | 20.7 | 41.0 | 43.0 | 7.6 |
| Liquid-acquirement-and-storage coefficient 2 (D/C) | 63.3 | 107.8 | 152.2 | 21.5 |
| Absorbent article | (12) | (13) | (14) | (15) |
| Amount of members as used for model diaper |  |  |  |  |
| Weight of liquid-acquiring member (g) | 3.8 | 3.8 | 3.8 | 3.8 |
| Weight of water-absorbent resin (g) | 16.4 | 16.4 | 16.4 | 16.4 |
| Weight of absorbent article (g) | 20.2 | 20.2 | 20.2 | 20.2 |
| Performance of model diaper |  |  |  |  |
| Liquid-absorbing time (sec) |  |  |  |  |
| First time, Second time | 14, 31 | 13, 35 | 15, 35 | 12, 27 |
| Third time, Fourth time | 54, 61 | 58, 54 | 65, 55 | 68, 50 |
| Whitening time (mm) |  |  |  |  |
| First time, Second time | 1, 2 | 1, 3 | 1, 2 | 1, 2 |
| Third time, Fourth time | 14, 25 | 15, 25 | 10, 15 | 11, 25 |
| Residual liquid amount in liquid-acquiring member (g) |  |  |  |  |
| First time, Second time | 1.3, 1.9 | 1.1, 3.4 | 1.4, 2.4 | 1.8, 2.8 |
| Third time, Fourth time | 6.3, 11.2 | 7.6, 10.7 | 5.2, 8.6 | 9.0, 15.1 |
| Amount of wet back of aqueous liquid (g) | 0.7 | 4.8 | 1.0 | 6.1 |

TABLE 4

|  | Comparative Example 5 | Comparative Example 6 | Comparative Example 7 | Comparative Example 8 |
|---|---|---|---|---|
| Liquid-acquiring member | (1) | (1) | (1) | None |
| Capillary absorption capacity at a height 0 cm (g/g) | 14.4 | 14.4 | 14.4 |  |
| Capillary absorption capacity C at a height of 40 cm (g/g) | 0.18 | 0.18 | 0.18 |  |
| Capillary absorption Index A at a height of 40 cm | 0.014 | 0.014 | 0.014 |  |
| Water-absorbent resin | (5) | (3) | Blended core | (4) |
| Capillary absorption capacity at a height of 0 cm (g/g) | 37.4 | 37.8 | 30.0 | 39.9 |
| Capillary absorption capacity D at a height of 40 cm (g/g) | 2.8 | 4.30 | 2.3 | 11.4 |
| Capillary absorption Index B at a height of 40 cm | 0.08 | 0.11 | 0.08 | 0.29 |
| Absorption capacity (g/g) | 26 | 27 |  | 32 |
| Absorption capacity under a load of 2.07 k-Pa (0.3 psi) (g/g) | 27 | .33 |  | 33 |
| Absorption capacity under a load of 4.83 kPa (0.7 psi) (g/g) | 21 | 26 |  | 25 |
| Weight-average particle diameter (μm) | 500 | 420 |  | 347 |
| Particle diameter distribution (%) |  |  |  |  |
| 850 μm on | 0 | 0 |  | 0 |
| 800 to 800 μm | 52 | 37 |  | 13 |
| 300 to 500 μm | 36 | 34 |  | 51 |
| 150 to 300 μm | 12 | 25 |  | 29 |
| 75 to 150 μm | 0 | 4 |  | 6 |
| 45 to 75 μm | 0 | 1 |  | 1 |
| 45 75 μm through | 0 | 0 |  | 0 |
| Absorbent structure | (16) | (17) | (18) | (19) |
| Liquid-acquirement-and-storage coefficient 1 (B/A) | 5.4 | 8.1 | 5.6 |  |
| Liquid-acquirement-and-storage coefficient 2 (D/C) | 15.6 | 23.9 | 13.0 |  |
| Absorbent article | (16) | (17) | (18) | (19) |
| Amount of members as used for model diaper |  |  |  |  |
| Mass of liquid-acquiring member (g) | 3.8 | 3.8 | 3.8 | 0 |
| Mass of water-absorbent resin (g) | 16.4 | 16.4 | 16.4* | 16.4 |
| Mass of absorbent article (g) | 20.2 | 20.2 | 20.2 | 20.2 |
| Performance of model diaper |  |  |  |  |
| Liquid-absorbing time (sec) |  |  |  |  |
| First time, Second time Third time, Fourth time | 13, 20 12, 8 | 18, 23 40, 43 | 11, 19 31, 43 | 39, 120 162, 161 |
| Whitening time (min) |  |  |  |  |
| First time, Second time, Third time, Fourth time | 1, >6 >60, >60 | 1, 3 55, >60 | 4, >60 >60, >60 | 1, 5 30, >60 |
| Residual liquid amount in liquid-acquiring member (g) |  |  |  |  |
| First time, Second time Third time, Fourth time | 2.4, 10.6 22.1, 25.6 | 1.5, 2.8 12.7, 17.5 | 3.9, 14.6 19.4, 22.6 |  |
| Amount of wet back of aqueous liquid (g) | 15.2 | 9.6 | 34.6 | 12.9 |

*Water-absorbent resin 8.2 g + cotton pulp 8.2 g

Referential Example 12

Production Process for Water-Absorbent Resin (6)

A reaction liquid was obtained by dissolving 4.9 parts of polyethylene glycol diacrylate (n=8) into 5,500 parts of aqueous sodium acrylate solution having a monomer concentration of 33 weight % (neutralization ratio: 75 mol %). Next, this reaction liquid was deaerated under an atmosphere of nitrogen for 30 minutes. Subsequently, the above reaction liquid was supplied to a jacketed stainless-steel-made twin-arm kneader having: an lid that can be opened and shut; and two sigma type blades, and the system was replaced with a nitrogen gas while the reaction liquid was maintained at 30° C. Subsequently, 2.4 parts of ammonium persulfate and 0.12 part of L-ascorbic acid were added thereto while the reaction liquid was stirred, and then the polymerization was started after about one minute. Then, the polymerization was carried out at 30 to 90° C. After 60 minutes from the start of the polymerization, the resultant hydrogel polymer was taken out.

The crosslinked hydrogel polymer as obtained was in finely divided pieces having a diameter of about 5 mm. This finely divided crosslinked hydrogel polymer was spread on a wire net having 50 mesh, and lot-wind-dried at 150° C. for 90 minutes. Subsequently, the resultant dry material was pulverized with a vibration mill, and further classified with a wire net having 30 mesh, thus obtaining an unshaped pulverized water-absorbent resin precursor having a weight-average particle diameter of 280 μm, in which the ratio of particles having particle diameters of smaller than 106 μm was 5 weight %.

Into 100 parts of the water-absorbent resin precursor as obtained, a surface-crosslinking agent solution including 0.05 part of ethylene glycol diglycidyl ether, 0.9 part of propylene glycol, 3 parts of water, and 1 part of isopropyl alcohol was blended. The above mixture was heat-treated at 195° C. for 40 minutes, thus obtaining a water-absorbent resin (6). The water-absorbent resin (6) had a weight-average particle diameter of 265 μm. In addition, the water-absorbent resin (6) displayed a capillary absorption capacity D of 11.4 (g/g) at a height of 40 cm. As to the particle diameter distribution of the water-absorbent resin (6), particles having particle diameters of 150 to 850 μm and particles having particle diameters of smaller than 150 μm accounted for 90 weight % and 10 weight % respectively.

Referential Example 13

Dispersion of Water-Dispersible Fine Particles

Five parts by weight of Aerosil 200 (super-fine particles of silicon dioxide, produced by Nippon Aerosil Co., Ltd.) as water-dispersible fine particles were blended into 70 parts by weight of deionized water with a high-speed continuous blender (2,000 rpm) for 2 hours. After the blending, the resultant mixture was allowed to stand at room temperature for 24 hours, thus obtaining a dispersion of the water-dispersible fine particles. The viscosity of the water-dispersible fine particles was 1,000 cps.

Example 12

To 100 parts by weight of the water-absorbent resin (6), 7 parts by weight of the dispersion of the water-dispersible fine particles as obtained in Referential Example 13 was added and blended. After the resultant mixture was allowed to stand at 60° C. for 30 minutes, the mixture was ground, and the entire particles was passed through a wire net with a mesh opening size of 850 μm, thus obtaining water-absorbent resin particles (1) according to the present invention. As to the particle diameter distribution of these particles, particles having particle diameters of 150 to 850 μm and particles having particle diameters of smaller than 150 μm accounted for 97 weight % and 3 weight % respectively. In addition, the particles have a weight-average particle diameter of 500 μm. The results were listed in Table 5.

An absorbent article (20) was produced as a model diaper by using the water-absorbent resin particles (1) and the liquid-acquiring member (2) as obtained according to the aforementioned method. The liquid-absorbing time, the diffusion area, and the amount of wet back of the aqueous liquid were evaluated according to the above evaluation method, and the results were listed in Table 5.

Example 13

A dispersion was obtained by blending 7 parts by weight of the dispersion of the water-dispersible fine particles as obtained in Referential Example 13 and 13 parts by weight of deionized water. To 100 parts by weight of the water-absorbent resin (2), 20 parts by weight of the dispersion was added and blended. After the resultant mixture was allowed to stand at 60° C. for 30 minutes, the mixture was ground, and the entire particles was passed through a wire net with a mesh opening size of 850 μm, thus obtaining water-absorbent resin particles (2) according to the present invention. As to the particle diameter distribution of these particles, particles having particle diameters of 150 to 850 μm and particles having particle diameters of smaller than 150 μm accounted for 85 weight % and 15 weight % respectively. In addition, the particles have a weight-average particle diameter of 308 μm.

An absorbent article (21) was produced as a model diaper by using the water-absorbent resin particles (2) and the liquid-acquiring member (2) as obtained according to the aforementioned method. The liquid-absorbing time, the diffusion area, and the amount of wet back of the aqueous liquid were evaluated according to the above evaluation method, and the results were listed in Table 5.

Comparative Example 9

To 100 parts by weight of the water-absorbent resin (2), 0.5 part by weight of Aerosil 200 (silicon dioxide fine powder, produced by Nippon Aerosil Co., Ltd.) was added to blend the water-absorbent resin, and further 20 parts by weight of deionized water was added thereto and blended. After the resultant mixture was allowed to stand at 60° C. for 30 minutes, the mixture was ground, and the entire particles was passed through a wire net with a mesh opening size of 850 μm, thus obtaining water-absorbent resin particles (3). As to the particle diameter distribution of these particles, particles having particle diameters of 150 to 850 μm and particles having particle diameters of smaller than 150 μm accounted for 59 weight % and 41 weight % respectively. In addition, the particles have a weight-average particle diameter of 174 μm.

An absorbent article (22) was produced as a model diaper by using the water-absorbent resin particles (3) and the liquid-acquiring member (2) as obtained according to the aforementioned method. The liquid-absorbing time, the diffusion area, and the amount of wet back of the aqueous liquid were evaluated according to the above evaluation method, and the results were listed in Table 5.

Comparative Example 10

To 100 parts by weight of the water-absorbent resin (2), 20 parts by weight of deionized water was added thereto and blended. After the resultant mixture was allowed to stand at 60° C. for 30 minutes, the mixture was ground, and the entire particles was passed through a wire net with a mesh opening size of 850 μm, thus obtaining water-absorbent resin particles (4). As to the particle diameter distribution of these particles, particles having particle diameters of 150 to 850 μm and particles having particle diameters of smaller than 150 μm accounted for 61 weight % and 39 weight % respectively. In addition, the particles have a weight-average particle diameter of 180 μm, but they were fragile and easily destroyed.

An absorbent article (23) was produced as a model diaper by using the water-absorbent resin particles (4) and the liquid-acquiring member (2) as obtained according to the aforementioned method. The liquid-absorbing time, the diffusion area, and the amount of wet back of the aqueous liquid were evaluated according to the above evaluation method, and the results were listed in Table 5.

Comparative Example 11

An absorbent article (24) was produced as a model diaper by using the water-absorbent resin (2) and the liquid-acquiring member (2) as obtained according to the aforementioned method. The liquid-absorbing time, the diffusion area, and the amount of wet back of the aqueous liquid were evaluated according to the above evaluation method, and the results were listed in Table 5. When the absorbent structure was produced, dusts were scattered and its handling was difficult.

Comparative Example 12

An absorbent article (25) was produced as a model diaper by using the water-absorbent resin (3) and the liquid-acquiring member (2) as obtained according to the aforementioned method. The liquid-absorbing time, the diffusion area, and the amount of wet back of the aqueous liquid were evaluated according to the above evaluation method, and the results were listed in Table 5.

TABLE 5

|  | Example 12 | Example 13 | Comparative Example 9 | Comparative Example 10 | Comparative Example 11 | Comparative Example 12 |
|---|---|---|---|---|---|---|
| Liquid-acquiring member | (2) | (2) | (2) | (2) | (2) | (2) |
| Capillary absorption capacity at a height of 0 cm (g/g) | 13.8 | 13.8 | 13.8 | 13.8 | 13.8 | 13.8 |
| Capillary absorption capacity C at a height of 40 cm (g/g) | 0.53 | 0.53 | 0.53 | 0.53 | 0.53 | 0.53 |
| Water-absorbent resin | (6) | (2) | (2) | (2) | (2) | (2) |
| Space ratio of swollen gel without load (%) | 41 | 43 | 43 | 43 | 43 | 39 |
| Average space radius of swollen gel without load (μm) | 98 | 96 | 96 | 96 | 96 | 120 |
| Weight-average particle diameter (μm) | 265 | 121 | 121 | 121 | 121 | 413 |
| Capillary absorption capacity at a height of 0 cm (g/g) | 40 | 34 | 34 | 34 | 34 | 38 |
| Capillary absorption capacity D at a height of 40 cm (g/g) | 11 | 19 | 19 | 19 | 19 | 4 |
| Water-absorbent resin particles | (1) | (2) | (3) | (4) |  |  |
| Capillary absorption capacity D at a height of 40 cm (g/g) | 11 | 14 | 18 | 19 |  |  |
| Absorption capacity (g/g) | 32 | 23 | 23 | 23 | 23 | 29 |
| Weight-average particle diameter (μm) | 500 | 308 | 174 | 180 | 121 | 413 |
| Particle diameter distribution (%) |  |  |  |  |  |  |
| 850 μm on | 0 | 0 | 0 | 0 | 0 | 0 |
| 500 to 500 μm | 56 | 32 | 2 | 2 | 0 | 37 |
| 300 to 500 μm | 28 | 19 | 18 | 20 | 0 | 34 |
| 150 to 300 μm | 13 | 34 | 39 | 39 | 31 | 24 |
| 70 to 150 μm | 3 | 14 | 33 | 33 | 55 | 4 |
| 45 to 75 μm | 0 | 1 | 7 | 5 | 12 | 1 |
| 45 μm through | 0 | 0 | 1 | 1 | 2 | 0 |
| Absorbent article | (20) | (21) | (22) | (23) | (24) | (25) |
| Performance of model diaper |  |  |  |  |  |  |
| Liquid-absorbing time (sec) |  |  |  |  |  |  |
| First time | 10 | 8 | 13 | 13 | 13 | 13 |
| Second time | 27 | 18 | 35 | 39 | 35 | 15 |
| Third time | 68 | 35 | 38 | 54 | 58 | 26 |
| Fourth time | 50 | 51 | 44 | 50 | 543 | 37 |
| Diffusion area (%) |  |  |  |  |  |  |
| Fourth time | 78 | 81 | 81 | 81 | 81 | 76 |
| Amount of wet back of aqueous liquid (g) | 6.1 | 5.0 | 5.0 | 4.5 | 4.8 | 6.6 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

INDUSTRIAL APPLICATION

The present invention can provide: an absorbent structure and an absorbent article, in which, in the absorbent structure and the absorbent article comprising a liquid-diffusing member and a water-absorbent resin, a liquid is sufficiently transferred and absorbed from the liquid-diffusing member to the water-absorbent resin even if an auxiliary material such as a material having a large surface area is not used, namely which are excellent in both liquid diffusion ability and liquid storage ability; and a water-absorbent resin fitly usable for the above absorbent structure and absorbent article. In addition, the present invention can provide: an absorbent structure and an absorbent article, in which, in the absorbent structure and the absorbent article comprising a liquid-acquiring member and a water-absorbent resin, a liquid is favorably transferred from the liquid-acquiring member to the water-absorbent resin even if the concentration of the water-absorbent resin is raised more, and the liquid-acquiring function is not lowered so much even if the liquid is repeatedly absorbed, and which are excellent in the dry feeling and the amount of wet back of the aqueous liquid, and which can realize the thinning and lightening more; and a water-absorbent resin fitly usable for the above absorbent structure and absorbent article.

The invention claimed is:

1. Water-absorbent resin particles, which comprise a crosslinked poly(acrylic acid (salt)) polymer in a major proportion and display a weight-average particle diameter of 150 to 600 μm, a capillary absorption capacity D of not less than 30 (g/g) at a height of 0 cm, and a capillary absorption capacity D of not less than 15 (g/g) at a height of 40 cm, and display a capillary absorption index B at a height of 40 cm of not less than 0.4, wherein the capillary absorption index B=the capillary absorption capacity D at a height of 40 cm/the capillary absorption capacity D of at a height of 0 cm wherein the capillary absorption capacity D at a height of 40 cm is an absorption capacity calculated from the absorption quantity (g) of 0.44 g of the water-absorbent resin in a state where the liquid-absorbing position (H1) is 40 cm higher than the liquid surface height (H2) in a liquid-storing receptacle, under a load of 0.06 psi for 30 minutes.

2. Water-absorbent resin particles according to claim 1, which are obtained by a process including the step of granulating a water-absorbent resin having a weight-average particle diameter of 50 to 300 μm.

3. Water-absorbent resin particles according to claim 1, which have a weight-average particle diameter as increased by not less than 50% of that before the granulating step.

4. Water-absorbent resin particles according to claim 1, which further comprises water-insoluble fine-particulate inorganic powders.

5. An absorbent article, which comprises the water-absorbent particles as recited in claim 1.

6. Water-absorbent resin particles according to claim 1, which display a capillary absorption index B at a height of 40 cm of not less than 0.5.

7. Water-absorbent resin particles according to claim 1, wherein the surface of the water-absorbent resin particles are crosslinked with a surface-crosslinking agent.

8. Water-absorbent resin particles according to claim 1, which display a capillary absorption capacity D at a height of 40 cm of not less than 20 (g/g).

* * * * *